US011312768B2

(12) United States Patent
Michelsen et al.

(10) Patent No.: US 11,312,768 B2
(45) Date of Patent: Apr. 26, 2022

(54) SIGNATURE OF TL1A (TNFSF15) SIGNALING PATHWAY

(71) Applicant: CEDARS-SINAI MEDICAL CENTER, Los Angeles, CA (US)

(72) Inventors: Kathrin S. Michelsen, Los Angeles, CA (US); Stephan R. Targan, Santa Monica, CA (US)

(73) Assignee: CEDARS-SINAI MEDICAL CENTER, Los Angeles, CA (US)

( * ) Notice: Subject to any disclaimer, the term of this patent is extended or adjusted under 35 U.S.C. 154(b) by 0 days.

(21) Appl. No.: 16/388,101

(22) Filed: Apr. 18, 2019

(65) Prior Publication Data

US 2020/0216526 A1     Jul. 9, 2020

Related U.S. Application Data

(63) Continuation of application No. 14/900,024, filed as application No. PCT/US2014/047326 on Jul. 18, 2014, now Pat. No. 10,316,083.

(60) Provisional application No. 61/856,491, filed on Jul. 19, 2013.

(51) Int. Cl.

| | |
|---|---|
| A61K 39/395 | (2006.01) |
| C12Q 1/68 | (2018.01) |
| G01N 33/50 | (2006.01) |
| G01N 33/53 | (2006.01) |
| G01N 33/564 | (2006.01) |
| G01N 33/96 | (2006.01) |
| G01N 33/68 | (2006.01) |
| C07K 16/24 | (2006.01) |
| A61K 45/06 | (2006.01) |
| C12Q 1/6883 | (2018.01) |
| G01N 33/483 | (2006.01) |
| C07K 14/54 | (2006.01) |
| C07K 14/525 | (2006.01) |
| G01N 33/569 | (2006.01) |
| G01N 15/14 | (2006.01) |
| A61K 39/00 | (2006.01) |

(52) U.S. Cl.
CPC ........ *C07K 16/241* (2013.01); *A61K 39/3955* (2013.01); *A61K 45/06* (2013.01); *C07K 16/244* (2013.01); *C12Q 1/68* (2013.01); *C12Q 1/6883* (2013.01); *G01N 33/483* (2013.01); *G01N 33/50* (2013.01); *G01N 33/53* (2013.01); *G01N 33/68* (2013.01); *G01N 33/6863* (2013.01); *A61K 2039/505* (2013.01); *C07K 2317/76* (2013.01); *C12Q 2600/106* (2013.01); *C12Q 2600/156* (2013.01); *C12Q 2600/158* (2013.01); *G01N 33/56966* (2013.01); *G01N 2015/149* (2013.01); *G01N 2333/5425* (2013.01); *G01N 2333/70575* (2013.01); *G01N 2800/065* (2013.01); *G01N 2800/12* (2013.01); *G01N 2800/24* (2013.01); *G01N 2800/7095* (2013.01)

(58) Field of Classification Search
CPC ........... G01N 33/6893; G01N 2800/52; G01N 2333/54; G01N 2800/50; G01N 2800/7095; G01N 2800/102; G01N 2800/24; G01N 33/53; G01N 33/48; G01N 33/483; G01N 33/50; G01N 33/68; G01N 2800/06; G01N 2800/12; A61K 2039/505; A61K 39/3955
See application file for complete search history.

(56) References Cited

U.S. PATENT DOCUMENTS

| | | |
|---|---|---|
| 3,654,090 A | 4/1972 | Antonius et al. |
| 3,850,752 A | 11/1974 | Schuurs et al. |
| 4,016,043 A | 4/1977 | Schuurs et al. |
| 4,265,823 A | 5/1981 | Nobile |
| 4,518,584 A | 5/1985 | Mark et al. |
| 4,698,195 A | 10/1987 | Okumura et al. |
| 4,699,880 A | 10/1987 | Goldstein |
| 4,704,692 A | 11/1987 | Ladner |
| 4,737,462 A | 4/1988 | Mark et al. |
| 4,800,159 A | 1/1989 | Mullis et al. |
| 4,880,548 A | 11/1989 | Pall et al. |
| 4,925,572 A | 5/1990 | Pall |
| 4,935,234 A | 6/1990 | Todd, III et al. |
| 4,946,778 A | 8/1990 | Ladner et al. |
| 5,002,873 A | 3/1991 | St. John et al. |
| 5,085,318 A | 2/1992 | Leverick |
| 5,091,302 A | 2/1992 | Newman et al. |
| 5,114,842 A | 5/1992 | Plow et al. |

(Continued)

FOREIGN PATENT DOCUMENTS

| | | |
|---|---|---|
| AU | 698604 B2 | 11/1998 |
| AU | 2014317991 A1 | 3/2016 |

(Continued)

OTHER PUBLICATIONS

Abraham et al.: Haplotypic polymorph isms of the TNFB gene. Immunogenetics 33:50-53 (1991).

(Continued)

*Primary Examiner* — Bridget E Bunner
(74) *Attorney, Agent, or Firm* — Wilson Sonsini Goodrich & Rosati

(57) ABSTRACT

The present invention relates to the finding that TL1A enhances differentiation of TH17 cells, and enhance IL17 secretion from TL17 cells. In one embodiment, the present invention provides a method of treating an inflammatory disease comprising determining the presence of a TL1A signaling profile, and treating the disease by administering a composition comprising a therapeutically effective dosage of one or more inhibitors of TL1A or TH17 cell differentiation. In another embodiment, the disease is characterized by TH17 differentiation.

10 Claims, 38 Drawing Sheets

Specification includes a Sequence Listing.

(56) References Cited

U.S. PATENT DOCUMENTS

| | | |
|---|---|---|
| 5,137,806 A | 8/1992 | Lemaistre et al. |
| 5,147,637 A | 9/1992 | Wright et al. |
| 5,210,015 A | 5/1993 | Gelfand et al. |
| 5,219,997 A | 6/1993 | Schlossman et al. |
| 5,225,539 A | 7/1993 | Winter |
| 5,227,369 A | 7/1993 | Rosen et al. |
| 5,234,810 A | 8/1993 | Kehrli, Jr. et al. |
| 5,235,049 A | 8/1993 | McClelland et al. |
| 5,236,081 A | 8/1993 | Fitzsimmons et al. |
| 5,263,743 A | 11/1993 | Jones |
| 5,264,554 A | 11/1993 | Newman |
| 5,272,263 A | 12/1993 | Hession et al. |
| 5,284,931 A | 2/1994 | Springer et al. |
| 5,411,842 A | 5/1995 | Ridgway et al. |
| 5,491,063 A | 2/1996 | Fisher et al. |
| 5,494,920 A | 2/1996 | Glasebrook et al. |
| 5,518,488 A | 5/1996 | Schluger |
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,590,769 A | 1/1997 | Lin |
| 5,607,879 A | 3/1997 | Wuu et al. |
| 5,624,821 A | 4/1997 | Winter et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,683,698 A | 11/1997 | Chavali et al. |
| 5,691,151 A | 11/1997 | Braun et al. |
| 5,713,061 A | 1/1998 | Yoshioka |
| 5,750,355 A | 5/1998 | Targan et al. |
| 5,830,675 A | 11/1998 | Targan et al. |
| 5,840,300 A | 11/1998 | Williams et al. |
| 5,861,155 A | 1/1999 | Lin |
| 5,874,233 A | 2/1999 | Targan et al. |
| 5,885,793 A | 3/1999 | Griffiths et al. |
| 5,905,827 A | 5/1999 | Naganuma et al. |
| 5,916,748 A | 6/1999 | Targan et al. |
| 5,937,862 A | 8/1999 | Targan et al. |
| 5,942,390 A | 8/1999 | Cominelli et al. |
| 5,947,281 A | 9/1999 | Kaneff |
| 5,968,741 A | 10/1999 | Plevy et al. |
| 5,969,108 A | 10/1999 | McCafferty et al. |
| 6,034,102 A | 3/2000 | Aiello |
| 6,074,835 A | 6/2000 | Braun et al. |
| 6,114,395 A | 9/2000 | Aiello |
| 6,172,197 B1 | 1/2001 | McCafferty et al. |
| 6,183,951 B1 | 2/2001 | Plevy et al. |
| 6,215,040 B1 | 4/2001 | Lee et al. |
| 6,297,367 B1 | 10/2001 | Tribouley |
| 6,300,064 B1 | 10/2001 | Knappik et al. |
| 6,348,316 B1 | 2/2002 | Taylor et al. |
| 6,376,176 B1 | 4/2002 | Taylor et al. |
| 6,406,701 B1 | 6/2002 | Pulido-Cejudo |
| 6,407,213 B1 | 6/2002 | Carter et al. |
| 6,479,284 B1 | 11/2002 | Marasco et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,599,719 B2 | 7/2003 | Yu et al. |
| 6,607,879 B1 | 8/2003 | Cocks et al. |
| 6,632,976 B1 | 10/2003 | Tomizuka et al. |
| 6,653,068 B2 | 11/2003 | Frisch et al. |
| 6,692,916 B2 | 2/2004 | Bevilacqua et al. |
| 6,706,484 B1 | 3/2004 | Knappik et al. |
| 6,713,061 B1 | 3/2004 | Yu et al. |
| 6,762,042 B2 | 7/2004 | Liu et al. |
| 6,812,339 B1 | 11/2004 | Venter et al. |
| 6,824,767 B2 | 11/2004 | Yu et al. |
| 6,824,989 B1 | 11/2004 | Eisinger et al. |
| 6,835,823 B2 | 12/2004 | Le et al. |
| 6,858,391 B2 | 2/2005 | Nunez et al. |
| 6,869,762 B1 | 3/2005 | Daly et al. |
| 6,905,827 B2 | 6/2005 | Wohlgemuth et al. |
| 6,950,827 B2 | 9/2005 | Jung |
| 7,060,869 B2 | 6/2006 | Tsien et al. |
| 7,138,237 B1 | 11/2006 | Targan et al. |
| 7,186,800 B1 | 3/2007 | Gentz et al. |
| 7,252,971 B2 | 8/2007 | Benson et al. |
| 7,264,963 B1 | 9/2007 | Knappik et al. |
| 7,285,267 B2 | 10/2007 | Gentz et al. |
| 7,332,156 B2 | 2/2008 | Bowman et al. |
| 7,332,631 B2 | 2/2008 | Hogarth et al. |
| 7,361,491 B2 | 4/2008 | Liu et al. |
| 7,361,733 B2 | 4/2008 | Hershberg et al. |
| 7,368,527 B2 | 5/2008 | Rosen et al. |
| 7,534,428 B2 | 5/2009 | Gentz et al. |
| 7,597,886 B2 | 10/2009 | Yu et al. |
| 7,612,181 B2 | 11/2009 | Wu et al. |
| 7,691,379 B2 | 4/2010 | Allan |
| 7,708,996 B2 | 5/2010 | Yu et al. |
| 7,709,218 B2 | 5/2010 | Gentz et al. |
| 7,745,391 B2 | 6/2010 | Mintz et al. |
| 7,759,079 B2 | 7/2010 | Oh et al. |
| 7,820,447 B2 | 10/2010 | Morris et al. |
| 7,820,798 B2 | 10/2010 | Yu et al. |
| 7,838,239 B2 | 11/2010 | Mitsuhashi et al. |
| 7,892,730 B2 | 2/2011 | Morris et al. |
| 7,993,833 B2 | 8/2011 | Begovich et al. |
| 8,003,099 B2 | 8/2011 | Auer et al. |
| 8,003,386 B1 | 8/2011 | Gentz et al. |
| 8,017,122 B2 | 9/2011 | Siadak et al. |
| 8,093,363 B2 | 1/2012 | Yu et al. |
| 8,263,743 B2 | 9/2012 | Smith et al. |
| 8,409,577 B2 | 4/2013 | Thompson et al. |
| 8,450,069 B2 | 5/2013 | Goix et al. |
| 8,524,869 B2 | 9/2013 | Smith et al. |
| 8,642,741 B2 | 2/2014 | Classon et al. |
| 8,715,943 B2 | 5/2014 | Princen et al. |
| 8,728,282 B2 | 5/2014 | Niu |
| 8,728,475 B2 | 5/2014 | Burkly et al. |
| 8,728,482 B2 | 5/2014 | Smith et al. |
| 8,766,034 B2 | 7/2014 | Shih et al. |
| 8,781,750 B2 | 7/2014 | Stuart et al. |
| 8,859,739 B2 | 10/2014 | Kontermann et al. |
| 8,883,975 B2 | 11/2014 | Brandt et al. |
| 8,975,022 B2 | 3/2015 | Begovich et al. |
| 9,017,679 B2 | 4/2015 | Podack et al. |
| 9,068,003 B2 | 6/2015 | Siegel et al. |
| 9,102,733 B2 | 8/2015 | Endl et al. |
| 9,290,576 B2 | 3/2016 | Attinger et al. |
| 9,305,137 B1 | 4/2016 | Targan et al. |
| 9,332,741 B2 | 5/2016 | Shih et al. |
| 9,371,565 B2 | 6/2016 | Begovich et al. |
| 9,416,185 B2 | 8/2016 | Smith et al. |
| 9,465,027 B2 | 10/2016 | Hauenstein et al. |
| 9,499,627 B2 | 11/2016 | Podack et al. |
| 9,556,277 B2 | 1/2017 | Classon et al. |
| 9,580,752 B2 | 2/2017 | Rotter et al. |
| 9,683,998 B2 | 6/2017 | Arch et al. |
| 9,784,748 B2 | 10/2017 | Wang et al. |
| 9,834,606 B2 | 12/2017 | Li et al. |
| 9,839,670 B2 | 12/2017 | Podack et al. |
| 9,896,511 B2 | 2/2018 | Siegel et al. |
| 9,902,996 B2 | 2/2018 | Dubinsky |
| 10,316,083 B2 | 6/2019 | Michelsen et al. |
| 10,322,174 B2 | 6/2019 | Bilsborough et al. |
| 10,626,180 B2 | 4/2020 | McGovern et al. |
| 2001/0006789 A1 | 7/2001 | Maino et al. |
| 2002/0006613 A1 | 1/2002 | Shyjan et al. |
| 2002/0019837 A1 | 2/2002 | Balnaves |
| 2002/0048566 A1 | 4/2002 | El-Deiry et al. |
| 2002/0078757 A1 | 6/2002 | Hines et al. |
| 2002/0106684 A1 | 8/2002 | Kopreski |
| 2002/0150583 A1 | 10/2002 | Gentz et al. |
| 2002/0150939 A1 | 10/2002 | Taylor et al. |
| 2002/0165137 A1 | 11/2002 | Ruben et al. |
| 2002/0198371 A1 | 12/2002 | Wang |
| 2003/0017518 A1 | 1/2003 | Lam et al. |
| 2003/0092019 A1 | 5/2003 | Meyer et al. |
| 2003/0129189 A1 | 7/2003 | Yu et al. |
| 2003/0129215 A1 | 7/2003 | Mollison et al. |

(56) References Cited

U.S. PATENT DOCUMENTS

| | | |
|---|---|---|
| 2003/0138781 A1 | 7/2003 | Whitehead |
| 2003/0148345 A1 | 8/2003 | Kopreski |
| 2003/0166871 A1 | 9/2003 | Barbas et al. |
| 2003/0176409 A1 | 9/2003 | Offner |
| 2003/0198640 A1 | 10/2003 | Yu et al. |
| 2003/0229455 A1 | 12/2003 | Bevilacqua et al. |
| 2004/0009479 A1 | 1/2004 | Wohlgemuth et al. |
| 2004/0013655 A1 | 1/2004 | Shiozawa et al. |
| 2004/0053262 A1 | 3/2004 | Lu |
| 2004/0072154 A1 | 4/2004 | Morris et al. |
| 2004/0123343 A1 | 6/2004 | La et al. |
| 2004/0142325 A1 | 7/2004 | Mintz et al. |
| 2004/0181048 A1 | 9/2004 | Wang |
| 2004/0203076 A1 | 10/2004 | Targan et al. |
| 2004/0213761 A1 | 10/2004 | Bowman et al. |
| 2004/0219555 A1 | 11/2004 | Van Heel |
| 2004/0265864 A1 | 12/2004 | Mitsuhashi |
| 2005/0054021 A1 | 3/2005 | Targan et al. |
| 2005/0143333 A1 | 6/2005 | Richards et al. |
| 2005/0163764 A1 | 7/2005 | Medzhitov et al. |
| 2005/0182007 A1 | 8/2005 | McSwiggen et al. |
| 2005/0228172 A9 | 10/2005 | Wang |
| 2005/0260204 A1 | 11/2005 | Allan |
| 2005/0261219 A1 | 11/2005 | Richards et al. |
| 2006/0003392 A1 | 1/2006 | Oh et al. |
| 2006/0008819 A1 | 1/2006 | Curtis et al. |
| 2006/0067936 A1 | 3/2006 | Benson et al. |
| 2006/0100132 A1 | 5/2006 | Corneliussen et al. |
| 2006/0134663 A1 | 6/2006 | Harkin et al. |
| 2006/0141478 A1 | 6/2006 | Brant et al. |
| 2006/0154276 A1 | 7/2006 | Lois et al. |
| 2006/0193861 A1 | 8/2006 | Gentz et al. |
| 2006/0211020 A1 | 9/2006 | Farrer et al. |
| 2006/0234285 A1 | 10/2006 | Gentz et al. |
| 2007/0015271 A1 | 1/2007 | Rosen et al. |
| 2007/0020268 A1 | 1/2007 | Ashkenazi et al. |
| 2007/0020637 A1 | 1/2007 | Isogai et al. |
| 2007/0032413 A1 | 2/2007 | Rosen et al. |
| 2007/0037165 A1 | 2/2007 | Venter et al. |
| 2007/0054278 A1 | 3/2007 | Cargill |
| 2007/0054282 A1 | 3/2007 | Liew |
| 2007/0059758 A1 | 3/2007 | Levine |
| 2007/0071675 A1 | 3/2007 | Wu et al. |
| 2007/0072180 A1 | 3/2007 | Abreu |
| 2007/0083334 A1 | 4/2007 | Mintz et al. |
| 2007/0161031 A1 | 7/2007 | Trinklein et al. |
| 2007/0196835 A1 | 8/2007 | Bankaitis-Davis et al. |
| 2007/0237770 A1 | 10/2007 | Lai et al. |
| 2007/0254850 A1 | 11/2007 | Lieberman et al. |
| 2007/0275424 A1 | 11/2007 | Gewirtz et al. |
| 2008/0003221 A1 | 1/2008 | Podack et al. |
| 2008/0038746 A1 | 2/2008 | Rosenberg et al. |
| 2008/0038831 A1 | 2/2008 | Benson et al. |
| 2008/0081822 A1 | 4/2008 | Berry et al. |
| 2008/0091471 A1 | 4/2008 | Michon et al. |
| 2008/0095775 A1 | 4/2008 | Lewis et al. |
| 2008/0103180 A1 | 5/2008 | Fleming et al. |
| 2008/0108713 A1 | 5/2008 | Begovich et al. |
| 2008/0131887 A1 | 6/2008 | Stephan et al. |
| 2008/0177048 A1 | 7/2008 | Gagnon |
| 2008/0206762 A1 | 8/2008 | Ferrer et al. |
| 2008/0261207 A1 | 10/2008 | Mitsuhashi |
| 2008/0274467 A1 | 11/2008 | Morris et al. |
| 2008/0293582 A1 | 11/2008 | Li et al. |
| 2009/0018031 A1 | 1/2009 | Trinklein et al. |
| 2009/0048119 A1 | 2/2009 | Krjutskov et al. |
| 2009/0099789 A1 | 4/2009 | Stephan et al. |
| 2009/0162350 A1 | 6/2009 | Abbas et al. |
| 2009/0180380 A1 | 7/2009 | Prabhakar et al. |
| 2009/0186034 A1 | 7/2009 | Abbas et al. |
| 2009/0187005 A1 | 7/2009 | Gagnon |
| 2009/0220417 A1 | 9/2009 | Siadak et al. |
| 2009/0221437 A1 | 9/2009 | Harkin et al. |
| 2009/0226456 A1 | 9/2009 | Gentz et al. |
| 2009/0253133 A1 | 10/2009 | Mitsuhashi et al. |
| 2009/0258848 A1 | 10/2009 | Chakravarti et al. |
| 2009/0297563 A1 | 12/2009 | Borglum et al. |
| 2009/0317388 A1 | 12/2009 | Burkly et al. |
| 2010/0015156 A1 | 1/2010 | Dubinsky et al. |
| 2010/0019016 A1 | 1/2010 | Edoga et al. |
| 2010/0021455 A1 | 1/2010 | Targan et al. |
| 2010/0021917 A1 | 1/2010 | Rotter et al. |
| 2010/0041600 A1 | 2/2010 | Russel et al. |
| 2010/0055700 A1 | 3/2010 | Targan et al. |
| 2010/0099092 A1 | 4/2010 | Song et al. |
| 2010/0105044 A1 | 4/2010 | Fleshner et al. |
| 2010/0136543 A1 | 6/2010 | Georges et al. |
| 2010/0144903 A1 | 6/2010 | Taylor et al. |
| 2010/0184050 A1 | 7/2010 | Rotter et al. |
| 2010/0190162 A1 | 7/2010 | Rotter et al. |
| 2010/0240043 A1 | 9/2010 | Rotter et al. |
| 2010/0240077 A1 | 9/2010 | Targan et al. |
| 2010/0254971 A1 | 10/2010 | Dotan et al. |
| 2010/0266594 A1 | 10/2010 | Reed |
| 2010/0284999 A1 | 11/2010 | Taylor et al. |
| 2010/0291551 A1 | 11/2010 | Belouchi |
| 2010/0298232 A1 | 11/2010 | Liu |
| 2011/0003707 A1 | 1/2011 | Goix et al. |
| 2011/0033486 A1 | 2/2011 | Abbas et al. |
| 2011/0045476 A1 | 2/2011 | Barken et al. |
| 2011/0111418 A1 | 5/2011 | Rhodes et al. |
| 2011/0124644 A1 | 5/2011 | Targan et al. |
| 2011/0136113 A1 | 6/2011 | Uga et al. |
| 2011/0159011 A1 | 6/2011 | Carrier et al. |
| 2011/0160085 A1 | 6/2011 | Li et al. |
| 2011/0177502 A1 | 7/2011 | Hakonarson et al. |
| 2011/0177969 A1 | 7/2011 | Rotter et al. |
| 2011/0189685 A1 | 8/2011 | Taylor et al. |
| 2011/0217310 A1 | 9/2011 | Siegel et al. |
| 2011/0229471 A1 | 9/2011 | Rotter et al. |
| 2011/0243951 A1 | 10/2011 | Podack et al. |
| 2012/0014950 A1 | 1/2012 | Migone et al. |
| 2012/0026371 A1 | 2/2012 | Itano et al. |
| 2012/0041082 A1 | 2/2012 | Rotter et al. |
| 2012/0053131 A1 | 3/2012 | Rotter et al. |
| 2012/0073585 A1 | 3/2012 | Rotter |
| 2012/0079611 A1 | 3/2012 | Shih et al. |
| 2012/0094934 A1 | 4/2012 | Collard et al. |
| 2012/0114654 A1 | 5/2012 | Classon et al. |
| 2012/0135011 A1 | 5/2012 | Podack et al. |
| 2012/0190698 A1 | 7/2012 | Dubinsky et al. |
| 2012/0208900 A1 | 8/2012 | Dubinsky et al. |
| 2012/0263718 A1 | 10/2012 | Siegel et al. |
| 2012/0315282 A1 | 12/2012 | Bedinger et al. |
| 2012/0328559 A1 | 12/2012 | Podack et al. |
| 2013/0012602 A1 | 1/2013 | Haritunians et al. |
| 2013/0012604 A1 | 1/2013 | Rotter et al. |
| 2013/0123117 A1 | 5/2013 | Xu et al. |
| 2013/0129668 A1 | 5/2013 | Firestein et al. |
| 2013/0136720 A1 | 5/2013 | McGovern et al. |
| 2013/0142809 A1 | 6/2013 | Welcher et al. |
| 2013/0216551 A1 | 8/2013 | Begovich et al. |
| 2013/0225439 A1 | 8/2013 | Princen et al. |
| 2013/0344621 A1 | 12/2013 | Wang et al. |
| 2014/0017711 A1 | 1/2014 | Taylor et al. |
| 2014/0018447 A1 | 1/2014 | McGovern et al. |
| 2014/0018448 A1 | 1/2014 | Gonsky |
| 2014/0037618 A1 | 2/2014 | Pidasheva et al. |
| 2014/0141983 A1 | 5/2014 | Singh et al. |
| 2014/0162894 A1 | 6/2014 | Hatchwell et al. |
| 2014/0255302 A1 | 9/2014 | Poulton et al. |
| 2015/0026831 A1 | 1/2015 | Shih et al. |
| 2015/0031972 A1 | 1/2015 | Freeman et al. |
| 2015/0072879 A1 | 3/2015 | Princen et al. |
| 2015/0086567 A1 | 3/2015 | Gonsky et al. |
| 2015/0132311 A1 | 5/2015 | Arch et al. |
| 2015/0259744 A1 | 9/2015 | Begovich et al. |
| 2015/0313904 A1 | 11/2015 | Kolatch et al. |
| 2015/0337378 A1 | 11/2015 | Targan |
| 2015/0376612 A1 | 12/2015 | Lee et al. |
| 2015/0376707 A1 | 12/2015 | Targan |
| 2016/0053007 A1 | 2/2016 | Siegel et al. |
| 2016/0060330 A1 | 3/2016 | Presta |
| 2016/0060335 A1 | 3/2016 | Shih et al. |

(56) References Cited

U.S. PATENT DOCUMENTS

| | | |
|---|---|---|
| 2016/0090629 A1 | 3/2016 | McGovern |
| 2016/0096885 A1 | 4/2016 | Shih et al. |
| 2016/0200833 A1 | 7/2016 | Amann et al. |
| 2016/0208329 A1 | 7/2016 | Targan |
| 2016/0215046 A1 | 7/2016 | Michelsen et al. |
| 2016/0222450 A1 | 8/2016 | Schrodi et al. |
| 2016/0333104 A1 | 11/2016 | Poulton et al. |
| 2017/0044615 A1 | 2/2017 | Rotter et al. |
| 2017/0081400 A1 | 3/2017 | Poulton et al. |
| 2017/0096491 A1 | 4/2017 | Classon et al. |
| 2017/0166967 A1 | 6/2017 | Rotter et al. |
| 2018/0021696 A1 | 1/2018 | Wang et al. |
| 2018/0051078 A1 | 2/2018 | Targan et al. |
| 2018/0052175 A1 | 2/2018 | Arch et al. |
| 2018/0078611 A1 | 3/2018 | Podack et al. |
| 2018/0086840 A1 | 3/2018 | Attinger et al. |
| 2018/0110855 A1 | 4/2018 | Bilsborough et al. |
| 2018/0142302 A1 | 5/2018 | Dubinsky |
| 2018/0156781 A1 | 6/2018 | Shih |
| 2018/0208988 A1 | 7/2018 | Targan et al. |
| 2018/0230543 A1 | 8/2018 | McGovern |
| 2018/0305689 A1 | 10/2018 | Sætrom et al. |
| 2019/0060449 A1 | 2/2019 | Singh et al. |
| 2019/0300957 A1 | 10/2019 | Gonsky et al. |

FOREIGN PATENT DOCUMENTS

| | | |
|---|---|---|
| CA | 2468316 A1 | 6/2003 |
| CA | 2471840 A1 | 7/2003 |
| CA | 2668691 A1 | 6/2008 |
| CA | 2830351 A1 | 10/2012 |
| CA | 2830362 A1 | 10/2012 |
| CA | 2830365 A1 | 10/2012 |
| CA | 2922381 A1 | 3/2015 |
| CL | 2015002866 A1 | 8/2016 |
| CN | 101198624 A | 6/2008 |
| CN | 101903402 A | 12/2010 |
| CN | 202109170 U | 1/2012 |
| CN | 103149371 A | 6/2013 |
| CN | 105246501 A | 1/2016 |
| CN | 105358713 A | 2/2016 |
| CN | 105636648 A | 6/2016 |
| EP | 0760010 B1 | 10/2001 |
| EP | 1285271 B1 | 8/2005 |
| EP | 1716227 A2 | 11/2006 |
| EP | 1243274 B1 | 6/2008 |
| EP | 2005175 A2 | 12/2008 |
| EP | 2034030 A2 | 3/2009 |
| EP | 2064345 A2 | 6/2009 |
| EP | 2097540 A2 | 9/2009 |
| EP | 1819827 B1 | 8/2010 |
| EP | 2270512 A1 | 1/2011 |
| EP | 2565277 A1 | 3/2013 |
| EP | 2689034 A2 | 1/2014 |
| EP | 2689036 A2 | 1/2014 |
| EP | 2689246 A1 | 1/2014 |
| EP | 2978440 A1 | 2/2016 |
| EP | 2996717 A2 | 3/2016 |
| EP | 2997165 A2 | 3/2016 |
| EP | 2462165 B1 | 5/2016 |
| EP | 3022295 A1 | 5/2016 |
| EP | 3041580 A1 | 7/2016 |
| EP | 2638069 B1 | 1/2018 |
| EP | 3270964 A1 | 1/2018 |
| EP | 3294336 A1 | 3/2018 |
| JP | 2005510225 A | 4/2005 |
| JP | 2005514923 A | 5/2005 |
| JP | 2008518610 A | 6/2008 |
| JP | 2009526756 A | 7/2009 |
| JP | 2009195249 A | 9/2009 |
| JP | 2009535016 A | 10/2009 |
| JP | 2010088432 A | 4/2010 |
| JP | 2014515599 A | 7/2014 |
| JP | 2016522164 A | 7/2016 |
| JP | 2016526875 A | 9/2016 |
| JP | 2016536002 A | 11/2016 |
| JP | 2016198116 A | 12/2016 |
| KR | 20150134393 A | 12/2015 |
| KR | 20160009582 A | 1/2016 |
| KR | 20160052585 A | 5/2016 |
| WO | WO-9116928 A1 | 11/1991 |
| WO | WO-9202819 A2 | 2/1992 |
| WO | WO-9222323 A1 | 12/1992 |
| WO | WO-9307485 A1 | 4/1993 |
| WO | WO-9312248 A1 | 6/1993 |
| WO | WO-9404188 A1 | 3/1994 |
| WO | WO-9521941 A1 | 8/1995 |
| WO | WO-9531575 A1 | 11/1995 |
| WO | WO-9614328 A1 | 5/1996 |
| WO | WO-9725445 A1 | 7/1997 |
| WO | WO-9847004 A1 | 10/1998 |
| WO | WO-0066608 A1 | 11/2000 |
| WO | WO-0076492 A1 | 12/2000 |
| WO | WO-0120036 A2 | 3/2001 |
| WO | WO-0142511 A2 | 6/2001 |
| WO | WO-0157182 A2 | 8/2001 |
| WO | WO-0204643 A1 | 1/2002 |
| WO | WO-0157182 A3 | 3/2002 |
| WO | WO-0228999 A2 | 4/2002 |
| WO | WO-03008583 A2 | 1/2003 |
| WO | WO-03025148 A2 | 3/2003 |
| WO | WO-03040404 A1 | 5/2003 |
| WO | WO-03053220 A2 | 7/2003 |
| WO | WO-03057146 A2 | 7/2003 |
| WO | WO-03059333 A2 | 7/2003 |
| WO | WO-03090694 A2 | 11/2003 |
| WO | WO-03099312 A1 | 12/2003 |
| WO | WO-2004020968 A2 | 3/2004 |
| WO | WO-2004031159 A1 | 4/2004 |
| WO | WO-2004035537 A2 | 4/2004 |
| WO | WO-2004048600 A2 | 6/2004 |
| WO | WO-2004050836 A2 | 6/2004 |
| WO | WO-03025148 A3 | 11/2004 |
| WO | WO-2005044792 A2 | 5/2005 |
| WO | WO-2005114469 A1 | 12/2005 |
| WO | WO-2005115115 A2 | 12/2005 |
| WO | WO-2005116251 A1 | 12/2005 |
| WO | WO-2006017173 A1 | 2/2006 |
| WO | WO-2006063093 A2 | 6/2006 |
| WO | WO-2006075254 A2 | 7/2006 |
| WO | WO-2006110091 A1 | 10/2006 |
| WO | WO-2006116721 A1 | 11/2006 |
| WO | WO-2006122079 A1 | 11/2006 |
| WO | WO-2007005608 A2 | 1/2007 |
| WO | WO-2007025989 A2 | 3/2007 |
| WO | WO-2007117611 A2 | 10/2007 |
| WO | WO-2007133816 A2 | 11/2007 |
| WO | WO-2007140625 A1 | 12/2007 |
| WO | WO-2008014400 A2 | 1/2008 |
| WO | WO-2008033239 A2 | 3/2008 |
| WO | WO-2008048902 A2 | 4/2008 |
| WO | WO-2008048984 A2 | 4/2008 |
| WO | WO-2008048986 A2 | 4/2008 |
| WO | WO-2008101133 A2 | 8/2008 |
| WO | WO-2008106451 A2 | 9/2008 |
| WO | WO-2008106579 A2 | 9/2008 |
| WO | WO-2008109782 A2 | 9/2008 |
| WO | WO-2008112990 A2 | 9/2008 |
| WO | WO-2008116150 A2 | 9/2008 |
| WO | WO-2008106451 A3 | 11/2008 |
| WO | WO-2008134569 A2 | 11/2008 |
| WO | WO-2008137762 A2 | 11/2008 |
| WO | WO-2008141148 A2 | 11/2008 |
| WO | WO-2009020403 A1 | 2/2009 |
| WO | WO-2009052512 A2 | 4/2009 |
| WO | WO-2009064854 A2 | 5/2009 |
| WO | WO-2009073628 A2 | 6/2009 |
| WO | WO-2009105590 A2 | 8/2009 |
| WO | WO-2009117122 A2 | 9/2009 |
| WO | WO-2009143278 A2 | 11/2009 |
| WO | WO-2009105590 A3 | 1/2010 |
| WO | WO-2010008858 A1 | 1/2010 |
| WO | WO-2010039931 A2 | 4/2010 |
| WO | WO-2010048415 A1 | 4/2010 |

(56) References Cited

FOREIGN PATENT DOCUMENTS

| | | |
|---|---|---|
| WO | WO-2010056682 A2 | 5/2010 |
| WO | WO-2010062960 A2 | 6/2010 |
| WO | WO-2010075579 A2 | 7/2010 |
| WO | WO-2010075584 A1 | 7/2010 |
| WO | WO-2010083234 A1 | 7/2010 |
| WO | WO-2010118210 A1 | 10/2010 |
| WO | WO-2010120814 A1 | 10/2010 |
| WO | WO-2011017120 A1 | 2/2011 |
| WO | WO-2011088237 A1 | 7/2011 |
| WO | WO-2011088306 A1 | 7/2011 |
| WO | WO-2011088380 A1 | 7/2011 |
| WO | WO-2011116111 A1 | 9/2011 |
| WO | WO-2012054532 A1 | 4/2012 |
| WO | WO-2012064682 A1 | 5/2012 |
| WO | WO-2012135142 A1 | 10/2012 |
| WO | WO-2012135144 A2 | 10/2012 |
| WO | WO-2012135146 A2 | 10/2012 |
| WO | WO-2012154253 A1 | 11/2012 |
| WO | WO-2012161856 A1 | 11/2012 |
| WO | WO-2012174338 A2 | 12/2012 |
| WO | WO-2013012604 A1 | 1/2013 |
| WO | WO-2013059732 A1 | 4/2013 |
| WO | WO-2014106602 A1 | 7/2014 |
| WO | WO-2014160463 A1 | 10/2014 |
| WO | WO-2014160883 A1 | 10/2014 |
| WO | WO-2014186665 A2 | 11/2014 |
| WO | WO-2014186750 A2 | 11/2014 |
| WO | WO-2015010108 A1 | 1/2015 |
| WO | WO-2015035261 A1 | 3/2015 |
| WO | WO-2015168699 A1 | 11/2015 |
| WO | WO-2016149282 A1 | 9/2016 |
| WO | WO-2016186972 A1 | 11/2016 |
| WO | WO-2017077715 A1 | 5/2017 |
| WO | WO-2017106383 A1 | 6/2017 |
| WO | WO-2017161342 A1 | 9/2017 |
| WO | WO-2017196663 A1 | 11/2017 |
| WO | WO-2018081074 A1 | 5/2018 |

OTHER PUBLICATIONS

Abreu et al.: Mutations in NOD2 are associated with fibrostenosing disease in patients with Crohn's disease. Gastroenterology 123:679-688 (2002).
Adam et al.: Immune response in cancer. Pharmacology & Therapeutics 99:113-132 (2003).
Adams et al.: 3400 new expressed sequence tags identify diversity of transcripts in the human brain. Nature Genetics 4:256-267 (1993).
Adams et al.: Two-stage genome-wide methylation profiling in childhood-onset Crohn's Disease implicates epigenetic alterations at the VMP1/MIR21 and HLA loci. Inflamm Bowel Dis. 20(10):1784-1793 (2014).
Adler et al. Anti-tumor necrosis factor [alpha] prevents bowel fibrosis assessed by messenger RNA, histology, and magnetization transfer MRI in rats with Crohn's disease. Inflamm Bowel Dis 19(4):683-690 (2013).
Aggarwal et al. The Role of TNF and its Family Members in Inflammation and Cancer: Lessons from Gene Deletion, CLUT. Drug Targets Inflamm. Allergy, 1(4):327-341,2002.
Ahmad et al. The molecular classification of the clinical manifestations of Crohn's disease. Gasterenterology 122:854-866 (2002).
Ahmad et al.: Clinical relevance of advances in genetics and pharmacogenetics of IBD. Gastroenterology, 126:1533-1549, 2004.
Ahn et al.: The First Korean Genome Sequence and Analysis: Full Genome Sequencing for a Socio-Ethnic Group, Genome Res., 2009, vol. 19, pp. 1622-1629.
Aiba et al.: The role of TL1A and DR3 in autoimmune and inflammatory diseases. Mediators Inflamm. 2013:#258164, 9 pages.
Ajioka et al.: Haplotype analysis of hemochromatosis: evaluation of linkage-disequilibrium approaches and evolution of disease chromosome. Am J Hum Genet 60:1439-1447 (1997).

Akolkar et al.: The IBD1 locus for susceptibility to Crohn's disease has a greater impact on Ashkenazi Jews with early onset diabetes. Am J Gastroentrol 96:1127-1132 (2001).
Al-Lazikani et al.: Standard conformations for the canonical structures of immunoglobulins. J. Molec. Biol. 273:927-948, 1997.
Alvarez-Lobos et al.: Crohn's Disease patients carrying Nod2/CARD15 gene variants have an increased and early need for first surgery due to stricturing disease and higher rate of surgical recurrence. Ann Surg, 242:693-700, 2005.
Ames et al.: Are vitamin and mineral deficiencies a major cancer risk? Nature 694-704 (2002).
An et al.: A tumor necrosis factor a-inducible promoter variant of interferon-g accelerates C04+ T cell depletion in human immunodeficiency virus-1 infected individuals. J Infectious Diseases 188:228-213 (2003).
Ando et al. Triplet repeat polymorphism within the NOTCH4 gene located near the junction of the HLA class II and class III regions in narcolepsy. Tissue Antigens 50:646-649 (1997).
Andus et al.: Measurement of TNFalpha mRNA in a small number of cells by quantitative polymerase chain reaction. (PCR) Regional Immunology 5:11-17 (1993).
Andus et al.: Measurement of TNFalpha mRNA in lamina propia lymphocytes (LPL) isolated from mucosal biopsies by quantitative polymerase chain reaction (PCR). Cytokines and cytokine receptor in mucosal immunity Abstract# 2742 p. A1409 (1992).
Annese et al.: Genetic analysis in Italian families with inflammatory bowel disease supports linkage to the IB01 locus—a GSIC study. Eur J Hum Genet 7:567-573 (1999).
Annese et al.: Variants of CARD15 are associated with an aggressive clinical course of Crohn's disease—an IG-IBD study. American Journal of Gastroenterology 100:84-92 (2005).
Aron et al.: Analysis of hsp70 gene polymorphism in allergic asthma Allergy 54:165-170 (1999).
Babbage, A., Human DNA Sequence from Clone RP11-428F18 on Chromosome 9, Complete Sequence, GenBank: AL390240, Dec. 13, 2012, pp. 1-31.
Badger et al.: Idoxifene, a novel selective estrogen receptor modulator is effective in a rat model of adjuvant-induced arthritis. J Pharmacology and Experimental Therapeutics 291:1380-1386 (1999).
Ballantyne et al.: Short communication, assignment of the gene for intercellular adhesion molecule-1 (ICAM-1) to proximal mouse chromosome 9. Genomics 9:547-550 (1991).
Bamias et a., Expression, localization, and functional activity of TL1A, a novel Th1-polarizing cytokine in inflammatory bowel disease. Journal of Immunology 171(9):4868-4874 (2003).
Bamias et al. Circulating levels of TNF-like cytokine 1A (TL1A) and its decoy receptor 3 (DcR3) in rheumatoid arthritis. Clin Immunol 129:249-255, 2008.
Bamias et al.: Proinflammatory Effects of Th2 Cytokines in a Murine Model of Chronic Small Intestinal Inflammation, Gastroenterol, 128:654-666, 2005.
Bamias et al.: Role of TL1A and its Receptor DR3 in Two Models of Chronic Murine Ileitis, PNAS, 103(22):8441-8446, 2006.
Bao et al.: Molecular mechanism for gender differences in susceptibility to T Cell mediated autoimmune diabetes in nonobese diabetic mice. J of Immunol 168:5269-5379 (2002).
Barrett et al.: Constitutive TL1A Expression under Colitogenic Condition Modulates the Severity and Location of Gut Mucosal Inflammation and Induces Fibrostenosis, American Journal of Pathology, 2012, vol. 180(2), pp. 636-649.
Barrett et al.: Genome-wide association defines more than 30 distinct susceptibility loci for Crohn's disease. Nature Genetics, 40:955-962, 2008.
Barrett et al.: In Vivo constitutive expression of an IBD associated gene TNFSF15 causes severe inflammation and induces fibrostenotic disease in 2 marine models of chronic colitis. Gastroenterology, 140(5):Supplement 1, S-151, Abstract 925, 2011.
Bauer et al.: A genetic enrichment for mutations constructed by oligodeoxynucleotide-directed mutagenesis. Gene, 37:73-81, 1985.
Becker et al.: Clustering of non-major histocompatibility complex susceptibility candidate loci in human autoimmune disease. PNAS USA 95:9979-9984 (1998).

(56) References Cited

OTHER PUBLICATIONS

Benedict et al.: Immunoglobulin Kappa light chain variable region, Partial (Mus musculus). GenBank: AAD39789.1, Jul. 26, 2016, 1 page.
Benoit et al.: Presence of somatostatin-28-(1-12) in hypothalamus and pancreas. PNAS USA 79:917-921 (1982).
Beutler et al.: Control of cachectin (tumor necrosis factor) synthesis: mechanisms of endotoxin resistance. Science 232:977-980 (1986).
Biener-Ramanujan et al.: Functional signaling of membrane-bound TL 1A induces IFNgamma expression. FEBS Lett 11:2376-2380 (2010).
Bioque et al.: Further evidence for a genetic association of interleukin-1 receptor antagonist and ulcerative colitis in the Northern and Mediterranean population. Gastroenterology 108:a783 (1995) Abstract only.
Bird et al.: Single-chain antigen-binding proteins; Science, 242:423-42, 1988.
Boirivant et al.: Hypoproliferative human lamina propia T cells retain the capacity to secrete lymphokines when stimulated via CD2/CD28 pathways. Proceedings of the association of American physicians Abstract Only Proc Assoc Am Physicians 108:55-67 (1996).
Bomprezzi et al.: Gene Expression Profile in Multiple Sclerosis Patients and Healthy Controls: Identifying Pathways Relevant to Disease, Human Molecular Genetics, 12(17):2191-2199, 2003.
Bossuyt et al.: Serologic markers in inflammatory bowel disease. Clinical Chemistry, 52(2):171-181, 2006.
Bourinbaiar et al.: Pregnancy hormones, estrogen and progesteron prevent HIV-1 synthesis in monocytes but not in lymphocytes. FEBS Letters 302:206-208 (1992).
Braasch et al.: Novel Antisense and Peptide Nucleic Acid Strategies for Controlling Gene Expression, Biochemistry, 41(14):4503-4509, 2002.
Brabin. Interactions of the female hormonal environment, susceptibility to viral infection and disease progression. A/OS Patient Care and STDs. 16:211-221 (2002).
Braegger et al.: Tumor necrosis factor alpha in stool as a marker of intestinal inflammation. The Lancet 339:89-91 (1992).
Brambs et al.: Inflammatory Bowel Disease: Radiographical diagnostics, (reprints available at the Department of Radiography, Albert Ludwigs University Hospital, Freiburg, Federal Republic of Germany 3-49 (2009).
Brand, Crohn's Disease: Th1, Th17 or both? The Change of a Paradigm: New Immunological and Genetic Insights implicate Th17 Cells in the Pathogenesis of Crohn's Disease, GUT, 58(8):1152-1167, 2009.
Brant et al.: American families with Crohn's disease have strong evidence for linkage to chromosomes 16 but not chromosome 12. Gastroentrol 115:1056-1061 (1998).
Braun et al.: Chapter 13: Multiparameter analysis of immunogenetic mechanisms in clinical diagnosis and management of inflammatory bowel disease. Immune mechanisms in inflammatory bowel disease edited by Richard S. Blumberg and Markus F. Neurath Mar. 10, 2006, Springer first edition: pp. 209-218.
Bream et al.: A single nucleotide polymorphism in the proximal IFN-gamma promoter alters control of gene transcription. Genes and Immunity 3:165-169 (2002).
Brennan et al. Preparation of bispecific antibodies by chemical recombination of monoclonal immunoglobulin G$\_\{1\}$ fragments. Science 229:81-83, 1985.
Brinar et al.: P217—Genetic Variants in Autophagy Related Genes and Granuloma Formation in Patients with Crohn's Disease, Journal of Crohn's and Colitis, 2009, vol. 3(1), p. S96.
Brummell et al. Probing the combining site of an anti-carbohydrate antibody by saturationmutagenesis: Role of the heavy-chain CDR3 residues. Biochem. 32: 1180-1187, 1993 .
Bull et al.: The death receptor 3-TNF-like protein 1A pathway drives adverse bone pathology in inflammatory arthritis. J.Exp. Med., 205(11):2457-2464, 2008.

Buning et al.: Heterozygosity for IL23R, p.Arg318 Gin confers a protective effect not only against Crohn's disease but also ulcerative colitis. Aliment. Pharmacal Ther. 26:1025-1033 (2007).
Burks et al.: GenBank Nucleic Acids Res (Suppl) 29:2065-2069 (1992).
Burks et al.: In vitro scanning saturation mutagenesis of an antibody binding pocket. Proc. Natl. Acad. Sci. USA 94:412-417, 1997.
Burstein et al.: Atrial fibrosis: mechanisms and clinical relevance in atrial fibrillation. J. Am. College Cardiol., 51(8), 8 pages. 2008.
Bush et al.: Cancer chemoresistance: the relationship between p53 and multidrug transporters Int. J Cancer 98:323-330 (2002).
Calemine et al.: Immunomodulation by diethylstillbestrol is dose and gender related: effects on thymocyte apoptosis and mitogen-induced proliferation. Toxicology 178:101-118 (2002).
Camoglio et al.: Altered expression of interfero-gamma and interleukin-4 in inflammatory bowel disease; Inflamm Bowel Dis., 4(4): 285-290; Abstract only (1998).
Cardullo, et al. Detection of nucleic acid hybridization by nonradiative fluorescence resonance energy transfer. Proc Natl Acad Sci U S A. Dec. 1988;85(23):8790-4.
Casini-Raggi et al.: Mucosal imbalance of IL-1 and IL-1 receptor antagonist in inflammatory bowel disease. J Immunol 154:2434-2440 (1995).
Cavanaugh et al.: Analysis of Australian Crohn's disease pedigrees refines the localization for susceptibility to inflammatory bowel disease on chromosome 16. Ann Hum Genet 62:291-298 (1998).
CBI SNP ID s11209063, 2006, retrieved from: http://www.ncbi.nlm.nih.gov/projects/SNP/snp_ref.cgi?rs=11209063 (3 pgs.).
CBI SNP ID rs12495640, 2006, retrieved from: http://www.ncbi.nlm.nih.gov/projects/SNP/snp_ref.cgi?rs=12495640 (3 pgs.).
CBI SNP ID rs1495964, 2006, retrieved from: http://www.ncbi.nlm.nih.gov/projects/SNP/snp_ref.cgi?rs=1495964 (3 pgs.).
CBI SNP ID rs1908632, 2006, retrieved from: http://www.ncbi.nlm.nih.gov/projects/SNP/snp_ref.cgi?rs=1908632 (3 pgs.).
CBI SNP ID rs6788981, 2006, retrieved from: http://www.ncbi.nlm.nih.gov/projects/SNP/snp_ref.cgi?rs-6788981 (3 pgs.).
CBI SNP ID rs7374667, 2006, retrieved from: http://www.ncbi.nlm.nih.gov/projects/SNP/snp_ref.cgi?rs=7374667 (4 pgs).
Cenci et al.: Estrogen deficiency induces bone loss by increasing T cell proliferation and lifespan through IFN-gamma induced class II transactivator. PNAS USA 100:10405-10410 (2003).
Chaudhary et al.: Prediction of response to infliximab in Crohn's disease. Digestive and Liver Disease 37:559-563 2005.
Chen et al. Screening for genes associated with cardiac fibrosis induced by aldosterone. Xi Bao Yu Fen Zi Mian Yi Xue Za Zhi Journal of Cellular and Molecular Immuno 28(4):350-353 (English Abstract). 2012.
Chen et al.: Discordant protein and mRNA expression in lung adenocarcinomas. Mol. Cell. Proteomics, 4:304-313, 2002.
Chevillard et al. Two new polymorphisms in the human interferon gamma promoter. Eur J Immunogenetics 29:52-56 (2002).
Chiaretti et al.: Gene expression profile of adult T-cell acute lymphocytic leukemia identifies distinct subsets of patients with different responses to therapy and survival. Blood 103:2771-2778 (2004).
Cho et al.: Confirmation of a susceptibility locus for Crohn's disease on chromosome 16. Inflamm Bowel Dis. 3:186-190 (1997).
Cho et al.: Identification of novel susceptibility loci for inflammatory bowel disease on chromosome 1p, 3q and 4q: evidence for epistasis between 1p and IBD1. PNAS USA 95:7502-7507 (1998).
Chu et al.: A genome-wide association study identifies two new risk loci for Graves' disease. Nature Genetics; 43/9:897-901 (2011).
Cippitelli et al. Retinoic acid-induced transcriptional modulation of the human interferongamma promoter. J Biol Chemistry 271:26783-26793 (1996).
Cippitelli et al.: Vitamin D3: a transcriptional modulator of the interferon-gamma gene. Eur J Immunol Abstract Only 28:3017-3030 (1998).
Clarke et al. An anti-TL1A antibody for the treatment of asthma and inflammatory bowel disease. MAbs 10(4):664-677 (2018).
Clunie et al.: Relevance of Thiopurine Methyltransferase Status in Rheumatology Patients Receiving Azathioprine, Rheumatology, 2004, vol. 41(1), pp. 13-18.

(56) References Cited

OTHER PUBLICATIONS

Cooper et al.: Systematic Assessment of Copy Number Variant Detection Via Genome-Wide SNP Genotyping, Nature Genetics, 2008, vol. 40, pp. 1199-1203.
Costello et al.: Dissection of the inflammatory bowel disease transcriptome using genome wide eDNA microarrays. PloS Medicine 2:0771-0787 (2005).
Craik, Charles. Use of oligonucleotides for site-specific mutagenesis. BioTechniques 1985:12-19, 1985.
Curran et al.: Genetic analysis of inflammatory bowel disease in a large European cohort supports linkage to chromosome 12 and 16. Gastroenterology 115:1066-1071 (1998).
Cushman et al.: Effects of estrogen and selective estrogen receptor modulators in hemostasis and inflammation: potential differences among drugs. Annals of New York Academy of Sciences Abstract Only 949:175-180 (2001).
Cushman et al.: Tamoxifen and cardiac risk factors in healthy women—suggestion of an anti-inflammatory effect, arteriosclerosis, thrombosis and vascular biology. Arterioscler Thromb Vasc Biol 21:251-266 (2001).
Cuzzocrea et al.: 17 beta-estradiol anti-inflammatory activity in Carrageenan-induced pleurisy. Endocrinology 141:1455-1463 (2000).
DbSNP Short Genetic Variations. Reference SNP(refSNP) Cluster Report: rs4855535. Printed Sep. 10, 2013, 5 pages, www.ncbi.nlm.nih.gov.
DbSNP, Short Genetic Variations, Submitted SNP(ss) Details: ss70756257,, Apr. 27, 2007, 1 page, https://www.ncbi.nlm.nih.gov.
De Domenico et al.: The Molecular Basis of Ferroportin Linked Hemochromatosis, Proc Natl Acad Sci USA, 2005, vol. 102(25), pp. 8955-8960.
Derrkx et al.: Tumor-necrosis-factor antibody treatment in Crohn's disease. The Lancet 342:173-174 (1993).
Desilva et al.: Pharmacogenetics of infliximab in Crohn's disease: the 5q31/IBD5 risk haplotype predict response. Gastroenterology 122:Abstract M1423 (2002).
Devlin et al.: NOD2 variants and antibody response to microbial antigens in Crohn's disease patients and their unaffected relatives. Gastroenterology 132:576-586 (2007).
Devlin et al.: NOD2 variants are significantly associated with sero-reactivity to microbial antigens in Crohn's disease. AGA Institute Digestive Disease Week, Abstract #442 Only (2006).
Diamond et al.: Binding of the integrin Mac-1 (CD11 b/CD18) to the third immunoglobulin-like domain of ICAM01 (CD54) and its regulation by glycosylation. Cell 65:961-971 (1991).
Diamond et al.: ICAM-1 (CD54): A counter receptor for Mac-1 (CD11b/CD18). J Cell Blol.111:3129-3139 (1990).
Diaz-Gallo et al. Differential association of two PTPN22 coding variants with Crohn's disease and ulcerative colitis. Inflammatory Bowel Diseases, vol. 17, No. 11, pp. 2287-2294, 2011.
Dib et al.: A comprehensive genetic map of the human based on 5,264 microsatellites. Nature 380:152-154 (1996).
Drach et al.: Interphase Fluorescence in Situ Hybridization Identifies Chromosomal Abnormalities in Plasma Cells from Patients with Monoclonal Gammopathy of Undetermined Significance, Blood, 1995, vol. 86, pp. 3915-3921.
Dubinsky et al.: CARD8: A novel association with childhood onset ulcerative colitis (UC). AGA Institute Abstract# T1983 p. A-587 (2006).
Dubinsky et al.: Familial expression of serological immune responses in pediatric IBD. J of Pediatric Gastroenterology and Nutrition Abstract #150 41:539 (2005).
Dubinsky et al.: IL-23 receptor (IL-23R) gene protects against pediatric Crohn's disease. Inflamm Bowel Disease 13:511-515 (2007).
Dubinsky et al.: Serum immune responses predict rapid disease progression among children with Crohn's disease: immune responses predict disease progression. Am J. Gastroenterology 101:360-367 (2006).
Dubinsky et al.: Synergism of NOD2 and ASCA (Anti-Saccharomyces Cerevisiae Antibodies) Contributes to Disease Behavior in Pediatric Crohn's Disease (CD) Patients, Gastroenterology, 2003, vol. 124, pp. M1556.
Duerr et al.: A Genome-wide association study identifies IL23R as an inflammatory bowel disease gene. Science, 314:1461-1463, 2006.
Duerr et al.: Association between ulcerative colitis and a polymorphism in intron 2 of the interleukin-2 receptor antagonist gene. Gastroenterology Abstract Only 108:a812 (1995).
Duerr et al.: Homozygosity for an HLA class II group haplotype is associated with pANCA positive and familial ulcerative colitis. Abstract only Gastroenterology 108:a812 (1995).
Duerr et al.: Linkage and association between inflammatory bowel disease and a locus on chromosome 12. Am J Hum Genet 63:95-100 (1998).
Elgert, K., Immunology: Understanding the immune system. Wiley-Liss: New York, 1996, p. 323.
EP 12762965.7 Extended European Search Report dated Mar. 24, 2015.
EP 12764214.8 Extended European Search Report dated Nov. 18, 2014.
EP 12765854 Extended European Search Report dated Mar. 18, 2015.
EP 12765854.0 Partial Supplementary Search Report dated Nov. 24, 2014.
EP 12762965.7 Partial Supplementary Search Report dated Nov. 26, 2014.
Erlandsson et al.: Effects of raloxifene, a selective estrogen receptor modulator on thymus T cell reactivity and inflammation in mice. Cellular Immunology 205:103-109 (2000).
Erlich et al.: Chapter 32: HLA DNA typing. PCR protocols. Edited by Innis et al. pp. 261-271 (1990).
Erpenbeck et al. Segmental allergen challenge in patients with atopic asthma leads to increased IL-9 expression in bronchoalveolar lavage fluid lymphocytes. J Allergy Clin Immunol 111(6):1319-1327, 2003.
European Patent Application No. 05853294 European Search Report dated Apr. 29, 2008.
European Patent Application No. 05853294 Further Examination Report dated Apr. 30, 2009.
European Patent Application No. 05853294 Office Action dated May 15, 2008.
European Patent Application No. 06772657 ESR dated Dec. 2, 2008.
European Patent Application No. 10171757 European Search Report dated Nov. 10, 2010.
European Patent Application No. 14773989 Extended European Search Report dated Dec. 19, 2016, 10 pages.
European Patent Application No. 14773989.0 Communication dated Nov. 17, 2017.
European Patent Application No. 14773989.0 Office Action dated Aug. 10, 2018.
European Patent Application No. 14797214 Extended European Search Report dated Feb. 3, 2017, 15 pages.
European Patent Application No. 14797214 Partial European Search Report dated Oct. 28, 2016, 9 pages.
European Patent Application No. 14797214.5 Office Action dated Apr. 19, 2018.
European Patent Application No. 14798650 Extended European Search Report dated Oct. 21, 2016, 12 pages.
European Patent Application No. 14798650.9 Communication dated Jan. 10, 2018.
European Patent Application No. 14826746 Extended European Search Report dated Feb. 1, 2017, 12 pages.
European Patent Application No. 14826746.1 Communication dated Dec. 8, 2017.
European Patent Application No. 14826746.1 Examination Report dated Mar. 13, 2019.
European Patent Application No. 14842590 Extended European Search Report dated Apr. 4, 2017, 10 pages.
European Patent Application No. 14842590 Partial European Search Report dated Jan. 18, 2017, 7 pages.

(56) References Cited

OTHER PUBLICATIONS

European Patent Application No. 17767679.8 Supplementary European Search Report dated Jul. 22, 2019.
European Patent Application No. 18201967.9 European Search Report dated Mar. 6, 2019.
European Patent Application No. 95921264.8 Communication dated Feb. 24, 1999.
European Patent Application No. 95921264.8 Communication dated Feb. 29, 2000.
Ewens et al.: The transmission/disequilibrium test: history, subdivision, and admixture. Am J Hum Genetics 57:455-464 (1995).
Fang et al.: Essential role of TNF receptor superfamily 25 (TNFRS25) in the development of allergic lung inflammation. J.Exp. Med., 205(5):1037-1048, 2008.
Fawcett et al.: Molecular cloning of ICAM-3, a third ligand for LFA-1, constitutively expressed on resting leukocytes. Nature 360:481-4. (1992).
Feder et al.: A novel MHC class 1-like gene is mutated in patients with hereditary heaemochromatosis. Nature Genetics 13:399-408 (1996).
Ferguson et al.: IL23R and IL12B SNPs and haplotypes strongly associate with Crohn's disease risk in a New Zealand population. Gastroenterology Research and Practice, 2010:12 pages, 2010.
Ferrante et al.: Predictors of early response to infliximab in patients with ulcerative colitis. Inflamm Bowel Disease 13:123-128 (2007).
Ferraris et al.: Analysis of CARD15 gene variants in Italian pediatric patients with inflammatory bowel disease. J of Pediatrics 147:272-273 (2005).
Fessler et al.: A genomic and proteomic analysis of activation of the human neutrophil by Lipopolysaccharide and its mediation by p38 mitogen-activated protein kinase. The Journal of Biological Chemistry, 277(35):31291-31302, 2002.
Fitzpatrick, LR, Novel Pharmacological Approaches for Inflammatory Bowl Disease: Targeting Key Intracellular Pathways and the IL-23/IL-17 Axis, International Journal of Inflammation, vol. 2012, pp. 1-8.
Flores et al. In vitro evaluation of the effects of candidate immunosuppressive drugs: flow cytometry and quantitative real-time PCR as two independent and correlated read-outs. Journal of Immunological Methods 289:123-135 (2004).
Forcione et al.: Anti-Saccharomyces cerevisiae antibody (ASCA) positivity is associated with increased risk for early surgery in Crohn's disease. GUT, 53:1117-1122, 2004.
Fox et al.: Estrogen regulates the IFN-gamma promoter. J Immunol 146:4362-4367 (1991).
Franke et al.: Genome-Wide Meta-Analysis Increases to 71 the Number of Confirmed Crohn's Disease Susceptibility Loci, Nature Genetics, 2010, vol. 42(12), pp. 1118-1125.
Fransen et al.: Inflammatory bowel disease: the genetic background and beyond. University of Groningen PhD Dissertation http://www.rug.nl/research/portal/files/12805965/Complete_dissertation.pdf (2014).
Fujikado et al.: Identification of arthritis related gene clusters by microarray analysis analysis of two independent mouse models for rheumatoid arthritis. Arthritis Research and Therapy 8:1-13 (2006).
Fujino et al.: Increased expression of interleukin 17 in inflammatory bowel disease gene. Gut 52:65-70 (2003).
Funke et al.: Functional characterisation of decoy receptors in Crohn's disease; Gut 58(40):483-491 (2009).
Garcia-Bates et al.: GeneBank NM_001198.3, Homo sapiens PR Domain Containing 1, with ZNF Domain (PRDM1), Transcript Variant 1, mRNA, 2010 retrieved from: http://www.ncbi.nlm.nih.gov/nuccore/172072683?sat=13&satkey=10378402 on Jul. 7, 2011.
Garcia-Bates et al.: Peroxisome proliferator-activated receptor gamma ligands enhance human B cell antibody production and differentiation. J Immunology 183:6903-6912 (2009).
Gasche et al.: A simple classification of Crohn's disease: report of the working party for the world congresses of gastroenterology, Vienna. Inflammatory Bowel Disease 6:8-15 (2000).
GenBank Accession No. AF134726 (72 pgs.) (Mar. 27, 1999).
GenBank Accession No. AC007728 (31 pgs.) (Jun. 1, 2001).
GenBank Accession No. AF129756.1 (70 pgs.) (revised Nov. 12, 1999).
GenBank Accession No. AF385089 (3 pgs.) (Jul. 4, 2001).
GenBank Accession No. AF513860 (12 pgs.) Jul. 9, 2002).
GenBank Accession No. AX259776 (21 pgs.) (Oct. 26, 2001).
GenBank Accession No. NM022162 (5 pgs.) (Sep. 11, 2011).
GenBank Accession No. U89335 (25 pgs.) (Oct. 22, 1999).
GenBank Accession No. U89336 (27 pgs.) (Feb. 14, 1997).
GenBank AF252829.4 (49 pgs.) (Nov. 8, 2002).
Gene Card for 1L12B(p. 40) (http://www.genecards.org/cgi-bin/carddisp.pl?gene=1L12B&keywords=i112b) accessed May 8, 2017.
Gene Card for IL17RD retrieved from: http://www.genecards.org/cgi-bin/carddisp.pl?gene=1L17RD&dearch=i117rd (Accessed May 2013).
GeneBank Accession No. AF450133 (10 pgs.) (Dec. 27, 2001).
GeneCard DR3 retrieved from: http://www.genecards.org/cgi-bin/carddisp.pl?gene=TNFRSF25&search=DR3 on Apr. 3, 2018; 16 pages.
GeneCard NOD2 gene (16 pgs) (Last update Jul. 2, 2009).
GeneCards for JAK2 retrieved from: http://www.genecards.org/cgi-bin/carddisp.pl?gene=JAK2&search=jak2 on Oct. 25, 2019.
GeneCards, BRWD1 Gene-GeneCards | BRWD1 Protein | BRWD1 Antibody. Printed Sep. 10, 2013, 11 pages. www.genecards.org.
Gewirtz et al.: Dominant-negative TLR5 polymorphism reduces adaptive immune response to flagellin and negatively associates with Crohn's disease. Am J Physiol Gastrointest Liver Physiol. 290:G1157-G1163 (2006).
Ghosh et al.: Anti-TNF therapy in Crohn's disease Novartis Foundation Symposium 263:193-218 (2004).
Ghosh et al.: Natalizumab for active Crohn's disease. The New England Journal of Medicine, 348:24-32, 2003.
Giacomelli et al.: Combination therapy with cyclosporin and methotrexate in patients with early rheumatoid arthritis soon inhibits TNF production without decreasing TNF mRNA level: an in vivo and in vitro study. Clinical and Experimental Rheumatology 20:365-372 (2002).
Gianfrancesco et al.: Identification of a Novel Gene and a Common Variant Associated with Uric Acid Nephrolithiasis in a Sardinian Genetic Isolate, Am. J. Hum. Genet., 2003, vol. 72, pp. 1479-1491.
Gilmore et al.: Effect of estradiol on cytokine secretion by proteolipid protein-specific T cell clones isolated from multiple sclerosis patients and normal control subjects. Journal of Immunology. Abstract only.158:446-451 (1997).
Gonsky et al.: CD2 mediates activation of the IFN-gamma intronic STAT binding region in mucosal T cells. Eur J Immunol 33:1152-1162 (2003).
Gonsky et al.: Distinct Methylation of IFNG in the Gut, Journal of Interferon and Cytokine Research, 2009, vol. 29(7), pp. 407-414.
Gonsky et al.: Mucosa-specific targets for regulation of IFN-gamma expression: lamia propia cells use different cis-elements than peripheral blood T cells to regulate transactivation of IFN-gamma expression. J Immunol 164:1399-1407 2000.
Goswami et al.: A Brief History of IL-9; The Journal of Immunology; 186; 3283-3288 (2019).
Gout et al.: Death receptor-3, a new e-selectin counter-receptor that confers migration and survival advantages to colon carcinoma cells by triggering p38 and ERK MAPK activation. Cancer Research, 66(18):9117-9124, 2006.
Greenstein et al.: Perforating and non-perforating indications for repeated operation in Crohn's disease: evidence of two clinical forms. Gut 29:588-592 (1988).
Haertel et al.: Dose-dependent immunomodulatory effects of acetylsalicylic acid and indomethacin in human whole blood: potential role of cyclooxygenase-2 inhibition. Scandanavian Journal Immunology 60:412-420 (2004).
Hampe et al.: A genomewide analysis provides evidence for novel linkage in inflammatory bowel disease in a large European cohort. Am J Hum Genet 64:808-816 (1999).
Hampe et al.: A genome-wide association scan of nonsynonymous SNPs identifies a susceptibility variant for Crohn's disease in ATG16L1 Nature Genetics 39:207-211 (2007).

(56) References Cited

OTHER PUBLICATIONS

Hampe et al.: Association between insertion mutation in NOD2 gene and Crohn's disease in German and British populations. Lancet 357:1925-1928 (2001).
Hampe et al.: Association of NOD2 (CARD15) genotype with clinical course of Crohn's disease: a cohort study. Lancet 359:1661-1665 (2002).
Hanifi et al.: Genetic structure of IDDM1: two separate regions in the major histocompatibility complex contribute to susceptibility or protection. Diabetes A Journal of the American Diabetes Association 47:1-7 (1999).
Haritunians et al.: Genetic Predictors of Medically Refractory Ulcerative Colitis, Inflamm Bowel Dis., 2010, vol. 16 ;11), pp. 1830-1840.
Harnish et al. Beneficial effects of estrogen treatment in the HLA-B27 transgenic rat model of inflammatory bowel disease. Am J Physiol Gastrointest Liver Physiology 286:G118-124 (2004).
Hartel et al.: Delayed cytokine mRNA expression kinetics after T-lymphocyte costimulation: A quantitative measure of the efficacy of cyclosporin A-based immunosuppression. Clinical Chemistry 48:2225-2231 (2002).
Hazra et al.: Common variant of FUT2 are associated with plasma vitamin B12levels. Nature Genetics 40:1160-1162 (2008).
Hegele, A., SNP Judgments and Freedom of Association, Arteriosclerosis, Thrombosis, and Vascular Biology, 2002, vol. 22, pp. 1058-1061.
Herbon et al. High-resolution SNP scan of chromosome 6p21 in pooled samples from patients with complex diseases. Genomics 81:510-518 (2003).
Heresbach et al.: NOD2/CARD15 gene polymorphisms in Crohn's disease: a genotype-phenotype analysis. Eur J Gastroenterology and Hepatology 16:55-62 (2004).
Hess et al.: The hydroxylamine of sulfamethoxazole synergizes with FK506 and cyclosporin A inhibiting T-cell proliferation. Journal of Pharmacology and Experimental Techniques. 281:540-548 (1996).
Heusch et al.: IL-9 exacerbates colitis induced by CD4+ CD45RBhigh T cells transfer, via directed activation of in vivo antigen-experienced T cells. Cytokine 56:PS1-056, p. 31 (2011).
Hirano et al.: Association Study of 71 European Crohn's Disease Susceptibility Loci in a Japanese Population, Inflammatory Bowel Diseases, 19(3):526-533, 2013.
Hirschhorn et al.: A comprehensive review of genetic association studies. Genetics in Medicine, 4(2):45-61,2002.
Hlavaty et al.: Polymorphisms in apoptosis genes predict response to infliximab therapy in luminal and fistulizing Crohn's disease. Aliment Pharmacol Ther 22:613-626 2005.
Hodgson, John. Making monoclonals in microbes. Bio/Technology 9:421-425, 1991.
Hogg et al.: Adhesion molecules in cell interactions. Curr Opin Immunol. 5:383-390 (1993).
Hoh et al.: Trimming, Weighting and Grouping SNPs in Human Case-Control Association Studies, Genome Research, 2001, vol. 1, pp. 2115-2119.
Holliger and Hudson. Engineered antibody fragments and the rise of single domains. Nat. Biotechnol. 23(9):1126-36, 2005 .
Honkanen et al.: Coxsackievirus up-regulates IL-17 immunity in human type 1 diabetes. Diabetologia, 54:Supp. 1, S1, Abstract S421, 2009.
Hornquist et al.: G(alpha) 1 2-Deficient Mice with Colitis Exhibit a Local Increase in Memory CD4+ T Cells and Promflammatmy TH1-Type Cytokines, J Immunol, 158:1068-1077, 1997.
Houdebine et al.: Production of Pharmaceutical Proteins from Transgenic Animals, J Biotech, 34 (1994): 269-287.
Hsu et al. The tale of TL1A in inflammation. Mucosal Immunol 4(4):368-370, 2011.
Hsu et al.: Attenuation of TH1 Response in Decoy Receptors Transgenic Mice, J. Immunol, 175:5135-5145, 2005.
Hugot et al.: Association of Nod2 leucine-rich repeat variants with susceptibility to Crohn's disease. Nature 411:599-603 (2001).
Hugot et al.: Linkage analyses of chromosome 6 loci, including HLA, in familial C255 aggregations of Crohn's disease GEG AID. Am J Med Genet 52:207-213 (1994).
Hugot et al.: Mapping of a susceptibility locus for Crohn's disease on chromosome 16. Nature 379:821-823 (1996).
Hundorean et al.: Functional relevance of T helper 17 (Th17) cells and the IL-17 cytokine family in inflammatory bowel disease. Inflammatory Bowel Disease 18:180-186 (2012).
Huse et al. Generation of a large combinatorial library of the immunoglobulin repertoire in phage lambda. Science 246:1275-1281, 1989.
Huston et al. Protein engineering of antibody binding sites: Recovery of specific activity in an anti-digoxin single-chain Fv analogue produced in *Escherichia coli*. Proc. Natl. Acad. Sci. USA 85:5879-5883, 1988.
Ilumina Press Release dated Jan. 12, 2006, retrieved from: http://investor.illumina.com/phoenix.zhtml?=121278.
Inohara et al.: Human NOD1 confers responsiveness to bacterial lipopolysaccharides. J Biol Chem 276:2551-2554 (2001).
Ioannidis et al.: Replication validity of genetic association studies Nature Genetics 29:306-309 (2001).
Ioannidis, J., Why Most Published Research Findings are False, PLoS Med, 2005, vol. 2(8):e124, pp. 0696-0701.
Ippoliti et al.: Combination of innate and adaptive immune alterations increased the likelihood of fibrostenosis in Crohn's disease. Inflamm Bowel Disease 16:1279-1285 (2010).
Ippoliti et al.: The relationship between abnormal innate and adaptive immune function and fibrostenosis in Crohn's disease patients. Abstract only. (2006) Journal unknown.
IRIS et al.: Dense Alu clustering and a potential new member of the NFkB family within a 90 kilo base HLA Class III segment. Nature Genetics 3:137-145 (1993).
Israeli et al.: Anti-Saccharomyces Cerevisiaeand Antineutrophil Cytoplasmic Antibodies as Predictors of Inflammatory Bowel Disease, Gut, 2005, vol. 54(9), pp. 1232-1236.
Jacob et al.: Definition of microsatellite size variants for Tnfa and Hsp70 in autoimmune and nonautoimmune mouse strains. Immunogenetics 36:182-188 (1992).
Jarjour et al.: The 8.5 kb PstI allele of the stress protein gene Hsp70-2: An independent risk factor for systemic lupus erythematosus in African Americans. Hum Immunol 45:59-63 (1996).
Jikihara et al.: Interferon-y Inhibits the Synthesis and Release of Renin from Human Decidual Cells, Biology of Reproduction, 54:1311-1316, 1996.
Johnston et al. Present status and future prospects for HIV therapies. Science 260:1286-1293 (1993).
Jones et al. Replacing the complementarity-determining regions in a human antibody with those from a mouse. Nature 321:522-525, 1986 .
Jongeneel et al.: Extensive genetic polymorphism in the human tumor necrosis factor region and relation to extended HLA haplotypes. PNAS USA 88:9717-9721 (1991).
Jostins et al.: Host-microbe interactions have shaped the genetic architecture of inflammatory bowel disease. Nature; 491/7422:119-124 (2012).
Juhasz et al.: Quantification of chemotherapeutic target gene mRNA expression in human breast cancer biopsies: comparison of real-time reverse transcription-PeR vs. relative quantification reverse transcription-PeR utilizing DNA sequence analysis of PCR product. Journal of Clinical Laboratory Analysis 17:184-194 (2003).
Jung et al.: Genotype/Phenotype analyses for 53 Crohn's disease associated genetic polymorphisms. PLOS/One, 7(12):e52223, 2012.
Juppner, H. Functional properties of the PTH/PTHrP receptor. Bone, 17(2):39S-42S, 1995.
Kakuta et al.: Su1746 Rare Variants of TNFSF15 Are Significantly Associated With Crohn's Disease in Non-Jewish Caucasian Independent of the Known Common Susceptibility SNPs, Gastroenterology, 144(5): S-466, 2013.
Karpuzoglu-Sahin et al.: Effects of long-term estrogen treatment on IFN-gamma, IL-2 and IL 4 gene expression and protein synthesis in spleen and thymus of normal C57BL/6 mice. Cytokine 14:208-217 (2001).

(56) References Cited

OTHER PUBLICATIONS

Karpuzoglu-Sahin et al.: Interferon-gamma levels are upregulated by 17-beta-estradiol and diethylstibestrol. J Reproductive Immunology 52:113-127 (2001).
Kasperkovitz et al.: Activation of the STAT1 Pathway in Rheumatoid Arthritis, Ann Rheum Dis, . 63:233-239, 2004.
Kasvosve et al.: Effect of Ferroportin Q248H Polymorphism on Iron Status in African Children, Am J Clin Nutr, 2005, vol. 82(5), pp. 1102-1106.
Kim et al. DQCAR113and DQCAR115 in combination with HLA-DRB1 alleles are significant markers of susceptibility to rheumatoid arthritis in the Korean population. Tissue Antigens 54:552-559 (1999).
Kim et al. Effects of IL-9 blockade on chronic airway inflammation of murine asthma models. Allergy: Eur J Allergy Clin Immunol Suppl 96(67):448, Nov. 2012.
Kim et al. Effects of interleukin-9 blockade on chronic airway inflammation in murine asthma models. Allergy Asthma Immunol Res 5(4):197-206, 2013.
Kirchhausen et al.: Location of the domains of ICAM-1 by immunolabeling and single-molecule electron microscopy. J. Leukocyte Biology 53:342-346 (1993).
Kita et al.: Sequence and expression of rat ICAM-1. Biochim Biophys Acta 1131:108-111 (1992).
Kite et al.: Use of in vivo-generated biofilms from hemodialysis catheters to test the efficacy of a novel antimicrobial catheter lock for biofilm eradication in vitro. J Clin Microbiol., 42.7 (2004):3073-3076.
Klein et al.: Ex-vivo assessment of candidate anti-inflammatory agents in the treatment of Gram-negative sepsis. Immunology and Infectious Disease 4:33-35 (1994).
Kobayashi et al. Tryptophan H33 plays an important role in pyrimidine (6-4) pyrimidone photoproduct binding by a high-affinity antibody. Protein Eng. 12(10):879-884, 1999.
Koga et al.: Transanal Delivery of Angiotensin Converting Enzyme Inhibitor Prevents Colonic Fibrosis in a Mouse Colitis Model: Development of a Unique Mode of Treatment, Surgery, 144(2):259-268, 2008.
Kohler and Milstein, Derivation of specific antibody-producing tissue culture and tumor lines by cell fusion. Eur. J. Immunol. 6: 511-519, 1976 .
Koutroubakis et al.: Tumor necrosis factor-alpha polymorphism in inflammatory bowel disease. Hellenic J of Gastroenterology 8:132-135 (1995).
Kugathansan et al.: L 1007FsinsC variant of CARD15/NOD2 is strongly associated with early onset and fibrostenosing behavior in pediatric Crohn's disease. Gasteroenterology 126(4 Supp 2):A68 524 (2004).
Kugathansan et al.: Loci on 20q13 and 21q22 are associated with pediatric onset inflammatory bowel disease. Nature Genetics 40:1211-1215 (2008).
Kutyavin et al.: Oligonucleotides with conjugated dihyropyrroloindole tripeptides: base composition and backbone effects on hybridization. Nucleic Acid Res 25:3718-3723 (1997).
Kutyavin, et al. 3'-Minor groove binder-DNA probes increase sequence specificity at PCR extension temperatures. Nucleic Acids Research, 28(2):655-661 (2000).
Lakatos et al.: NOD2/CARD15 mutations and genotype-phenotype correlations in patients with Crohn's disease. Hungarian multicenter study. Orvosi Hetilap 145:1403-1411 (2004).
Lal et al.: Antibiotic Therapy for Crohn's Disease: A Review, Canadian Journal of Gastroenterology, 2006, vol. 20(10), pp. 651-655.
Landegren et al. A Ligase-Mediated Gene Detection Technique. Science 241:1077-1080 (1988).
Lasky. Selectins: interpreters of cell-specific carbohydrate information during inflammation. Science 258:964-969 (1992).
Latham et al.: Estradiol treatment redirects the isotype of the autoantibody response and prevents the development of autoimmune arthritis. J of Immunol 171:5820-5827 (2003).
Laurence et al. Effect of tamoxifen on regulation of viral replication and human immunodeficiency virus (HIV) long terminal repeat-directed transcription in cells chronically infected with HIV-1. Blood 75:696-703 (1990).
Lawrance et al.: Ulcerative Colitis and Crohn's Disease: Distinctive Gene Expression Profiles and Novel Susceptibility Candidate Genes, Human Molecular Genetics, 10(5):pp. 445-456, 2001.
Lee et al.: Estrogen-mediated protection against HIV Tat protein-induced inflammatory pathways in human vascular endothelial cells. Cardiovascular Research 63:139-148 (2004).
Lemna et al.: Mutation analysis for heterozygote detection and the prenatal diagnosis of cystic fibrosis. N. Eng. J. Med. 322:291-296 (1990).
Leong et al.: NOD2/CARD15 gene polymorphisms and Crohn's disease in the Chinese population. Aliment Pharmacol Thera 17:1465-1470 (2003).
Leppkes et al.: RORy-expressing Th17 cells induce murine chronic intestinal inflammation via redundant effects of IL-17A and IL-17F. Gastroenterology, 136:257-267, 2009.
Lesage et al.: CARD15/NOD2 mutational analysis and genotype-phenotype correlation in 612 patients with inflammatory bowel disease. Am J of Human Genetics 70:845-857 (2002).
Leung et al. Expression profiling identifies chemokine (C-C Motif) ligand 18 as an independent prognostic indicator of gastric cancer. Gastroenterology 127:457-469 (2004).
Levy-Coffman, Ellen, A Mosiac of People: The Jewish Story and a Reassessment of the DNA Evidence, Journal of Genetic Genealogy, 1:12-33, 2005.
Li et al. TNFRSF1B is Associated with ANCA in IBD. Inflammatory Bowel Diseases. 22(6):1346-1352 (2016).
Li et al.: Cloning, characterization and the complete 56.8-kilobase DNA sequence of the human NOTCH4 gene. Genomics 51:45-58 (1998).
Li et al.: New serological biomarkers of inflammatory bowel disease. World J of Gastroenterology14:5115-5124 (2008).
Limbergen et al.: IL23R Arg381 Gin is associated with childhood onset inflammatory bowel disease in Scotland. Gut 56:1173-1174 (2007).
Lindner et al. Tamoxifen enhances interferon regulated gene expression in breast cancer cells. Molecular and Cellular Biochemistry 167:169-177 (1997).
Lipsky, P. Structure, function and regulation of molecules involved in leukocyte adhesion. New York: Springer-Verlag 1993 Book not included.
Liu et al.: Mucosal gene expression profiles following the colonization of immunocompetent defined-flora C3H mice with Helicobacter bilis: a prelude to typhlocolitis. Microbes and Infection 11:374-383 (2009).
Livak. Allelic discrimination using fluorogenic probes and the 5' nuclease assay. Genetic Analysis 14:143-149 (1999).
Lodes et al.: Bacterial flagellin is a dominant antigen in Crohn disease. Journal of Clinical Investigation 113:1296-1306 (2004).
Lorenz-Meyer. Inflammatory Bowel Disease Laboratory Diagnostics. (Reprints available from the City Hospital, Friedrichshafen, Federal Republic of Germany):3-29 (2008).
Louis et al. Association between polymorphism in IgG Fe receptor lila coding gene and biological response to infliximab in Crohn's disease. Aliment Pharmacol Ther 19:511-519 (2004).
Low et al.: High-Throughout Genomic Technology in Research and Clinical Management of Breast Cancer, Evolving Landscape of Genetic Epidemiological Studies, Breast Cancer Research, 8(3):209-214, 2006.
Lucentini, J. Gene association studies typically wrong. Scientist, 18(24):20, 2004.
MacDonald et al.: Tumor necrosis factor-alpha and interferon-gamma production measured at the single cell level in normal and inflamed human intestine Clin Exp Immunol 81:301-305 (1990).
Maggio-Price et al.: Helicobacter Infection is Required for Inflammation and Colon Cancer in Smad3-Deficient Mice, Cancer Research, 2006, vol. 66, pp. 828-838.
Maniatis, et al. Molecular Cloning. Cold Spring Harbor Laboratory, 1982.

(56) References Cited

OTHER PUBLICATIONS

Mansfield et al.: Novel genetic association between ulcerative colitis and the antiinflammatory cytokine interleukin-1 receptor antagonist. Gastroenterology 106:637-642 (1994).
Marrakchi et al.: Interleukin 10 promoter region polymorphisms in inflammatory bowel disease in Tunisian population. Inflamm. Res., 58:155-160, 2009.
Martin et al.: Recombination rates across the HLA complex: use of microsatellites as a rapid screen for recombinant chromosome. Human Molecular Genetics 4:423-428 (1995).
Martinez et al.: Regulation and Function of Proinflammatory TH17 Cells, Animals of the New York Academy of Sciences, 1143(1):188-211, 2008.
Martins et al.: Transcriptional repressor Blimp-1 regulates T cell homeostasis and function. Nature Immunology 7:457-265 (2006).
Mascheretti et al. Pharmacogenetic investigation of the TNF/TNF-receptor system in patients with Chronic active Crohn's disease treated with infliximib. The Pharmacogenomics Journal 2:127-136 (2002).
Matalka. The effect of estradiol but not progesterone on the production of cytokines in stimulated whole blood is concentration-dependent. Neuro Endocrinology Letters. Abstract only. 24:185-191 (2003).
Matejuk et al.: 17-beta-estradiol inhibits cytokine, chemokine and chemokine receptor mRNA expression in the central nervous system of female mice with experimental autoimmune encephalomyelitis. J of Neuroscience Research 65:529-542 (2001).
Matsunaga et al.: Application of differential display to identify genes for lung cancer detection in peripheral blood. Int J of Cancer 100:592-599 (2002).
McCall et al.: Constitutive expression of TNF-a and of an IL-8 gene is associated with genetic susceptibility to chronic granulomatous enterocolitis in inbred rats. AGA Abstracts p. A740 (1993).
McEver Leukocyte—endothelial cell interactions. Curr Opin Cell Bioi 4:840-849 (1992).
McGovern et al.: Genetic epistasis of IL23/IL 17 pathway genes in Crohn's disease. Inflamm Bowel Dis. 15:883-889 (2009).
McGovern et al.: Genetics of inflammatory bowel diseases. Gastroenterology 149(5):1163-1173 (2015).
Medrano et al. Role of TNFRSF1B polymorphisms in the response of Crohn's disease patients to infliximab. Human Immunology 75(1):71-75 (2014).
Mehmut et al.: Fas ligand and TNF-related apoptosis-inducing ligand induction on infiltrating lymphocytes in bladder carcinoma by Bacillus Calmette-Guerin treatment Urologica International 75:80-87 (2005).
Mei et al.: Familial expression of anti-*Escherichia coli* outer membrane porin C in relatives of patients with Crohn's disease. Gasteroenterology 130:1078-1085 (2006).
Mei. Association between IL 17 A and Il 17RA genes and inflammatory bowel disease (IBD). Abstract only. (2007) Journal unknown.
Melmed et al.: Patients with inflammatory bowel disease are at risk for vaccine-preventable illness. Am J Gasteroenterol 101:1834-1840 (2006).
Mesange et al.: Ligands of the antiestrogen-binding site are able to inhibit virion production of human immunodeficiency virus 1-infected lymphocytes. Molecular Pharmacology 50:75-79 (1996) Abstract only.
Messer et al.: Polymorphic structure of the tumor necrosis factor (TNF) locus: an NcoI polymorphism in the first intron of TNF-8 gene correlates with a variant in amino acid position 26 and a reduced level of TNF-8 production. J Exp Med 173:209-219 (1991).
Meylan et al.: The TNF-family cytokine TL1A drives IL-13 dependent small intestinal inflammation. Muscosal Immunol., 4(2):172-185, 2011.
Michelsen et al.: IBD-Associated Tl 1A Gene (TNFSF15) Haplotypes Determine Increased Expression of Tl 1A Protein. PLoS ONE. 4:e4719 (2009).

Migone et al.: TL1A is a TNF-like Ligand for DR3 and TR6/DcR3 and Functions as a T cell Costimulator, Immunity, 16:479-492, 2002.
Milner et al. Polymorphic analysis of the three MHC-linked HSP70 genes. Immunogenetics 36:357-362 (1992).
Mingjia et al.: How oestrogen or progesterone might change a woman's susceptibility to HIV 1 infections. The Australian and New Zealand Journal of Obstetrics and Gynecology Abstract only. 42:472-475 (2002).
Misiewicz et al.: The estrogen antagonist tamoxifen inhibits carrageenan induced inflammation in LEWIN female rats. Life Sciences 58:PL281-286 (1996).
Moghaddam et al.: Genetic structure of IDDM1: two separate regions in the major histocompatibility complex contribute to susceptibility or protection. Diabetes 47:263-269 (1998).
Morimoto et al. Single-step purification of F(ab')2 fragments of mouse monoclonal antibodies (immunoglobulins G1) by hydrophobic interaction high performance liquid chromatography using TSKgel Phenyl-5PW. Journal of Biochemical and Biophysical Methods 24:107-117, 1993.
Morinaga et al.: Database Uniprot (online), Mar. 8, 2011, Database Accession No. P02771.
Morinaga et al.: Primary structures of human a-fetoprotein and its mRNA. PNAS, 80:4604-4608, 1983.
Mow et al.: Association of antibody responses to microbial antigens and complications of small bowel Crohn's disease. Gastroenterology 126:414-424 (2004).
Mullins et al.: Perspective Series: Molecular Medicine in Genetically Engineered Animals, J Clin Invest, 97:1557-1560, 1996.
Mummidi et al.: Evolution of human and non-human primate CC chemokine receptor 5 gene and mRNA. Journal of Biological Chemistry, 275(5):18946-18961 (2000).
Mundwiler et al.: Inflammatory Bowel Disease Serologies in Ankylosing Spondylitis Patients: A Pilot Study, Arthritis Research and Therapy, 2009, vol. 11(6), pp. 2-8.
Murch et al.: Location of tumor necrosis factor alpha by immunochemistry in chronic inflammatory bowel disease. Gut 34:1705-1709 (1993).
Murillo et al.: CARD15 gene and the classification of Crohn's disease. Immunogenetics 54:59-61 (2002).
Murray et al.: GenBank Accession No. G08322 (Feb. 5, 1997).
Nadal et al.: Imbalance in the composition of the duodenal microbiata of children with coeliac disease. J Medical Microbiol. 56:1669-1674 (2007).
Nakamura et al.: In situ expression of the cell adhesion molecules in Inflammatory Bowel Disease; evidence of immunologic activation of vascular endothelial cells. Lab Investig 69(1):77-85 (1993).
Nakaya et al.: Estrogenic compounds suppressed interferon-gamma production in mouse splenocytes through direct cell-cell interaction. In Vitro Cell Dev Biol Anim 39:383-387 (2003).
Nalleweg et al.: Inflammatory bowel disease patients failing anti-TNF therapy show activation of the Th9/TH17 pathway. Gastroenterol 142(5)(Suppl1):S867-868; Abstract No. Tu1878 (2012).
Naundorf et at, IL-10 Interferes Directly with TCR-Induced IFN-[gamma] but not IL-17 Production in Memory T cells, European Journal of Immunology, 39(4):1066-1077, 2009.
NCBI Accession No. NM_001198.3 (5 pgs.) (Mar. 4, 2010).
NCBI Blast sequence search for SEQ ID No. 7; retrieved from: https://blast.ncbi.nlm.nih.gov/Blast.cgi on Sep. 12, 2018 (3 pgs.).
NCBI Gene Database, Gene ID: 133396, IL31RA interleukin 31 receptor A [*Homo sapiens* (human)}, [Retrieved online Aug. 31, 2018] Retrieved from https://www.ncbi.nlnnih.goV/gene/133396#gene-expression., Aug. 5, 2018 (16 pgs).
NCBI Gene Database, Gene ID: 3458, IFNG interferon gamma [*Homo sapiens* (human)}, [Retrieved online Aug. 31, 2018] Retrieved from< url:<ahref=https://www.ncbi.nlnnih.gov/gene/3458#gene-expression>>https://www.ncbi.nlnnih.gov/gene/3458#gene-expression., Aug. 25, 2018 (16 pgs).</url:<a>.
NCBI Reference SNP Cluster Report ID rs2241880; Retrieved from: http://www.ncbi.nlm.nih.gov/projects/SNP/snp_ref. .1gi?rs=2241880 on Sep. 23, 2016; 5 pages.

(56) References Cited

OTHER PUBLICATIONS

NCBI Reference SNP Cluster Report ID rs2836878; Retrieve from: http://www.ncbi.nlm.nih.gov/projects/SNP/snp_ref. .1gi?rs=2836878 on Sep. 23, 2016; 3 pages.
NCBI Reference SNP Cluster Report ID rs3764147; Retrieved from: http://www.ncbi.nlm.nih.gov/projects/SNP/snp_ref. .1gi?rs=3764147 on Sep. 23, 2016; 4 pages.
NCBI Reference SNP Cluster Report ID rs762421; Retrieved from: http://www.ncbi.nlm.nih.gov/projects/SNP/snp_ref. .1gi?rs=762421 on Sep. 23, 2016; 4 pages.
NCBI Reference SNP Cluster Report ID rs9271568; Retrieved from: http://www.ncbi.nlm.nih.gov/projects/SNP/snp_ref. .1gi?rs=9271568 on Sep. 23, 2016; 3 pages.
NCBI SNP 10 rs12638201 (1 pg.) (Jan. 31, 2001).
NCBI SNP 10 rs2066844 (1 pg.) (created May 2, 1997).
NCBI SNP 10 rs2066845 (1 pg.) (created May 2, 1997).
NCBI SNP 10 rs2302600 (1 pg.) (Feb. 15, 1996).
NCBI SNP 10 rs746503 (1 pg.) (Dec. 7, 2000).
NCBI SNP 10 rs7613548 (1 pg.) (created Apr. 19, 2000).
NCBI SNP ID rs11209063, 2006.
NCBI SNP ID rs12495640, 2006.
NCBI SNP ID rs2066847 (1 pg.) (created May 2, 1997).
NCBI SNP ID rs7374667 (2011).
Nedospasov et al.: DNA sequence polymorphism at the human tumor necrosis factor (TNF) locus. Numerous TNF/lymphotoxin alleles tagged by two closely linked microsatellitesin the upstream region of the lymphotoxin (TNF-beta) gene. J. Immunol. 147:1053-1059 (1991).
Nedospasov et al.: Genetic polymorphism of the human gene locus containing genes for tumor necrosis factors: ethnic differences in allele frequency distribution. Chemical Abstracts, 120(5):47183y (1994).
Nowak et al.: IL-9 as a mediator of Th17-driven inflammatory disease. Journal of Experimental Medicine 206(8):1653-1660 (2009).
Ogura et al.: A frameshift mutation in NOD2 associates with susceptibility to Crohn's disease. Nature 411:603-606 (2001).
Ogura et al.: NOD2, a Nod1/Apaf-1 family member that is restricted to monocytes and activates NF-kB. J Biol Chem 276:4812-4818 (2001).
Oh et al.: A randomized, controlled trial to evaluate the effect of an anti-interleukin-9 monoclonal antibody in adults with uncontrolled asthma. Respiratory Research 14:93 (2013).
Ohmen et al.: Susceptibility locus for inflammatory bowel disease on chromosome 16 has a role in Crohn's disease, but not in ulcerative colitis. Hum Mol Genet 5:1679-1683 (1996).
Okazaki et al.: Contributions of the IBD5, IL23R, ATG16L 1, and NOD2 to Crohn's disease risk in a population-based case-controlled study: evidence of gene-gene interaction. Inflamm Bowel Disease 14:1528-1541 (2008).
Orholm et al.: Familial occurrence of inflammatory bowel disease. New England Journal of Medicine 324:84-88 (1991).
Over et al.: Thromphilia and inflammatory bowel disease: does factor V mutation have a role? European Journal of Gastroenterology and Hepatology 10:827-829 (1998).
Owerbach et al. The HOXD8 locus (2q31) is linked to type I diabetes—interaction with chromosome 6 and 11 disease susceptibility genes. Diabetes 44:132-136 (1995).
Pallone et al.: Genetic and Pathogenetic Insights into Inflammatory Bowel Disease, Current Gastroenterology Reports, 2003, vol. 5, pp. 487-492.
Papadakis et al.: An interaction between IL-23R and IL-17A and between IL-23R and Il 17RA haplotypes is necessary for susceptibility to Crohn's disease. Abstract only. (2007) Journal unknown.
Papadakis et al.: Anti-Flagellin (Cbir1) phenotypic and genetic Crohn's Disease associations. Inflamm Bowel Dis 13(5):524-530 (2007).
Papadakis et al.: IL1A synergizes with IL-12 and IL-18 to enhance IFN-y production in human T cells and NK cells, The Journal of Immunology, 172:7002-7007, 2004.
Papadakis et al.: Phenotypic and functional characterization of CCR9+ T lymphocytes in small intestinal Crohn's disease. Abstract only. (2006). Journal unknown.
Papp et al.: Seroreactivity to microbial components in Crohn's disease is associated with Ileal involvement, noninflammatory disease behavior and NOD2/CARD15 genotype but not with risk for surgery in a Hungarian cohort of IBO patients. Inflamm Bowel Disease 13:984-992 (2007).
Pappu et al.: TL1A-DR3 interaction regulates Th17 cell function and Th17-Mediated autoimmune disease. Journal of Experimental Medicine, 205(5):1049-1062, 2008.
Parente et al.: Bowel Ultrasound in Assessment of Crohn's Disease and Detection of Related Small Bowel Strictures: A Prospective Comparative Study Versus X Ray and Intraoperative Findings, Gut, 50: 490-495, 2002.
Parkes et al.: Susceptibility loci in inflammatory bowel disease. Lancet 348:1588 (1996).
Parrello et al.: Upregulation of the IL-12 receptor beta 2 chain in Crohn's disease. J Immunol 165:7234-7239 (2000).
Partanen et al.: Low degree of DNA polymorphism in the HLA-linked lymphotoxin (tumor necrosis factor-B) gene. Scand J. Immunol. 28:313-316 (1988).
PAUL. Chapter 19. Fundamental Immunology 4th edition pp. 663-665 (1998).
PCT/2011/028694 International Preliminary Report on Patentability dated Sep. 18, 2012.
PCT/2011/028694 International Search Report and Written Opinion dated Jul. 27, 2011.
PCT/2012/030614 International Search Report and Written Opinion dated Sep. 28, 2012.
PCT/US1995/001434 International Preliminary Examination Report dated May 22, 1996.
PCT/US1995/001434 International Search Report dated Jul. 21, 1995.
PCT/US1995/001434 Written Opinion dated Nov. 17, 1995.
PCT/US1995/006107 International Preliminary Examination Report dated Jun. 5, 1996.
PCT/US1995/006107 International Search Report dated Oct. 6, 1995.
PCT/US1995/006107 Written Opinion dated Feb. 12, 1996.
PCT/US1997/000042 International Preliminary Examination Report dated Apr. 1, 1998.
PCT/US1997/000042 International Search Report dated Apr. 21, 1997, dated May 14, 1997.
PCT/US1997/000042 Written Opinion dated Oct. 29, 1997.
PCT/US2000/025112 International Preliminary Examination Report dated Dec. 20, 2001.
PCT/US2000/025112 International Search Report dated Aug. 6, 2001.
PCT/US2003/023926 International Preliminary Examination Report dated Aug. 19, 2004.
PCT/US2003/023926 International Search Report dated Jun. 23, 2004.
PCT/US2005/018161 International Preliminary Report on Patentability dated Apr. 15, 2009.
PCT/US2005/018161 International Search Report dated Jun. 4, 2008.
PCT/US2005/018161 Written Opinion dated Jun. 4, 2008.
PCT/US2005/044335 International Preliminary Examination Report dated Jun. 13, 2007.
PCT/US2005/044335 International Search Report dated Sep. 22, 2006.
PCT/US2005/044335 Written Opinion dated Sep. 22, 2006; dated Aug. 26, 2006.
PCT/US2006/22427 International Search Report dated Sep. 5, 2006 EP Application 2006772657.
PCT/US2007/008597 International Preliminary Examination Report dated Oct. 8, 2008.
PCT/US2007/008597 International Search Report dated Jun. 4, 2008.
PCT/US2007/008597 Written Opinion dated Jun. 4, 2008.
PCT/US2008/054033 International Preliminary Examination Report dated Aug. 19, 2009.

(56) References Cited

OTHER PUBLICATIONS

PCT/US2008/054033 International Search Report dated Aug. 21, 2008.
PCT/US2008/054033 Written Opinion dated Aug. 21, 2008.
PCT/US2008/055020 International Preliminary Report on Patentability dated Aug. 26, 2009.
PCT/US2008/055020 International Search Report and Written Opinion dated Aug. 14, 2008, 8 pages.
PCT/US2008/055236 International Preliminary Examination Report dated Sep. 1, 2009.
PCT/US2008/055236 International Search Report and Written Opinion dated Nov. 14, 2008.
PCT/US2008/056103 International Preliminary Report on Patentability dated Nov. 24, 2009.
PCT/US2008/056103 International Search Report dated Sep. 8, 2008.
PCT/US2008/056103 Written Opinion dated Sep. 8, 2008.
PCT/US2008/057028 International Preliminary Report on Patentability dated Sep. 15, 2009.
PCT/US2008/057028 International Search Report dated Oct. 10, 2008.
PCT/US2008/057028 Written Opinion dated Oct. 10, 2008.
PCT/US2008/057820 International Preliminary Report on Patentability dated Sep. 22, 2009.
PCT/US2008/057820 International Search Report dated Sep. 11, 2008.
PCT/US2008/057820 Written Opinion dated Sep. 11, 2008.
PCT/US2008/061652 International Preliminary Report on Patentability dated Oct. 27, 2009.
PCT/US2008/061652 International Search Report dated Dec. 1, 2008.
PCT/US2008/061652 Written Opinion dated Dec. 1, 2008.
PCT/US2008/062531 International Preliminary Report on Patentability dated Nov. 10, 2009.
PCT/US2008/062531 International Search Report and Written Opinion dated Nov. 18, 2008.
PCT/US2008/063202 International Preliminary Examination Report dated Nov. 10, 2009.
PCT/US2008/063202 International Search Report dated Nov. 18, 2008.
PCT/US2008/063202 Written Opinion dated Nov. 18, 2008.
PCT/US2008/080526 International Preliminary Report on Patentability dated Apr. 20, 2010.
PCT/US2008/080526 International Search Report and Written Opinion dated Mar. 25, 2009, 11 pages.
PCT/US2009/044720 International Preliminary Report on Patentability dated Nov. 23, 2010.
PCT/US2009/044720 International Search Report dated Nov. 5, 2009.
PCT/US2009/044720 Written Opinion dated Nov. 5, 2009.
PCT/US2009/048319 International Preliminary Report on Patentability dated Jan. 5, 2011.
PCT/US2009/048319 International Search Report and Written Opinion dated Nov. 6, 2009.
PCT/US2009/059190 International Preliminary Report on Patentability dated Apr. 5, 2011.
PCT/US2009/059190 International Search Report and Written Opinion dated Mar. 16, 2010.
PCT/US2009/061698 International Preliminary Report on Patentability dated Apr. 26, 2011.
PCT/US2009/061698 International Search Report dated Mar. 16, 2010.
PCT/US2009/061698 Written Opinion dated Mar. 16, 2010.
PCT/US2009/065928 International Preliminary Report on Patentability dated May 31, 2011.
PCT/US2009/065928 International Search Report dated Aug. 3, 2010.
PCT/US2009/065928 Written Opinion dated Aug. 3, 2010.
PCT/US2009/069531 International Preliminary Report on Patentability dated Jun. 29, 2011.
PCT/US2009/069531 International Search Report and Written Opinion dated Aug. 4, 2010, 11 pages.
PCT/US2009/069534 International Search Report dated Mar. 1, 2010.
PCT/US2009/069541 International Preliminary Report on Patentability dated Jun. 29, 2011.
PCT/US2009/069541 International Search Report dated Mar. 4, 2010.
PCT/US2009/069541 Written Opinion dated Mar. 4, 2010.
PCT/US2010/020921 International Reporton Patentability dated Jul. 19, 2011.
PCT/US2010/020921 International Search Report and Written Opinion dated May 5, 2010.
PCT/US2010/030359 International Preliminary Report on Patentability dated Oct. 11, 2011.
PCT/US2010/030359 International Search report and Written Opinion dated Aug. 11, 2010.
PCT/US2010/043427 International Search Report dated Dec. 3, 2010.
PCT/US2011/021180 International Preliminary Report on Patentability dated Jun. 15, 2011.
PCT/US2011/021180 International Search Report and Written Opinion dated Jun. 15, 2011.
PCT/US2011/021382 International Preliminary Report on Patentability dated Jul. 17, 2012.
PCT/US2011/021382 International Search Report and Written Opinion dated Mar. 15, 2011.
PCT/US2012/030611 International Preliminary Report on Patentability dated Oct. 1, 2013.
PCT/US2012/030611 International Search Report and Written Opinion dated Sep. 7, 2012.
PCT/US2012/030616 International Preliminary Report on Patentability dated Nov. 19, 2013.
PCT/US2012/030616 International Search Report and Written Opinion dated Sep. 17, 2012.
PCT/US2014/032054 International Preliminary Report on Patentability dated Sep. 29, 2015, 12 pages.
PCT/US2014/032054 International Search Report and Written Opinion dated Aug. 5, 2014, 14 pages.
PCT/US2014/038333 International Preliminary Report on Patentability dated Nov. 17, 2015.
PCT/US2014/038333 International Search Report and Written Opinion dated Nov. 20, 2014.
PCT/US2014/038468 International Preliminary Report on Patentability dated Nov. 17, 2015, 7 pages.
PCT/US2014/038468 International Search Report and Written Opinion dated Nov. 18, 2014, 11 pages.
PCT/US2014/047326 International Preliminary Report on Patentability dated Jan. 19, 2016, 7 pages.
PCT/US2014/047326 International Search Report and Written Opinion dated Dec. 22, 2014, 9 pages.
PCT/US2014/054425 International Preliminary Report on Patentability dated Mar. 8, 2016.
PCT/US2014/054425 International Search Report and Written Opinion dated Dec. 31, 2014, 12 pages.
PCT/US2016/022494 International Search Report and Written Opinion dated Jun. 3, 2016.
PCT/US2016/032180 International Preliminary Report on Patentability dated Nov. 30, 2017.
PCT/US2016/032180 International Search Report and Written Opinion dated Aug. 19, 2016, 8 pages.
PCT/US2017/023082 International Search Report and Written Opinion dated Aug. 15, 2017.
PCT/US2017/058019 International Search Report and Written Opinion dated Feb. 15, 2018.
PCT/US2018/028397 International Search Report and Written Opinion dated Jul. 9, 2018.
Peltekova et al.: Functional variants of OCTN cation transporter genes are associated with Crohn disease. Nature Genetics, 16(5):471-475, 2004.
Pennisi, E. A Closer look at SNPs suggests difficulties. Science, 281 (5384):1787-1789, 1998.

(56) References Cited

OTHER PUBLICATIONS

Pericak-Vance et al.: Approaches to gene mapping in complex human diseases. Wiley-Liss New York 1998.
Perkin Elmer Catalog 1992, p. 12.
Picornell et al.: TNFSF15 is an ethnic specific IBD gene. Inflamm. Bowel Disease, 13(11):1333-1338, 2007.
Pierik et al. Tumour Necrosis Factor-a Receptor 1 and 2 Polymorphisms in Inflammatory Bowel Disease and their Association with Response to Infliximab. Alimentary Pharmacology & Therapeutics 20(3):303-310 (2004).
Pinchuk et al.: Human Colonic Myofibroblast Promote Expansion of CD4+ CD25high Foxp3+ Regulatory T Cells, Gastroenterology, 140(7):2019-2030, pp. 1-19, and p. 8, 2011.
Plevy et al., Tumor necrosis factor (TFN) microsatellite associations with HLA-DR2+ patients define Crohn's disease (cd) and ulcerative colitis (uc)-specific genotypes. Gastroenterology 106:A754 (1994).
Plevy et al. TNF-alpha MRNA levels differentiated mucosal inflammation in crohn's disease from ulcerative colitis. J. Immunology 150:10a (1993).
Plevy et al.: A role of TNF-alpha and mucosal T-helper-1 cytokines in the pathogenesis of Crohn's disease. The Journal of Immunology 84:1397-1398 (2004).
Plevy et al.: Increased mucosal tnf-alpha mrna levels and numbers of tnf-alpha producing cells are unique to mucosal inflammation in crohn's disease, Faseb Journal, Abstract 58498:A1010 (Apr. 1994).
Plevy et al.: The tumor necrosis factor (TNF) microsatellite haplotype A2B1C204E1 correlates with increased TNF production in Crohn's disease. Abstract only AASLD at Digestive disease week (1995).
Plevy et al.: Tumor necrosis factor microsatellites define Crohn's disease—associated haplotype on chromosome 6. Gasteroenterology 110:1053-1060 (1996).
Pociot et al.: A tumor necrosis factor beta gene polymorphism in relation to monokine secretion and insulin dependent diabetes mellitus. Scand J. Immunol., 33:37-49 (1991).
Pociot et al.: Association of tumor necrosis factor and class II major histocompatibility complex alles with secretion of tnf alfa and tnf beta by human mononuclear cells: a possible link to insulin-dependent diabetes mellitus. Abstract only. Eur. J. Immunology 23:224-231 (1993).
Poicot et al.: Polymorphic analysis of the human MHC-linked heat shock protein 70 (HSP70- and HSP70-Hom genes in insulin-dependent diabetes mellitus (IOOM). Scand J Immunol 38:491-495 (1993).
Polanczyk et al.: The protective effect of 17beta-estradiol on experimental autoimmune encephalomyelitis is mediated through estrogen receptor-a. American J of Pathology 163:1599-1605 (2003).
Potts et al.: Using microbicides to fight the spread of HIV. Science 300:431 (2003).
Prehn et al.: The T Cell Costimulator TL 1A is Induced by Fe R Signaling in Human Monocytes and Dendritic Cells. J Immunol 178:4033-4038 (2007).
Prideaux et al.: Inflammatory Bowel Disease in Asia: A Systematic Review, Journal of Gastroenterology and Hepatology, 27(8):1266-1280, 2012.
Queen et al. A humanized antibody that binds to the interleukin 2 receptor. Proc. Natl. Acad Sci USA 86:10029-10032, 1989.
R&D datasheet for human/mouse TL1A/TNFSF15 antibody, catalog No. MAB7441; clone #293327 (Feb. 7, 2018).
Radlmayr et al.: The c-insertion mutation of the NOD2 gene is associated with fistulizing and fibrostenotic phenotypes in Crohn's diseases. Gasterenterology 122:2091-2095 (2002).
Raychaudhuri et al.: Genetic Variants at CD28, PRDM1 and CD2/CD58 are Associated with Rheumatoid Arthritis Risk, Nature Genetics, 2009, vol. 41(12), pp. 1313-1318, and online methods.
Rector et al.: Mannan-binding lectin (MBL) gene polymorphisms in ulcerative colitis and Crohn's disease. Genes and Immunity 2:323-328 (2001).
Redon et al. Global variation in copy number in the human genome. Nature. 444(7118): 444-54 (2006).
Reference SNP Cluster report for rs2986754 retrieved from: http://www.ncbi.nlm.nih.gov/projects/SNP/snp_ref.cgi?rs=2986754 on Sep. 13, 2016; 3 pages.
Reference SNP Cluster report for rs746503 retrieved from: http://www.ncbi.nlm.nih.gov/projects/SNP/snp_ref.cgi?rs+746503 on Sep. 15, 2016; 4 pages.
Reichwald et al. TL1A induces TCR independent IL-6 and TNF-alpha production and growth of PLZF leukocytes. PLOS ONE 9(1):e85793, 2013.
Reinecker et al.: Enhanced secretion of tumor necrosis factor-alpha, IL-6 and IL-1 beta by isolated lamina propia mononuclear cells from patients with ulcerative colitis and Crohn's disease Clin Exp Immunol 94:174-181 (1993).
Richard et al. The TNF-family cytokine TL1A: from lymphocyte costimulator to disease coconspirator. J Leukocyte Biol 98:333-345 2015.
Riechmann et al. Reshaping human antibodies for therapy. Nature, 332.6162 (1988): 323-7.
Rieder et al.: Intestinal Fibrosis in Inflammatory Bowel Disease-Current Knowledge and Future Perspectives, J.Crohns Colitis, 2:279-290, 2008 .
Rioux et al.: Genetic Variation in the 5q31 Cytokine Gene Cluster Confers Susceptibility to Crohn Disease, Nature Genetics, 2001, vol. 29(2), pp. 223-228.
Rioux et al.: Genome-wide association study identifies new susceptibility loci for Crohn disease and implicates autophagy in disease pathogenesis. Nature Genetics 39(5):596-604 (2007).
Rodriguez-Caballero et al.: A new simple whole blood flow cytometry-based method for simultaneous identification of activated cells and quantitative evaluation of cytokines released during activation Laboratory Investigation 84:1387-1398 (2004).
Roth et al.: Familial empiric risk estimates of inflammatory bowel disease in Ashkenazi Jews. Gastroenterology 96:1016-1020 (1989).
Roth et al.: Geographic origins of Jewish patients with inflammatory bowel disease. Gastroenterology 97:900-904 (1989).
Rothe et al.: The human combinatorial antibody library HuCAL GOLD combines diversification of all six CDRs according to the natural immune system with a novel display method for efficient selection of high-affinity antibodies. J. Mol. Bio. 376:1182-1200, 2008 .
Roussomoustakaki et al.: Genetic markers may predict disease behavior in patients with ulcerative colitis. Gastroenterology, 112:1845-1853, 1997.
Rozen et al.: Crohn's disease in the Jewish population of Tei-Aviv-Yafo: epidemiologic and clinical aspects. Gastroenterology 76:25-30 (1979).
Salem et al.: Mediation of the immunomodulatory effect of beta-estradiol on inflammatory response by inhibition of recruitment and activation of inflammatory cells and their gene expression of TNF-alpha and IFN-gamma. Inti Archives of Allergy and Immunology Abstract Only. 121:235-245 (2000).
Salem. Estrogen, a double-edged sword: modulation of TH1- and THw-medicated inflammations by differential regulation of T J1/TH2 cytokine production. Inflammation and Allergy 3:97-104 (2004).
Saruta et al.: High frequency haplotypes in the X-chromosome locus TLR8 are associated with both CD and UC in females. Inflammatory Bowel Disease. 15(3):321-327 (2009).
Saruta et al.: TLR8-mediated activation of human monocytes inhibits TL 1A expression. Eur J Immunol 39:2195-2202 (2009).
Sategna-Guidetti et al.: Tumor necrosis factor cachectin in Crohn's disease—relation of C385 serum concentration to disease activity. Recenti Progressi 84:93-99 (1993).
Satsangi et al.: Contribution of Genes of the Major Histocompatibility Complexto Susceptibility and Disease Phenotype in Inflammatory Bowel Disease, The Lancet, 347:1212-1217, 1996.
Satsangi et al.: The genetics of inflammatory bowel disease. Gut 40:572-574 (1997).
Saxon et al.: A distinct subset of antineutrophil cytoplasmic antibodies is associated with inflammatory bowel disease. J Allergy Clin. Immunol. 86:202-210 (1990).
Schimanski et al.: Effect of chemokine receptors CXCR4 and CCR7 on the metastatic behavior of human colorectal cancer Clinical Cancer Research 11:1743-1750 (2005).

(56) References Cited

OTHER PUBLICATIONS

Scientists Discover New Gene Associated with Crohn's Disease. BusinessWire https://www.businesswire.com/news/home/20070124005277/en/Scientists-Discover-New-Gene-Crohns-Disease (Jan. 24, 2017).
See et al.: Increased tumor necrosis factor alpha (TNF-alpha) and natural killer cell (NK) function using an integrative approach in late stage cancers. Immunological Investigations 31:137-153 (2002).
Seidelin et al.: Upregulation of cIAP2 in Regenerating Coloncytes in Ulcerative Colitis, Virchows Arch, 451:1031-1038, 2007.
Shanahan et al.: Inflammatory Bowel Disease. Textbook of Internal Medicine. W.N. Kelle et al. (editor) 2nd edition J. B. Lippincott Company, Philadelphia 81:489-502 (1992).
Shetty et al.: Pharmacogenomics of response to anti-tumor necrosis factor therapy in patients with Crohn's disease. American Journal of Pharmacogenomics 2:215-221 (2002).
Shih et al. Reversal of murine colitis and fibrosis by neutralizing TL1A antibody: potential novel therapy to alter natural history of Crohn's disease. Gastroenterol 142(5):S84, Abstract #357, 2012.
Shih et al.: Inhibition of a novel fibrogenic factor TI 1 a reverses established colonic fibrosis. Mucosal Immunol., 7(6):1492-1503, 2014.
Shih et at, Constitutive TL1A (TNFSF15) Expression on Lymphoid or Myeloid Cells Leads to Mild Intestinal Inflammation and Fibrosis, PLOS One, 6(1), pp. 1-16, 2011.
Shih et at, Microbial Induction of Inflammatory Bowel Disease Associated Gene TL1A (TNFSF15) in Antigen Presenting Cells, Eur. J. Immunol., 39:3239-3250, 2009.
Shovam et al.: Evaluation of the BioPiex 2200 ANA screen: Analysis of 510 healthy subjects: incidence of natural/predictive autoantibodies. Annals of the New York Academy of Science, 1050:380-388 (2005).
Silman et al.: Epidemiology and genetics of rheumatoid arthritis. Arthritis Research 4 Supp 3:S265-S272 (2002).
Silverberg et al.: Evidence for linkage between Crohn's disease (CD) and a locus near the major histocompatibility complex (MHC) on chromosome 6 in a Canadian inflammatory bowel disease (IBO) population. Gastroenterology 116:G3560 AGA Abstracts (1999).
Silverberg et al.: The HLA DRBL 0103 allele is associated with Crohn's disease (CD) in a Toronto inflammatory bowel disease (IBO) population. Gastroenterology 116:G3559 AGA Abstracts (1999).
Singal et al.: D6S273 microsatellite polymorphism and susceptibility to Rhematoid Arthritis. Tissue Antigens 52:353-358 (1998).
Singal et al.: Genetics of rheumatoid arthritis (RA): two separate regions in the major histocompatibility complex contribute to susceptibility to RA. Immunol Lett 69:301-306, (1999).
Sitaraman et al.: Elevated flagellin-specific immunoglobulins in Crohn's disease. Am J Physiol Gastrointest Liver Physiol 288:G403-G406 (2005).
Smith et al. Topical estrogen protects against SIV vaginal transmission without evidence of systemic effect. AIDS 18:1637-1643 (2004).
Smith et al.: Cooperative interactions of LFA-1 and Mac-1 with intercellular adhesion molecule-1 in facilitating adherence and transendothelial migration of human neurophils in vitro. J Clin Invest 83:2008-2017 (1989).
Smith et al.: Estrogen protects against vaginal transmission of simian immunodeficiency virus. J Infectious Diseases 182:708-715 (2000).
Smith et al.: Recognition of an endothelial determinant for CD18-dependent human neutrophil adherence and transendothelial migration. J Clin Invest 82:1746-1756 (1988).
Smith. Adherence of neutrophils to canine cardiac myocyyes in vitro is dependent on intercellular adhesion molecule-1. J Clin Invest 88:1216-1223 (1991).
Smith. Transendothelial Migration, in Breakthroughs in Molecular Biology, vol. 4: Adhesion: Its Role in Inflammatory Disease. Harlan, J. and Liu D., eds., W. H. Freeman & Co. New York. pp. 83-115 (1992).

Sobrino et al.: SNP's in Forensic Genetics: A Review on SNP Typing Methodologies, Forensic Science International, 154:181-194, 2005.
Spinelli et al.: Intestinal Fibrosis in Crohn's Disease: Medical Treatment or Surgery?, Current Drug Targets, 11(2):242-248, 2010.
Springer et al.: Adhesion receptors of the immune system. Nature 346:425-433 (1990).
Springer, T. A. et al.: Leukocyte adhesion molecules structure function and regulation. New York, Springer-Verlag 1990 Book-Table of Contents Book not included.
Staunton et al. The arrangement of the immunoglobulin-like domains of ICAM-1and binding sites for LFA-1 and rhinovirus. Cell 61:243-254 (1990).
Staunton et al.: Primary Structure of ICAM-1 demonstrates interaction between member of the immunoglobulin and integrin supergene families. Cell 52:925-933 (1988).
Steer et al.: Development of rheumatoid arthritis is not associated with two polymorphisms in the Crohn's disease gene CARD15 Rheumatology 42:304-307 (2003).
Stites et al.: Chapter 22 of the 4th edition of Basic and Clinical Immunology, Lange Medical Publications, Los Altos, California, p. 325-365 (1982).
Stratagene Catalog. 1988; p. 39. Gene Characterization Kits. Table of Contents.
Strater et al.: Expression of TRAIL and TRAIL receptors in colon carcinoma: TRAIL-R1 is an independent prognostic parameter. Clinical Cancer Research 8:3734-3740 (2002).
Strober et at, Proinflammatoly Cytokines in Pathogenesis of Inflammatory Bowel Diseases, Gastroenterology, 140(6):1756-1767, 2011.
Strong, S. Surgical management of Crohn's disease, in: Surgical Treatment: Evidence Based and Problem Oriented. Holzheimerand Mannick, editors. Munich: Zuckschwerdt, 7 pages, 2001.
Stulik et al.: The different expression of proteins recognized by monoclonal anti-heat shock protein 70 (hsp70) antibody in human colonic diseases. Electrophoresis 18:625-628 (1997).
Sugaya et al.: Gene organization of human NOTCH4 and (CTG)n polymorphism in this human counterpart gene of mouse protooncogene Int3. Gene 189:235-244 (1997).
Sugaya et al.: Three genes in the human MHC class III region near the junction with the class II: gene for receptor of advanced glycosylation end products, PBX2 homeoboxgene and a notch homolog, human counterpart of mouse mammary tumor gene int-3. Genomics 23:408-419 (1994).
Sullivan et al.: Prevalence of a mutation causing C2 deficiency in systemic lupus erythematosus. J of Rheumatology 21:1128-1133 (1994).
Syvanen, Ann-Christine, Accessing Genetic Variation: Genotyping Single Nucleotide Polymorphisms, Nature Reviews, 2: 930, 2001.
Takedatsu et al.: Linkage of CD-related serological phenotypes: NFKB1 haplotypes are associated with anti-CBir1 & ASCA, and show reduced NF-KB activation. Gut. 58:60-67 (2009).
Takedatsu et al.: TL1A (TNFSF15) Regulates the Development of Chronic Colitis by Modulating both T helper (TH) 1 and TH17 Activation; Gastroenterology; HHS Public Access; 135(2): 552-567 (2009).
Targan et al.: Antibodies to a novel flagellin (CBir1) define a unique serologic response in Crohn's disease (CD). Gastroenterology Abstract only 126(4), Suppl 2:A113 (2004).
Targan et al.: Antibodies to CBir1 flagellin define a unique response that is associated independently with complicated Crohn's disease. Gastroenterology 128:2020-20289 (2005).
Targan et al.: Definition of a lamina propia T cells responsive state enhanced cytokine responsiveness of T cells stimulated through the CD2 pathway. J Immunol 154:664-675 (1995).
Targan et al.: TL1A (TNFSF15): A Master Regulator of Mucosal Inflammation, Advances in Experimental Medicine and Biology, 691: 681-683, 2011 .
Tarlow et al.: Polymorphism in human IL-1 receptor antagonist gene intron 2 is caused by variable Nos. of an 86-bp tandem repeat. Hum Genet 91:403-404 (1993).

(56) References Cited

OTHER PUBLICATIONS

Taylor et al.: Analysis of IBD5-related polymorphisms: IRF1 but not SLC22A4 or SLC22A5 is associated with 18D in Puerto Rican populations. Digestive Disease Week Abstract only (2006). Journal unknown.
Taylor et al.: ANCA pattern and LTA haplotype relationship to clinical responses to anti-TNF antibody treatment in Crohn's disease. Gastroenterology, 120:1347-1355, 2001.
Taylor et al.: Genes regulating the expression of antibody to C8irl flagellin in humans are located within a syntenic region to the major mouse colitogenic locus Cdcs1. AGA Institute Abstract #444 p. A-64 (2006).
Taylor et al.: IL23R haplotypes provide a large population attributable risk for Crohn's disease. Inflammatory Bowel 14:1185-1191 (2008).
Taylor et al.: Linkage disequilibrium mapping identifies a Class III major histocompatibility complex (MHC) susceptibility haplotypes to Crohn's disease in Ashkenazi Jews. American Journal of Human Genetics. 65(4): A102, abstract 534 (1999).
Taylor et al.: Specific clinical and immunological features in Crohn's disease patients are associated with the MHC class III marker Notch4. Gastroenterology. 118(Supp 2):A869, Abstract 4830 (2000).
The Wellcome Trust Case Control Consortium, Genome-Wide Association Study of 14,000 Cases of Seven Common Diseases and 3,000 Shared Controls, Nature, 2007, vol. 447, pp. 661-678.
Thomas et al.: Estrogen and raloxifen activities on amyloid-beta-induced inflammatory reaction. Microvascular Research 61:28-39 (2001).
Thomas et al.: The TNF Family Member TL1A induces IL-22 Secretion in Committed Human TH17 Cells Via IL-9 Induction, Journal of Leukocyte Biology, 101:1-20, 2016.
Tomassini et al.: cDNA cloning reveals that the major group rhinovirus receptor on Hela cells in intercellular adhesion molecule-1. PNAS USA 86:4907-4911 (1989).
Tomlinson I. and Holliger P. Methods for generating multivalent and bispecific antibody fragments. Methods Enzymol 326:461-479, 2000 .
Torok et al.: Crohn's disease is associated with a Toll-like receptor-9 polymorphism. Gastroenterology 127:365-368 (2004).
Torres et al.: The Hermansky-pudlak 1 (HPS1) gene is associated with IBD in Puerto Rico independent of the known HPS1 insertion mutation. Abstract only, 2006 Journal unknown, 1 page.
Tountas et al. Heterogenous association between allele 2 of IL-2 receptor antagonist (ILC4371 Ra) and ulcerative colitis in Jewish and non-Jewish populations. Abstract XP000673114 only. J. Investigative Medicine 44(1) (1996).
Tountas et al.: Genetic association between allele 2 of IL-1 receptor antagonist (IL-1 ra) and ulcerative colitis in Los Angeles based hispanic population. Abstract XP000673112 only. Gastroenterology 108:806-813 (1995).
Tountas et al.: Increased carriage of allele 2 of IL-1 receptor antagonist (IL-1 ra) in Jewish population: the strongest known genetic association in ulcerative colitis. American Gastroenterology Association Abstract Only (1996).
Trachtenberg et al.: Rare HLA DR-DQ haplotypes associated with inflammatory bowel disease. Human Immunol 55 (supp. 1):59 Abstract #42 (1997).
Tremelling et al.: Contribution of TNFSF15 Gene Variants to Crohn's Disease Susceptibility Confirmed in UK Population, Inflammatory Bowel Diseases, 14(6):733-737, 2008.
Tromm et al.: Inflammatory Bowel Disease: endoscopic diagnostics. (Reprints available at the Department of Gastroenterology and Hepatology Bergmannshell Hospital) 19th El., Falk Foundation, University of Bochum, Federal Republic of Germany pp. 3-38 (2009).
Trowsdale et al.: Map of the human MHC. Immunol. Today 12:443-446 (1991).
Turchan et al.: Estrogen protects against the synergistic toxicity by HIV proteins, methamphetamine and cocaine. BMC Neuroscience 2:3 (2001).

U.S. Appl. No. 08/196,003 Office Action dated Dec. 12, 1995.
U.S. Appl. No. 08/196,003 Office Action dated Oct. 2, 1996.
U.S. Appl. No. 08/245,297 Office Action dated Dec. 9, 1996.
U.S. Appl. No. 08/245,297 Office Action dated Jan. 22, 1996.
U.S. Appl. No. 08/245,297 Office Action dated Jul. 11, 1996.
U.S. Appl. No. 08/245,297 Office Action dated Mar. 15, 1995.
U.S. Appl. No. 08/587,911 Office Action dated Apr. 15, 1997.
U.S. Appl. No. 08/587,911 Office Action dated Jan. 5, 1998.
U.S. Appl. No. 08/587,911 Office Action dated Jul. 6, 1998.
U.S. Appl. No. 08/798,668 Notice of Allowance dated Apr. 29, 1999.
U.S. Appl. No. 08/798,668 Office Action dated Aug. 10, 1997.
U.S. Appl. No. 08/798,668 Office Action dated Jan. 29, 1998.
U.S. Appl. No. 08/798,668 Office Action dated Jun. 6, 1997.
U.S. Appl. No. 08/933,824 Office Action dated Apr. 14, 1998.
U.S. Appl. No. 08/933,824 Office Action dated Jan. 5, 1999.
U.S. Appl. No. 09/395,345 Office Action dated May 3, 2000.
U.S. Appl. No. 09/395,345 Office Action dated May 9, 2001.
U.S. Appl. No. 09/395,345 Office Action dated Nov. 21, 2000.
U.S. Appl. No. 09/419,406 Notice of Allowance dated Mar. 19, 2002.
U.S. Appl. No. 09/419,406 Office Action dated Apr. 24, 2000.
U.S. Appl. No. 09/419,406 Office Action dated Dec. 28, 2000.
U.S. Appl. No. 09/419,406 Office Action dated Jul. 17, 2001.
U.S. Appl. No. 09/419,408 Office Action dated May 30, 2002.
U.S. Appl. No. 09/419,408 Office Action dated Nov. 14, 2002.
U.S. Appl. No. 09/419,408 Office Action dated Feb. 1, 2000.
U.S. Appl. No. 10/075,425 Office Action dated Jun. 17, 2005.
U.S. Appl. No. 10/075,425 Office Action dated Oct. 1, 2004.
U.S. Appl. No. 10/356,736 Office Action dated Apr. 10, 2006.
U.S. Appl. No. 10/356,736 Office Action dated Apr. 26, 2007.
U.S. Appl. No. 10/356,736 Office Action dated Aug. 14, 2008.
U.S. Appl. No. 10/356,736 Office Action dated Jul. 7, 2005.
U.S. Appl. No. 10/356,736 Office Action dated Nov. 30, 2007.
U.S. Appl. No. 10/526,256 Office Action dated Aug. 25, 2009.
U.S. Appl. No. 10/526,256 Office Action dated Dec. 29, 2008.
U.S. Appl. No. 10/526,256 Office Action dated May 9, 2008.
U.S. Appl. No. 11/720,785 Office Action dated Dec. 23, 2010.
U.S. Appl. No. 11/720,785 Office Action dated Jul. 19, 2010.
U.S. Appl. No. 12/032,442 Restriction Requirement dated May 11, 2010.
U.S. Appl. No. 12/196,505 Final Office Action dated Dec. 7, 2012.
U.S. Appl. No. 12/196,505 Final Office Action dated Nov. 4, 2011.
U.S. Appl. No. 12/196,505 Final Office Action dated Nov. 9, 2010.
U.S. Appl. No. 12/196,505 Non-Final Office Action dated Apr. 12, 2010.
U.S. Appl. No. 12/196,505 Non-Final Office Action dated Jun. 14, 2013.
U.S. Appl. No. 12/196,505 Non-Final Office Action dated Mar. 25, 2011.
U.S. Appl. No. 12/196,505 Non-Final Office Action dated May 15, 2012.
U.S. Appl. No. 12/196,505 Restriction Requirement dated Apr. 23, 2009.
U.S. Appl. No. 12/527,376 Final Office Action dated May 25, 2012.
U.S. Appl. No. 12/527,376 Office Action dated Oct. 19, 2011.
U.S. Appl. No. 12/527,376 Restriction Requirement dated Sep. 1, 2011.
U.S. Appl. No. 12/528,055 Office Action dated Apr. 30, 2015.
U.S. Appl. No. 12/528,055 Office Action dated Jul. 21, 2014.
U.S. Appl. No. 12/528,055 Office Action dated Jun. 27, 2011.
U.S. Appl. No. 12/528,055 Office Action dated Mar. 1, 2016.
U.S. Appl. No. 12/528,055 Office Action dated Mar. 27, 2012.
U.S. Appl. No. 12/528,055 Restriction Requirement dated Apr. 6, 2011.
U.S. Appl. No. 12/528,668 Final Office Action dated Mar. 21, 2012.
U.S. Appl. No. 12/528,668 Non-Final Office Action dated Sep. 25, 2013.
U.S. Appl. No. 12/528,668 Office Action dated Sep. 2, 2011.
U.S. Appl. No. 12/528,668 Restriction Requirement dated May 18, 2011.
U.S. Appl. No. 12/529,106 Office Action dated Oct. 14, 2011.
U.S. Appl. No. 12/530,390 Office Action dated Mar. 25, 2011.

(56) References Cited

OTHER PUBLICATIONS

U.S. Appl. No. 12/599,549 Office Action dated Apr. 26, 2011.
U.S. Appl. No. 12/675,718 Office Action dated Feb. 6, 2013.
U.S. Appl. No. 12/675,718 Restriction Requirement dated Aug. 7, 2012.
U.S. Appl. No. 13/130,998 Office Action dated Apr. 2, 2018.
U.S. Appl. No. 13/130,998 Office Action dated Apr. 29, 2015.
U.S. Appl. No. 13/130,998 Office Action dated Aug. 14, 2015.
U.S. Appl. No. 13/130,998 Office Action dated Feb. 21, 2017.
U.S. Appl. No. 13/130,998 Office Action dated Feb. 4, 2014.
U.S. Appl. No. 13/130,998 Office Action dated Jun. 13, 2016.
U.S. Appl. No. 13/130,998 Office Action dated Oct. 4, 2017.
U.S. Appl. No. 13/130,998 Office Action dated Sep. 16, 2013.
U.S. Appl. No. 13/140,874 Restriction Requirement dated Feb. 22, 2013.
U.S. Appl. No. 13/263,707 Office Action dated Apr. 6, 2015.
U.S. Appl. No. 13/263,707 Office Action dated Aug. 1, 2014.
U.S. Appl. No. 13/263,707 Office Action dated Dec. 22, 2015.
U.S. Appl. No. 13/263,707 Office Action dated Feb. 26, 2014.
U.S. Appl. No. 13/263,707 Office Action dated Jul. 6, 2017.
U.S. Appl. No. 13/263,707 Office Action dated Jun. 19, 2013.
U.S. Appl. No. 13/263,707 Office Action dated Jun. 27, 2016.
U.S. Appl. No. 13/263,707 Office Action dated Nov. 28, 2016.
U.S. Appl. No. 13/263,707 Office Action dated Sep. 17, 2018.
U.S. Appl. No. 13/372,359 Office Action dated Jan. 12, 2016.
U.S. Appl. No. 13/372,359 Office Action dated Jan. 23, 2015.
U.S. Appl. No. 13/372,359 Office Action dated Jul. 21, 2016.
U.S. Appl. No. 13/372,359 Office Action dated Jul. 27, 2015.
U.S. Appl. No. 13/372,359 Office Action dated Jun. 23, 2014.
U.S. Appl. No. 13/372,359 Office Action dated Jun. 8, 2017.
U.S. Appl. No. 13/372,359 Office Action dated Nov. 17, 2016.
U.S. Appl. No. 14/722,018 Office Action dated May 12, 2017.
U.S. Appl. No. 14/722,018 Office Action dated Nov. 14, 2017.
U.S. Appl. No. 14/779,893 Final Office Action dated Apr. 26, 2019.
U.S. Appl. No. 14/779,893 Office Action dated Jul. 5, 2017.
U.S. Appl. No. 14/779,893 Office Action dated Mar. 21, 2018.
U.S. Appl. No. 14/779,893 Office Action dated Sep. 12, 2019.
U.S. Appl. No. 14/779,893 Office Action dated Sep. 7, 2018.
U.S. Appl. No. 14/847,705 Office Action dated Sep. 8, 2017.
U.S. Appl. No. 14/890,699 Office Action dated Mar. 7, 2018.
U.S. Appl. No. 14/890,699 Office Action dated May 19, 2017.
U.S. Appl. No. 14/890,712 Office Action dated Dec. 6, 2017.
U.S. Appl. No. 14/900,024 Office Action dated Apr. 16, 2018.
U.S. Appl. No. 14/915,544 Office Action dated Mar. 22, 2018.
U.S. Appl. No. 15/245,875 Office Action dated Jan. 18, 2018.
U.S. Appl. No. 15/245,875 Office Action dated Jun. 12, 2018.
U.S. Appl. No. 15/557,213 Restriction Requirement dated May 21, 2019.
U.S. Appl. No. 15/792,266 Office Action dated Aug. 6, 2018.
U.S. Appl. No. 15/868,763 Final Office Action dated Oct. 1, 2019.
U.S. Appl. No. 15/868,763 Office Action dated Feb. 21, 2019.
U.S. Appl. No. 15/868,763 Restriction Requirement dated Dec. 6, 2018.
Udalova et al.: Highly informative typing of the human TNF locus using six adjacent polymorphic markers Genomics 16:180-186 (1993).
UniprotKB Database, Q8NI17 (IL31R_Human), Retrieved online Sep. 5, 2019. Retrieved from<url https://www.uniprot.org/uniprot/Q8NI17>. Jul. 31, 2019</url>.
Vaidya et al.: The cytotoxic T lymphocyte antigen-4 is a major Graves' disease locus. Human Molecular Genetics 8:1195-1199 (1999).
Vasiliauskas et al.: Marker antibody expression stratifies Crohn's disease into immunologically homogeneous subgroups with distinct clinical characteristics. Gut 47:487-496 (2000).
Vasiliauskas et al.: Perinuclear antineutrophil cytoplasmic antibodies in patients with Crohn's disease define a clinical subgroups. Gastroenterology 110:1810-1819 (1996).
Vavassori et al.: CARD15 mutation analysis in an Italian population: Leu1007fsinsC but neither Arg702Trp norGly908Arg mutations are associated with Crohn's disease. Inflamm Bowel Dis 10:116-121 (2004).
Verdu et al.: Modulatory effects of estrogen in two murine models of experimental colitis. American J Physiology 283:G27-G36 (2002).
Verhoeyen et al. Reshaping human antibodies: Grafting an antilysozyme activity. Science 239:1534-1536, 1988.
Vermeire et al.: Current Status of Genetics Research in Inflammatory Bowel Disease, Genes and Immunity, 2005, vol. 6, pp. 637-645.
Vermiere et al.: CARD15 genetic variation in a Quebec population: prevalence, genotype-phenotype relationship and haplotype structure. Am J Hum Genet 71:74-83 (2002).
Verthelyi et al. Sex hormone levels correlate with the activity of cytokine-secreting cells in vivo. Immunology 100:384-390 (2000).
Voraberger et al.: Cloning on the human gene for intercellular adhesion molecule-1 and analysis of its 5'-regulatory region. J Immunol 147:2777-2786 (1991).
Walder et al. Oligodeoxynucleotide-directed mutagenesis using the yeast transformation system. Gene 42:133-139, 1986.
Wall et al.: Transgenic Dairy Cattle: Genetic Engineering on a Large Scale, J. Dairy Sci, 80:2213-2224, 1997.
Wang et al.: Diverse Genome-Wide Association Studies Associate the IL12/IL23 pathway with Crohn Disease, Am J. Hum. Genet., 2009, vol. 84(3), pp. 399-405.
Ward et al. Binding activities of a repertoire of single immunoglobulin variable domains secreted from *Escherichia coli*. Nature 334:544-54, 1989.
Warzocha et al.: Tumor necrosis factor ligand receptor system can predict treatment outcome of lymphoma patients. Journal of Clinical Oncology 15:499-508 (1997).
Webb et al.: Genetic variability at the human tumor necrosis factor loci. J. Immunol 145:1278-1285 (1993).
Weber et al. Abundant class of human DNA polymorphisms which can be typed using the polymerase chain reaction. Am J Hum Genet 44:388-396 (1989).
Wen et al.: TL 1A-induced NF-kB activation and c-IAP2 production prevent DR3-mediated C456 apoptosis in TF-1 cells. J Biol Chem 278:39251-39258 (2003).
Whisnant et al.: Rheumatoid Arthritis: Treatment with Azathioprine (IMURAN (R)), Clinical Side-Effects and Laboratory Abnormalities, Ann Rheum Dis., 1982, vol. 41, pp. 44-47.
Williams et al.: Optimization strategies for the polymerase chain reaction. Biotechniques 7:762-768 (1989).
Wouters et al.: Inter- and intra-individual variation of endotoxin- and beta (1-3)-glucan-induced cytokine responses in a whole blood assay. Toxicology and Industrial Health 18:15-27 (2002).
Wu et al. Tamoxifen alleviates disease severity and decreases double negative T cells in autoimmune MRL-Ipr/Ipr mice. Immunology 100:110-118 (2000).
Wu et al.: Genome-wide gene expression differences in Crohn's disease and ulcerative colitis from endoscopic pinch biopsies: Insights into distinctive pathogenesis. Inflammatory Bowel Disease, 13:807-821, 2007.
Wu et al.: Tamoxifen decreases renal inflammation and alleviates disease severity in autoimmune NZBIW F1 mice. Scandinavian Journal of Immunology 52:393-400 (2000).
Xiao et al.: Interaction of Cocksackievirus A21 with its cellular receptor ICAM-1. J Viral 75:2444-2451 (2001).
Yagi et al.: Interleukin-31 stimulates production of inflammatory mediators from human colonic subepithelial myofibroblasts. International Journal of Molecular Medicine, 19:941-946, 2007.
Yamamoto-Furusho et al.: Complotype SC30 is associated with susceptibility to develop severe C462 ulcerative colitis in Mexicans. J Clin Gasterol 27:178-180 (1998).
Yamazaki et al.: Absence of mutation in the NOD2/CARD15 gene among 483 Japanese patients with Crohn's disease. Hum Mol Genet 47:469-472 (2002).
Yamazaki et al.: Association analysis of genetic variants in IL23R, ATG16L 1 and 5p13.1 loci with Crohn's disease in Japanese patients. J Hum Genet 52:575-582 (2007).

(56) References Cited

OTHER PUBLICATIONS

Yamazaki et al.: Single nucleotide polymorphisms in TNFSF15 confers susceptibility to Crohn's disease. Hum Mol Genet 14:3499-3506 (2005).

Yang et al. Genetic aspects of idiopathic inflammatory bowel disease. Kirschner and Shorter (Eds.), Inflammatory Bowel Disease Baltimore: Williams and Wilkins pp. 301-331 (1995).

Yang et al. The R241 allele of ICAM-1 is associated with a distinct clinical subgroup of Crohn's disease (CD) characterized by perinuclear ANCA (pANCA) production. Abstract only. American Gastroenterological Association and American Association for the study of Liver disease. May 19-22, 1996.

Yang et al.: Association of intercellular adhesion molecule-1 (ICAM-1) gene with subsets of Inflammatory Bowel Disease (IBO) stratified by anti-neutrophil cytoplasmic antibodies I (AN CAs). Clinical Research Abstract only 42(1):76A (1994).

Yang et al.: Familial empirical risks for inflammatory bowel disease: differences between Jews and non-Jews. Gut 34:517-524 (1993).

Yang et al.: Genetic Heterogeneity within UC and Crohn's disease defined by anti-neutrophil cytoplasmic antibodies (AN CAs) and intercellular adhesion molecule-1 (ICAM-1) polymorph isms. Gastroenterology 106(4):A794 AGA Abstract (1994).

Yang et al.: Intercellular adhesion molecule 1 gene association with immunologic subsets of inflammatory bowel disease. Gastroenterology 109:440-448 (1995).

Yang et al.: Linkage of Crohn's disease to the major histocompatibility complex region is detected by multiple non-parametric analyses. Gut. 44 p. 519-526 (1999).

Yang et al.: Ulcerative colitis: a genetically heterogenous disorder defined by genetic (HLA class II) and subclinical (antineutrophil cytoplasmic antibodies) markers J. Clin. Invest., 92:1080-1084 (1993).

Yang, Suk-Kyun et al.: Association of TNFSF15 with Crohn's Disease in Koreans, American Journal of Gastroenterology 2008;103:1437-1442.

Yeager et al.: Genome-wide association study of prostate cancer identifies a second risk locus at 8q24. Nature Genetics, 39(5):645-649, 2007.

Yoon et al. Colonic Phenotypes Are Associated with Poorer Response to Anti-TNF Therapies in Patients with IBD. Inflammatory Bowel Diseases. 23(8):1382-1393 (2017).

Yoon et al.: Decreased potency of the Vibrio cholerae sheathed flagellum to trigger host innate immunity. Infection and Immunity 76:1282-1288 (2008).

Younes et al.: Clinical implication of the tumor necrosis factor family in benign and malignant hematologic disorders. Cancer 98:458-467 (2003).

Younes et al.: Emerging applications of the tumor necrosis factor family if ligands and receptors in cancer therapy. J Clin Oncol 21:3526-3534, (2003).

Zaahl et al.: Analysis of the three common mutations in the CARD15 gene (R702W, G908R and 1007fs) in South African colored patients with inflammatory bowel disease. Molecular and Cellular Probes 19:278-281 (2005).

Zhang et al. Estrogen affects the differentiation and function of splenic monocyte-derived dendritic cells from normal rats. Abstract Only. 20:129-134 (2004).

Zhang et al.: Critical role of IL-17 receptor signaling in acute TNBS-induced colitis. Inflamm Bowel Dis 12:382-388 (2006).

Ziegler et al.: Detectable serum flagellin and liposaccharide and upregulated anti-flagellin and liposaccharide immunoglobulins in human short bowel syndrome. Am J Physiol Regul IntegrComp Physiol. 294:R402-R410 (2008).

Zill et al.: SNP and Haplotype Analysis of a Novel Tryptophan Hydroxylase Isoform (TPH2) Gene Provide Evidence for Association with Major Depression, Molecular Psychiatry, 2004, vol. 9, pp. 1030-1036.

Andoh et al.: Mucosal cytokine network in inflammatory bowel disease. World J Gastroenterol. 14(33):5154-5161 (2008).

Benner et al.: Evolution, Language and Analogy in Functional Genomics, Trends in Genetics, 2001, vol. 17, pp. 414-418.

Burke et al.: Transcriptomic analysis of intestinal fibrosis-associated gene expression in response to medical therapy in Crohn's disease. Inflammatory Bowel Diseases. 14(9):1197-1204 (2008).

Cho. The Genetics and Immunopathogenesis of Inflammatory Bowel Disease, Nature Reviews, 2008, vol. 8, pp. 158-466.

Dambacher et al.: Interleukin 31 mediates MAP kinase and STAT1/3 activation in intestinal epithelial cells and its expression is upregulated in inflammatory bowel disease. GUT. 56:1257-1265 (2007).

DbSNP Short Genetic Variations. Submitted SNP (ss) Details: ss566368983. NCBI. Uploaded Nov. 22, 2012. Retrieved Aug. 6, 2020. URL: https://www.ncbi.nlm.nih.gov/projects/SNP/snp_ss.cgi?subsnp_id=566368983.

Dermot et al.: Genetic epistasis of IL23/IL17 pathway genes in Crohn's disease. Inflamm Bowel Dis. 15(6):883-889 (2009).

Devlin et al.: The p631 H variant of the TLR2 gene associated with sera-reactivity to microbial antigens in Jewish patients with Crohn's disease. Abstract Only (2007) Journal unknown.

Dubinsky et al.: Increased immune reactivity predicts aggressive complicating Crohn's disease in children. Abstract only (2007) Journal unknown.

Email from James Jenkins referencing the "Amazon.com" website regarding exact publication date of "Immune Mechanism in Inflammatory Bowel Disease", edited by Richard S. Blumberg and Markus F. Neurath; Springer first edition. 2 Pages.

European Patent Application No. 19199149.6 Extended European Search Report dated Mar. 20, 2020.

European Patent Application No. EP14773989.0 Strawman Limited Opposition Against EP2978440 dated Jul. 1, 2020.

Fleshner et al.: Both preoperative pANCA and CBir1 flagellin expression in ulcerative colitis (UC) patients influence pouchitis development after illegal pouch-anal anastomosis (IPAA). Abstract only (2006) Journal unknown.

International Search Report for PCT/US2011/028694 dated Jul. 27, 2011.

Melmed et al.: A prospective analysis of predictive factors for the diagnosis of Crohn's disease after Ileal pouch-anal anastomosis for ulcerative colitis. Abstract only. (2007) Journal Unknown.

Papadakis et al.: Dominant Role for TL1A/DR3 Pathway in IL-12 plus IL-18-lnduced IFN-γ Production by Peripheral Blood and Mucosal CCR9+ T Lymphocytes, the Journal of Immunology. 174:4985-4900 (2005).

Reference SNP (refSNP) Cluster Report: rs598672, pp. 1-4 printed from http://www.ncbi.nlm.nih.gov (2020).

Reference SNP (refSNP) Cluster Report: rs666595, pp. 1-4 printed from http://www.ncbi.nlm.nih.gov (2020).

Rotter et al.: TLR5 polymorphisms are associated with OmpC and CBir1 expression and with severity of Crohn's disease in Ashkenazi Jews. Abstract only (2007). Journal unknown.

Schluender et al.: Does infliximab influence surgical morbidity or long-term outcome of Ileal pouch-anal anastomosis in patients with ulcerative colitis. Abstract only. (2006). Journal Unknown.

Schluender et al.: Does preoperative wireless endoscopic capsule predict long-term outcome after Ileal pouch-anal anastomosis (IPAA)? Abstract only. (2006). Journal unknown.

Schoelmerich. Inflammatory Bowel Diseases: early symptoms and differential (Reprints available from University of Freiburg, Department of Internal Medicine, Hugstetter Strasse 55, 0-7800 Freiburg, W. Germany pp. 2-20 (2017).

SU. Different haplotypes of IL 12B (p40) genes are associated with clinical Crohn's disease (CD) and with CD patients expressing Cbir1 antibodies, respectively. Abstract only (2007). Journal unknown.

Takedatsu. Reduced nuclear factor (NF)-kB expression in cell lines from anti-CBir1-associated NFKB1 haplotypes. Abstract only. (2007). Journal unknown.

Thisteda. What is a P-value. Departments of Statistics and Health Studies. The University of Chicago. (May 25, 1988).

Torres et al.: Newborn screening for Hermansky-pudlak syndrome Type 3 in Puerto Rico. Blood 108:3290 (2006).

U.S. Appl. No. 15/921,160 Office Action dated Feb. 27, 2020.

U.S. Appl. No. 15/946,632 Office Action dated May 1, 2020.

(56) References Cited

OTHER PUBLICATIONS

U.S. Appl. No. 15/946,632 Restriction Requirement dated Nov. 22, 2019.
U.S. Appl. No. 16/025,769 Office Action dated Jul. 6, 2020.
U.S. Appl. No. 16/025,769 Restriction Requirement dated Feb. 11, 2020.
U.S. Appl. No. 16/084,858 Restriction Requirement dated May 26, 2020.
U.S. Appl. No. 16/355,376 Restriction Requirement dated Jun. 5, 2020.
Written Opinion for PCT/US2011/028694 dated Jul. 27, 2011.
Zhang et al.: Structures and biological functions of IL-31 and IL-31 receptors. Cytokine Growth Factor. 19(5-6):347-356 (2008).
Zheng et al.: 2013 AGA Abstracts 2013 144 5 Supplement 1: p. S-132; Abstract 735 (2013).
Zheng et al.: Dynamic expression and significance of IL-31 in the process of pulmonary fibrosis in experimental mice. Shadong Medical Journal. 49(13):26-27 (2009).
Zheng et al.: Sustained TL1A (TNFSF15) Expression on both Lymphoid and Myeloid Cells Leads to Mild Spontaneous Intestinal Inflammation and Fibrosis. European Journal of Microbiology and Immunology 3(1):11-20 (2013).
Prometheus Biosciences, Inc. Form S-1 Registration Statement as filed with the Securities and Exchange Commission on Feb. 19, 2021 (246 pages).

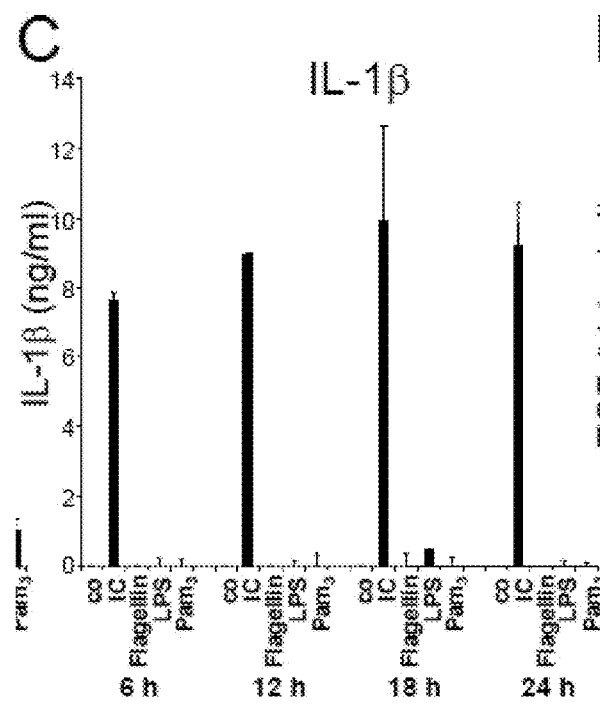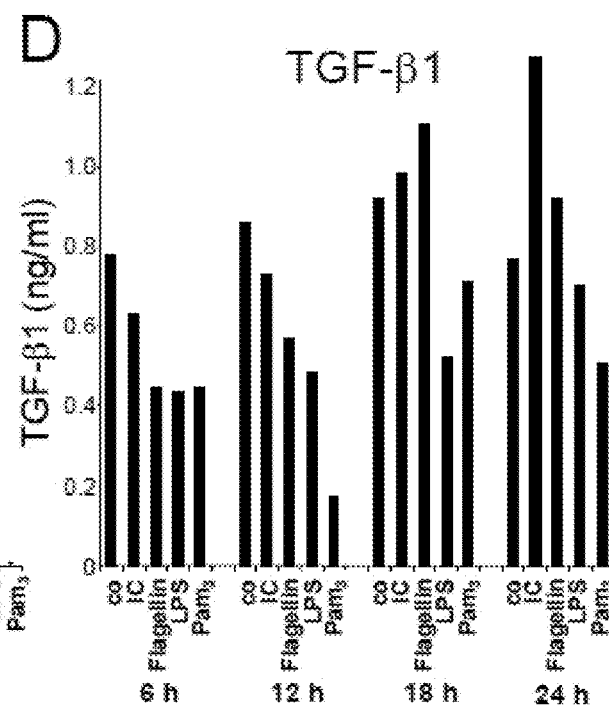
FIG. 2C                    FIG. 2D

TGFβ-1:

Probe: CCA CTT CCA GCC GAG GTC CTT GCG (SEQ ID NO: 1)

Prim(S): GCT CCA CGG AGA AGA ACT GC (SEQ ID NO: 2)

Prim(AS): GTT GGC ATG GTA GCC CTT GG (SEQ ID NO: 3)

IL-23p19:

Probe: CTG CTG TTG CTG CTG CCC TGG ACA (SEQ ID NO: 4)

Prim(S): GCT GGG GAG CAG AGC TGT AA (SEQ ID NO: 5)

Prim(AS): CTT CTG TGA AAG CTG CTG GCA (SEQ ID NO: 6)

IL-12p40:

Probe: ACC ACA AGC ATG AGC CAC CAC GCC (SEQ ID NO: 7)

Prim(S): AGC TGG GAA ACA TAA CAG ACC (SEQ ID NO: 8)

Prim(AS): TCC TGC CTC ATC CTC CTG AAC (SEQ ID NO: 9)

IL-6

Probe: CTG CTC CTG GTG TTG CCT GCT GCC (SEQ ID NO: 10)

Prim(S): CTT CGG TCC AGT TGC CTT CTC (SEQ ID NO: 11)

Prim(AS): AAG AGG TGA GTG GCT GTC TGT (SEQ ID NO: 12)

IL-1β

Probe: ACA CCA ATG CCC AAC TGC CTG CCT (SEQ ID NO: 13)

Prim(S): TAT AGC CTG GAC TTT CCT GTT GTC (SEQ ID NO: 14)

Prim(AS): GCT GAC TGT CCT GGC TGA TG (SEQ ID NO: 15)

TL1A

Probe: ACC TGC TTG TCA GCC AGC TCC GG (SEQ ID NO: 16)

Prim(S): CTT CCT TGC AGG ACT CAC CAC (SEQ ID NO: 17)

Prim(AS): GCT GAT GTG AAG GTG CAA ACT C (SEQ ID NO: 18)

FIG. 25A

β-Actin

Probe: CGG CTA CAG CTT CAC CAC CAC GGC (SEQ ID NO: 19)

Prim(S): GAC TAC CTC ATG AAG ATC CTC ACC (SEQ ID NO: 20)

Prim(AS): TCT CCT TAA TGT CAC GCA CGA TT (SEQ ID NO: 21)

IL-17A

Probe: TCT CAG GGT CCT CAT TGC GGC TGC (SEQ ID NO: 22)

Prim(S): AAC TTG CCT CTC TTC ATG TAT TCC (SEQ ID NO: 23)

Prim(AS): ACT TTG CCT CCC AGA TCA CAG (SEQ ID NO: 24)

RORA

Probe: TTG ATG GGA AGT ATG CCA GC (SEQ ID NO: 25)

Prim(S): CGG TGC CTT TGA CTC TCA GAA CAA CAC CG (SEQ ID NO: 26)

Prim(AS) TCT TTC CAA ATT CAA ACA CAA AGC (SEQ ID NO: 27)

Tbet

Probe: TCC GCC GTC CCT GCT TGG TGA TGA (SEQ ID NO: 28)

Prim(S): CCA AGT TTA ATC AGC ACC AGA CAG (SEQ ID NO: 29)

Prim(AS) GCC ACA GTA AAT GAC AGG AAT GG (SEQ ID NO: 30)

FIG. 25B

| Pvalue | Gene ID | Gene Name |
|---|---|---|
| 1.27E-05 | SNORA66 | Homo sapiens small nucleolar RNA, H/ACA box 66 (SNORA66), non-coding RNA. |
| 0.009469 | LY75 | Homo sapiens lymphocyte antigen 75 (LY75), mRNA. |
| 0.004433 | DKFZp434N035 | Homo sapiens hypothetical protein DKFZp434N035 (DKFZp434N035), mRNA. |
| 0.001976 | PCBP4 | Homo sapiens poly(rC) binding protein 4 (PCBP4), transcript variant 2, mRNA. |
| 0.009986 | OR8K5 | Homo sapiens olfactory receptor, family 8, subfamily K, member 5 (OR8K5), mRNA. |
| 0.005017 | HMGA2 | Homo sapiens high mobility group AT-hook 2 (HMGA2), transcript variant 2, mRNA. |
| 3.23E-05 | RNASEN | Homo sapiens ribonuclease III, nuclear (RNASEN), mRNA. |
| 0.040618 | KIAA0513 | Homo sapiens KIAA0513 (KIAA0513), mRNA. |
| 0.000231 | SOCS7 | Homo sapiens suppressor of cytokine signaling 7 (SOCS7), mRNA. |
| 0.003355 | GABBR1 | Homo sapiens gamma-aminobutyric acid (GABA) B receptor, 1 (GABBR1), transcript variant 2, mRNA. |
| 0.021163 | SYNJ1 | Homo sapiens synaptojanin 1 (SYNJ1), transcript variant 2, mRNA. |
| 0.027361 | BEND3 | Homo sapiens BEN domain containing 3 (BEND3), mRNA. |
| 0.001002 | CTNND1 | PREDICTED: Homo sapiens catenin (cadherin-associated protein), delta 1, transcript variant 3 (CTNND1), mRNA. |
| 0.012461 | TMEM50B | Homo sapiens transmembrane protein 50B (TMEM50B), mRNA. |
| 0.049772 | ERI3 | Homo sapiens ERI1 exoribonuclease family member 3 (ERI3), mRNA. |
| 0.032492 | HGSNAT | Homo sapiens heparan-alpha-glucosaminide N-acetyltransferase (HGSNAT), mRNA. |
| 0.014929 | OPN4 | Homo sapiens opsin 4 (OPN4), transcript variant 1, mRNA. |
| 0.009838 | PHF14 | Homo sapiens PHD finger protein 14 (PHF14), transcript variant 1, mRNA. |
| 0.012597 | TNRC18 | PREDICTED: Homo sapiens trinucleotide repeat containing 18 (TNRC18), mRNA. |
| 0.001887 | RPL10L | Homo sapiens ribosomal protein L10-like (RPL10L), mRNA. |
| 0.046308 | BRWD1 | Homo sapiens bromodomain and WD repeat domain containing 1 (BRWD1), transcript variant 2, mRNA. |
| 0.002598 | CEBPA | Homo sapiens CCAAT/enhancer binding protein (C/EBP), alpha (CEBPA), mRNA. |
| 0.003782 | DIO3 | Homo sapiens deiodinase, iodothyronine, type III (DIO3), mRNA. |
| 0.00355 | TAS1R2 | PREDICTED: Homo sapiens taste receptor, type 1, member 2 (TAS1R2), mRNA. |
| 0.00027 | PLGLB2 | Homo sapiens plasminogen-like B2 (PLGLB2), mRNA. |
| 0.018571 | FLJ45966 | Homo sapiens FLJ45966 protein (FLJ45966), mRNA. |
| 0.002224 | KLHDC7A | Homo sapiens kelch domain containing 7A (KLHDC7A), mRNA. |
| 0.010895 | IFIT1 | Homo sapiens interferon-induced protein with tetratricopeptide repeats 1 (IFIT1), transcript variant 2, mRNA. |
| 0.012235 | KCNK4 | Homo sapiens potassium channel, subfamily K, member 4 (KCNK4), transcript variant 1, mRNA. |
| 0.011332 | SUZ12P | PREDICTED: Homo sapiens suppressor of zeste 12 homolog pseudogene, transcript variant 3 (SUZ12P), mRNA. |
| 0.000885 | SPRR2D | Homo sapiens small proline-rich protein 2D (SPRR2D), mRNA. |
| 0.014648 | FMO2 | Homo sapiens flavin containing monooxygenase 2 (non-functional) (FMO2), mRNA. |
| 0.014898 | KIT | Homo sapiens v-kit Hardy-Zuckerman 4 feline sarcoma viral oncogene homolog (KIT), transcript variant 2, mRNA. |

FIG. 26A

| Pvalue | Gene ID | Gene Name |
|---|---|---|
| 0.038861 | KLK10 | Homo sapiens kallikrein 10 (KLK10), transcript variant 1, mRNA. |
| 0.000208 | PWWP2 | Homo sapiens PWWP domain containing 2 (PWWP2), mRNA. |
| 0.015429 | PLD3 | Homo sapiens phospholipase D family, member 3 (PLD3), transcript variant 2, mRNA. |
| 0.026949 | APBB1 | Homo sapiens amyloid beta (A4) precursor protein-binding, family B, member 1 (Fe65) (APBB1), transcript variant 2, mRNA. |
| 0.045088 | ZNF43 | Homo sapiens zinc finger protein 43 (ZNF43), mRNA. |
| 0.000463 | KIAA1160 | PREDICTED: Homo sapiens KIAA1160 protein (KIAA1160), mRNA. |
| 0.00369 | SCARNA21 | Homo sapiens small Cajal body-specific RNA 21 (SCARNA21), guide RNA. |
| 0.019536 | APLF | Homo sapiens aprataxin and PNKP like factor (APLF), mRNA. |
| 0.036943 | LRRC44 | Homo sapiens leucine rich repeat containing 44 (LRRC44), mRNA. |
| 0.034074 | CLCF1 | Homo sapiens cardiotrophin-like cytokine factor 1 (CLCF1), transcript variant 1, mRNA. |
| 0.023129 | PRY | Homo sapiens PTPN13-like, Y-linked (PRY), mRNA. |
| 0.007292 | OR51F1 | Homo sapiens olfactory receptor, family 51, subfamily F, member 1 (OR51F1), mRNA. |
| 0.0113 | TRY1 | Homo sapiens trypsin X3 (TRY1), mRNA. |
| 0.043149 | ATP6V1H | Homo sapiens ATPase, H+ transporting, lysosomal 50/57kDa, V1 subunit H (ATP6V1H), transcript variant 3, mRNA. |
| 0.011583 | FLJ30719 | PREDICTED: Homo sapiens hypothetical protein FLJ30719 (FLJ30719), misc RNA. |
| 0.02057 | ZNF716 | PREDICTED: Homo sapiens zinc finger protein 716 (ZNF716), mRNA. |
| 0.005197 | JRK | Homo sapiens jerky homolog (mouse) (JRK), transcript variant 1, mRNA. |
| 0.001144 | SMPDL3B | Homo sapiens sphingomyelin phosphodiesterase, acid-like 3B (SMPDL3B), transcript variant 1, mRNA. |
| 0.042268 | RNU4-1 | Homo sapiens RNA, U4 small nuclear 1 (RNU4-1), small nuclear RNA. |
| 0.007012 | RAB24 | Homo sapiens RAB24, member RAS oncogene family (RAB24), transcript variant 2, mRNA. |
| 0.005043 | YSK4 | Homo sapiens YSK4 Sps1/Ste20-related kinase homolog (S. cerevisiae) (YSK4), transcript variant 2, mRNA. |
| 0.009059 | PIP5KL1 | Homo sapiens phosphatidylinositol-4-phosphate 5-kinase-like 1 (PIP5KL1), transcript variant 2, mRNA. |
| 0.016195 | CPLX1 | Homo sapiens complexin 1 (CPLX1), mRNA. |
| 0.041526 | KRT83 | Homo sapiens keratin 83 (KRT83), mRNA. |
| 0.035409 | CRISPLD2 | Homo sapiens cysteine-rich secretory protein LCCL domain containing 2 (CRISPLD2), mRNA. |
| 0.043923 | RUFY3 | Homo sapiens RUN and FYVE domain containing 3 (RUFY3), transcript variant 1, mRNA. |
| 0.031612 | CPZ | Homo sapiens carboxypeptidase Z (CPZ), transcript variant 1, mRNA. |
| 0.001068 | TSPAN7 | Homo sapiens tetraspanin 7 (TSPAN7), mRNA. |
| 0.023323 | PKIG | Homo sapiens protein kinase (cAMP-dependent, catalytic) inhibitor gamma (PKIG), transcript variant 2, mRNA. |
| 0.00509 | FLJ20209 | PREDICTED: Homo sapiens hypothetical protein FLJ20209 (FLJ20209), mRNA. |
| 0.011386 | SFXN5 | Homo sapiens sideroflexin 5 (SFXN5), mRNA. |
| 0.03651 | PSG4 | Homo sapiens pregnancy specific beta-1-glycoprotein 4 (PSG4), transcript variant 1, mRNA. |
| 0.00245 | ANKRD13D | PREDICTED: Homo sapiens ankyrin repeat domain 13 family, member D, transcript variant 6 (ANKRD13D), mRNA. |
| 0.023625 | ZNF708 | Homo sapiens zinc finger protein 708 (ZNF708), mRNA. |
| 0.019392 | COX18 | Homo sapiens COX18 cytochrome c oxidase assembly homolog (S. cerevisiae) (COX18), nuclear gene encoding mitochondrial protein, mRNA. |
| 0.038097 | ZFHX3 | Homo sapiens zinc finger homeobox 3 (ZFHX3), transcript variant A, mRNA. |
| 0.012734 | TIAM2 | Homo sapiens T-cell lymphoma invasion and metastasis 2 (TIAM2), transcript variant 1, mRNA. |

FIG. 26B

| Pvalue | Gene ID | Gene Name |
|---|---|---|
| 0.002232 | FLJ10120 | PREDICTED: Homo sapiens hypothetical protein FLJ10120 (FLJ10120), misc RNA. |
| 0.025843 | ABCC6 | Homo sapiens ATP-binding cassette, sub-family C (CFTR/MRP), member 6 (ABCC6), transcript variant 2, mRNA. |
| 0.04963 | FAM131C | Homo sapiens family with sequence similarity 131, member C (FAM131C), mRNA. |
| 0.039646 | PDE6G | Homo sapiens phosphodiesterase 6G, cGMP-specific, rod, gamma (PDE6G), mRNA. |
| 0.020785 | PILRB | Homo sapiens paired immunoglobin-like type 2 receptor beta (PILRB), transcript variant 3, mRNA. |
| 0.006385 | CREBBP | Homo sapiens CREB binding protein (CREBBP), transcript variant 1, mRNA. |
| 0.036262 | KCNH2 | Homo sapiens potassium voltage-gated channel, subfamily H (eag-related), member 2 (KCNH2), transcript variant 2, mRNA. |
| 0.006474 | KIAA1632 | Homo sapiens KIAA1632 (KIAA1632), mRNA. |
| 0.045934 | MGC40499 | PREDICTED: Homo sapiens PRotein Associated with Tlr4, transcript variant 4 (MGC40499), mRNA. |
| 0.005964 | CES1 | Homo sapiens carboxylesterase 1 (monocyte/macrophage serine esterase 1) (CES1), transcript variant 1, mRNA. |
| 0.011063 | PAGE3 | Homo sapiens P antigen family, member 3 (prostate associated) (PAGE3), mRNA. |
| 0.035848 | MLN | Homo sapiens motilin (MLN), transcript variant 2, mRNA. |
| 0.003557 | TNRC6B | Homo sapiens trinucleotide repeat containing 6B (TNRC6B), transcript variant 3, mRNA. |
| 0.046621 | RNU5A | Homo sapiens RNA, U5A small nuclear (RNU5A), small nuclear RNA. |
| 0.015552 | SNORA48 | Homo sapiens small nucleolar RNA, H/ACA box 48 (SNORA48), small nucleolar RNA. |
| 0.039545 | GRIK5 | Homo sapiens glutamate receptor, ionotropic, kainate 5 (GRIK5), mRNA. |
| 0.043899 | CXXC4 | Homo sapiens CXXC finger 4 (CXXC4), mRNA. |
| 0.006098 | MFAP5 | Homo sapiens microfibrillar associated protein 5 (MFAP5), mRNA. |
| 0.014215 | BTRC | Homo sapiens beta-transducin repeat containing (BTRC), transcript variant 1, mRNA. |
| 0.036117 | VEGFB | Homo sapiens vascular endothelial growth factor B (VEGFB), mRNA. |

FIG. 26C

| Pvalue | Gene ID | Gene Name |
|---|---|---|
| 0.00087 | TOM1L2 | Homo sapiens target of myb1-like 2 (chicken) (TOM1L2), transcript variant 3, mRNA. |
| 0.022932 | FAM27L | Homo sapiens family with sequence similarity 27-like (FAM27L), mRNA. |
| 0.015543 | EPS8L3 | Homo sapiens EPS8-like 3 (EPS8L3), transcript variant 3, mRNA. |
| 0.009413 | SAPS2 | PREDICTED: Homo sapiens SAPS domain family, member 2, transcript variant 6 (SAPS2), mRNA. |
| 0.040276 | DNMT3A | Homo sapiens DNA (cytosine-5-)-methyltransferase 3 alpha (DNMT3A), transcript variant 2, mRNA. |
| 0.024134 | NTRK2 | Homo sapiens neurotrophic tyrosine kinase, receptor, type 2 (NTRK2), transcript variant a, mRNA. |
| 0.031189 | ZNF699 | Homo sapiens zinc finger protein 699 (ZNF699), mRNA. |
| 0.011412 | KIAA1666 | PREDICTED: Homo sapiens KIAA1666 protein (KIAA1666), mRNA. |
| 0.036996 | GNG11 | Homo sapiens guanine nucleotide binding protein (G protein), gamma 11 (GNG11), mRNA. |
| 0.022617 | CDAN1 | PREDICTED: Homo sapiens congenital dyserythropoietic anemia, type I (CDAN1), mRNA. |
| 0.000201 | LRP1B | Homo sapiens low density lipoprotein-related protein 1B (deleted in tumors) (LRP1B), mRNA. |
| 0.011592 | TRIM63 | Homo sapiens tripartite motif-containing 63 (TRIM63), mRNA. |
| 0.016413 | PDPN | Homo sapiens podoplanin (PDPN), transcript variant 4, mRNA. |
| 0.048523 | SYT2 | Homo sapiens synaptotagmin II (SYT2), mRNA. |
| 0.005882 | ZCCHC10 | Homo sapiens zinc finger, CCHC domain containing 10 (ZCCHC10), mRNA. |
| 0.022318 | CD86 | Homo sapiens CD86 antigen (CD28 antigen ligand 2, B7-2 antigen) (CD86), transcript variant 1, mRNA. |
| 0.005589 | ADCY8 | Homo sapiens adenylate cyclase 8 (brain) (ADCY8), mRNA. |
| 0.0384 | PHF21B | Homo sapiens PHD finger protein 21B (PHF21B), mRNA. |
| 0.00977 | LDB3 | Homo sapiens LIM domain binding 3 (LDB3), transcript variant 4, mRNA. |
| 0.002275 | BRUNOL4 | PREDICTED: Homo sapiens bruno-like 4, RNA binding protein (Drosophila) (BRUNOL4), mRNA. |
| 0.003417 | PLAC4 | Homo sapiens placenta-specific 4 (PLAC4), mRNA. |
| 0.015364 | OR4M1 | Homo sapiens olfactory receptor, family 4, subfamily M, member 1 (OR4M1), mRNA. |
| 0.007163 | MEN1 | Homo sapiens multiple endocrine neoplasia I (MEN1), transcript variant e1D, mRNA. |
| 0.02911 | LCAP | Homo sapiens lung carcinoma-associated protein (LCAP), mRNA. |
| 0.017217 | TOP1 | Homo sapiens topoisomerase (DNA) I (TOP1), mRNA. |
| 0.02383 | FBXW5 | Homo sapiens F-box and WD-40 domain protein 5 (FBXW5), transcript variant 3, mRNA. |
| 0.023057 | SNORA72 | Homo sapiens small nucleolar RNA, H/ACA box 72 (SNORA72), small nucleolar RNA. |
| 0.038346 | IL9 | Homo sapiens interleukin 9 (IL9), mRNA. |
| 0.001689 | ZNF138 | Homo sapiens zinc finger protein 138 (ZNF138), mRNA. |
| 0.049896 | CNKSR2 | Homo sapiens connector enhancer of kinase suppressor of Ras 2 (CNKSR2), mRNA. |
| 0.007055 | SNORD119 | Homo sapiens small nucleolar RNA, C/D box 119 (SNORD119), small nucleolar RNA. |

FIG. 26D

| Pvalue | Gene ID | Gene Name |
|---|---|---|
| 0.045868 | ABI3BP | Homo sapiens ABI gene family, member 3 (NESH) binding protein (ABI3BP), mRNA. |
| 0.00025 | IMAA | Homo sapiens SLC7A5 pseudogene (IMAA), non-coding RNA. |
| 0.045214 | USP45 | Homo sapiens ubiquitin specific peptidase 45 (USP45), mRNA. |
| 0.016327 | IL9 | Homo sapiens interleukin 9 (IL9), mRNA. |
| 0.000768 | REXO1L6P | PREDICTED: Homo sapiens REX1, RNA exonuclease 1 homolog (S. cerevisiae)-like 6 (pseudogene) (REXO1L6P), mRNA. |
| 0.017028 | ARFIP1 | Homo sapiens ADP-ribosylation factor interacting protein 1 (ARFIP1), transcript variant 1, mRNA. |
| 0.013672 | CYP2E1 | Homo sapiens cytochrome P450, family 2, subfamily E, polypeptide 1 (CYP2E1), mRNA. |
| 0.001664 | ENPP7 | Homo sapiens ectonucleotide pyrophosphatase/phosphodiesterase 7 (ENPP7), mRNA. |
| 0.016496 | MIR1289-1 | Homo sapiens microRNA 1289-1 (MIR1289-1), microRNA. |
| 0.016834 | IL31RA | Homo sapiens interleukin 31 receptor A (IL31RA), mRNA. |
| 0.000938 | HEPACAM | Homo sapiens hepatocyte cell adhesion molecule (HEPACAM), mRNA. |
| 0.044994 | SPO11 | Homo sapiens SPO11 meiotic protein covalently bound to DSB homolog (S. cerevisiae) (SPO11), transcript variant 2, mRNA. |
| 0.004133 | KIAA2022 | Homo sapiens KIAA2022 (KIAA2022), mRNA. |
| 0.003635 | F8 | Homo sapiens coagulation factor VIII, procoagulant component (F8), transcript variant 2, mRNA. |
| 0.005738 | ZFP64 | Homo sapiens zinc finger protein 64 homolog (mouse) (ZFP64), transcript variant 4, mRNA. |
| 0.04771 | UBE2I | Homo sapiens ubiquitin-conjugating enzyme E2I (UBC9 homolog, yeast) (UBE2I), transcript variant 3, mRNA. |
| 0.022224 | OTUD6A | Homo sapiens OTU domain containing 6A (OTUD6A), mRNA. |
| 0.029459 | TncRNA | PREDICTED: Homo sapiens trophoblast-derived noncoding RNA (TncRNA), misc RNA. |
| 0.003951 | NXNL1 | Homo sapiens nucleoredoxin-like 1 (NXNL1), mRNA. |
| 0.006146 | SCAND3 | Homo sapiens SCAN domain containing 3 (SCAND3), mRNA. |
| 0.000728 | PITX2 | Homo sapiens paired-like homeodomain 2 (PITX2), transcript variant 1, mRNA. |
| 0.000115 | P2RY6 | Homo sapiens pyrimidinergic receptor P2Y, G-protein coupled, 6 (P2RY6), transcript variant 2, mRNA. |
| 0.044557 | TNFRSF10D | Homo sapiens tumor necrosis factor receptor superfamily, member 10d, decoy with truncated death domain (TNFRSF10D), mRNA. |
| 0.0057 | MS4A7 | Homo sapiens membrane-spanning 4-domains, subfamily A, member 7 (MS4A7), transcript variant 2, mRNA. |
| 0.001418 | TMEM54 | Homo sapiens transmembrane protein 54 (TMEM54), mRNA. |
| 0.011597 | SGCA | Homo sapiens sarcoglycan, alpha (50kDa dystrophin-associated glycoprotein) (SGCA), mRNA. |
| 0.028281 | PLA1A | Homo sapiens phospholipase A1 member A (PLA1A), mRNA. |
| 0.00057 | TIAL1 | Homo sapiens TIA1 cytotoxic granule-associated RNA binding protein-like 1 (TIAL1), transcript variant 1, mRNA. |
| 0.01941 | MOBKL2C | Homo sapiens MOB1, Mps One Binder kinase activator-like 2C (yeast) (MOBKL2C), transcript variant 1, mRNA. |
| 0.000116 | CEPT1 | Homo sapiens choline/ethanolamine phosphotransferase 1 (CEPT1), transcript variant 2, mRNA. |
| 0.000429 | OR5D14 | Homo sapiens olfactory receptor, family 5, subfamily D, member 14 (OR5D14), mRNA. |

FIG. 26E

| Pvalue | Gene ID | Gene Name |
|---|---|---|
| 0.019862 | FLJ44477 | PREDICTED: Homo sapiens FLJ44477 protein (FLJ44477), miscRNA. |
| 0.043532 | LMTK2 | Homo sapiens lemur tyrosine kinase 2 (LMTK2), mRNA. |
| 0.005625 | CCL4 | Homo sapiens chemokine (C-C motif) ligand 4 (CCL4), mRNA. |
| 0.002056 | SELE | Homo sapiens selectin E (endothelial adhesion molecule 1) (SELE), mRNA. |
| 0.01949 | TAS2R41 | Homo sapiens taste receptor, type 2, member 41 (TAS2R41), mRNA. |
| 0.002456 | MRC2 | Homo sapiens mannose receptor, C type 2 (MRC2), mRNA. |
| 0.008043 | PCDHA7 | Homo sapiens protocadherin alpha 7 (PCDHA7), transcript variant 1, mRNA. |
| 0.025639 | PLAG1 | Homo sapiens pleiomorphic adenoma gene 1 (PLAG1), mRNA. |
| 7.72E-05 | CDH9 | Homo sapiens cadherin 9, type 2 (T1-cadherin) (CDH9), mRNA. |
| 0.016125 | PRRX1 | Homo sapiens paired related homeobox 1 (PRRX1), transcript variant pmx-1a, mRNA. |
| 0.002457 | GPHA2 | Homo sapiens glycoprotein hormone alpha 2 (GPHA2), mRNA. |
| 0.012469 | POTE2 | Homo sapiens protein expressed in prostate, ovary, testis, and placenta 2 (POTE2), transcript variant POTE-2B, mRNA. |
| 0.033249 | TNFRSF10B | Homo sapiens tumor necrosis factor receptor superfamily, member 10b (TNFRSF10B), transcript variant 2, mRNA. |
| 0.001018 | NR1I2 | Homo sapiens nuclear receptor subfamily 1, group I, member 2 (NR1I2), transcript variant 3, mRNA. |

FIG. 26F

SIGNATURE OF TL1A (TNFSF15) SIGNALING PATHWAY

CROSS REFERENCE TO RELATED APPLICATIONS

This application is a continuation application of U.S. application Ser. No. 14/900,024 filed on Dec. 18, 2015, now issued as U.S. Pat. No. 10,316,083 on Jun. 11, 2019, which is a national phase entry of International Patent Application No. PCT/US2014/047326 filed on Jul. 18, 2014, which claims priority to U.S. Provisional Patent Application No. 61/856,491 filed on Jul. 19, 2013, the contents of which are hereby incorporated by reference in their entirety.

STATEMENT REGARDING FEDERALLY SPONSORED RESEARCH OR DEVELOPMENT

This invention was made with government support under Grant No. DK071176 awarded by the National Institutes of Health. The government has certain rights in this invention.

SEQUENCE LISTING

The instant application contains a Sequence Listing which has been submitted in ASCII format via EFS-Web and hereby incorporated by reference in its entirety. Said ASCII copy, created on Sep. 26, 2019, is named 52388722401_SL.txt and is 5,752 bytes in size.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

TL1A is a member of the TNF superfamily, with expression of TL1A mainly confined to inflamed tissues of colon and small bowel, and is particularly expressed on gut-homing CD4+CCR9+ mucosal T cells. TL1A has been demonstrated to synergize with IL-12 and IL-18 in the stimulation of IFN-γ by peripheral CD4+ T cells and to increase IL-2 driven proliferation and IFN-γ production by peripheral T cells. TL1A mediates a strong co-stimulation of TH1 cells by enhancing IFN-gamma production by peripheral CD4+ and mucosal CCR9+ T cells. TL1A plays an important role in the development of chronic colitis, experimental autoimmune encephalymyelitis, and allergic lung inflammation by modulating TH1, TH17, and TH2 responses suggesting an important role in chronic inflammatory processes. However, the exact mechanism how TL1A enhances TH1 and TH17 responses remains to be elucidated.

BRIEF SUMMARY OF THE INVENTION

Various embodiments include a method of treating a disease, comprising obtaining a sample from a subject, assaying the sample to diagnose a disease based on the presence of TH17 cell differentiation, treating the subject by administering a therapeutically effective dosage of a composition comprising one or more inhibitors of TL1A. In another embodiment, the TH17 cell differentiation is from human naïve CD4+ T cells. In another embodiment, the disease is psoriasis, arthritis, experimental autoimmune encephalomyelitis, or colitis. In another embodiment, diagnosing the disease comprises determining the presence of a TL1A signaling profile. In another embodiment, the TL1A signaling profile comprises the presence of a downregulation of one or more genes listed in FIG. 26A-26C herein. In another embodiment, the the TL1A signaling profile comprises the presence of an upregulation of one or more genes listed in FIG. 26D-26F herein. In another embodiment, the one or more inhibitors of TL1A is an inhibitor of the DR3 receptor. In another embodiment, the disease is intestinal inflammation.

Other embodiments include a method of treating an inflammatory disease in a subject, comprising determining the presence of a TL1A signaling profile in a subject, and treating the inflammatory disease by inhibiting TH17 differentiation from CD4+ T cells. In another embodiment, the TL1A signaling profile comprises the presence of a downregulation of one or more genes listed in FIG. 26A-26C herein. In another embodiment, the TL1A signaling profile comprises the presence of an upregulation of one or more genes listed in FIG. 26D-26F herein. In another embodiment, inhibiting TH17 differentiation comprises administering one or more inhibitors of TL1A. In another embodiment, inhibiting TH17 differentiation further comprises inhibiting IL17 secretion from TH17 cells.

Other embodiments include a method of diagnosing a disease in a subject, comprising: obtaining a sample from the subject, subjecting the sample to an assay adapted to determine the presence or absence of elevated TL1A expression and/or one or more TL1A genetic risk variants, and diagnosing the disease based on the presence of elevated TL1A expression and/or one or more TL1A genetic risk variants in the subject. In another embodiment, the subject is human. In another embodiment, the subject is Asian. In another embodiment, the subject has one or more Th17 signature cytokines elevated. In another embodiment, the sample is taken from the peripheral blood and/or intestinal biopsy of the subject. In another embodiment, the Th17 signature cytokines include IL-17, IL-22 and/or IL-9. In another embodiment, the disease is an inflammatory disease. In another embodiment, the disease is inflammatory bowel disease (IBD). In another embodiment, the disease is rheumatoid arthritis. In another embodiment, further comprising determining the presence of a TL1A signaling profile. In another embodiment, the TL1A signaling profile comprises TL1A stimulation resulting in a downregulation of one or more genes listed in FIG. 26A-26C herein, and/or an upregulation of one or more genes listed in FIG. 26D-26F herein.

Various embodiments include a method of treating an inflammatory condition in a subject, comprising determining the presence of elevated TL1A expression, Th17 signature cytokines, and/or one or more TL1A genetic risk variants in the subject, and treating the inflammatory condition in the subject. In another embodiment, the subject is human. In another embodiment, the subject is Asian. In another embodiment, the inflammatory condition is inflammatory bowel disease. In another embodiment, the inflammatory condition is treated by administering a therapeutically effective dosage of inhibitor of TL1A and/or inhibitor of one or more Th17 signature cytokines. In another embodiment, the one or more Th17 signature cytokines include IL-17, IL-22 and/or IL-9. In another embodiment, the treatment is administered in conjunction with an anti-inflammatory therapeutic.

In another embodiment, the treatment is administered by direct injection to the subject.

Other embodiments include a composition comprising a therapeutically effective dosage of inhibitor of TL1A and/or inhibitor of Th17 signature cytokines, and an acceptable carrier. In another embodiment, the inhibitor of TL1A is a TL1A antibody.

Various embodiments include a method of treating a disease in a subject, comprising providing a composition comprising a therapeutically effective dosage of inhibitor of TL1A and/or inhibitor of Th17 signature cytokines, and administering the composition to the subject. In another embodiment, the subject is human. In another embodiment, the disease is Inflammatory Bowel Disease (IBD). In another embodiment, the disease is arthritis. In another embodiment, the composition is administered in conjunction with treatment for inflammation.

Other features and advantages of the invention will become apparent from the following detailed description, taken in conjunction with the accompanying drawings, which illustrate, by way of example, various embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

(FIG. 1A) TL1A and (FIG. 1B) TGF-β1 expression in monocytes after 16 h stimulation. (FIG. 1C) Time-course of TGF-β1 expression in monocytes stimulated with the indicated ligands. (FIGS. 1D-1G) Time-course of cytokine expression in monocytes stimulated with IC. One out of four representative experiments is shown.

FIGS. 2A-2D depict, in accordance with embodiments herein, FcγR stimulation in monocytes induces secretion of cytokines that favor the development of TH17 cells. Monocytes were stimulated with IC, LPS, Pam3, IFN-γ, Flagellin, or anti-CD40 Ab for the indicated time points. Secretion of various cytokines was analyzed by ELISA. (FIG. 2A) Time-course of TL1A expression, (FIG. 2B) Time course of IL-6 expression, (FIG. 2C) Time course of IL-1β expression, (FIG. 2D) Time course of TGF-β1 expression.

(FIGS. 3A-3C) Naïve CD4+ CD45RA+ human T cells were stimulated with plate-bound anti-CD3 and anti-CD28 antibodies with the addition of the indicated cytokines for 72 h. Culture supernatants were analyzed for IL-17 (FIG. 3A), IFNγ (FIG. 3B), IL-22 (FIG. 3C) after 72 h by ELISA. One representative experiment out of at least four independent experiments with similar results is shown. (FIGS. 3D-3G) Naïve CD4+ CD45RA+ human T cells were stimulated as described for 48 h and expression of (FIG. 3D) RORC, (FIG. 3E) RORA, (FIG. 3F) IL-17A, and (FIG. 3G) T-bet was analyzed by real-time PCR. Data are representative of two independent experiments with similar results.

(FIGS. 4A-4C) Human CD4+ CD45RO+ T cells were stimulated with plate-bound anti-CD3 and anti-CD28 antibodies with the addition of the indicated cytokines. Culture supernatants were analyzed for (FIG. 4A) IL-17, (FIG. 4B) IFNγ, and (FIG. 4C) IL-22 after 72 h by ELISA. Data represent the mean of duplicates ±SD. One representative experiment out of at least four independent experiments with similar results is shown. (FIG. 4D) Human CD4+ CD45RO+ T cells were stimulated as described. After 72 h incubation cells were restimulated with PMA/Ionomycin for 5 h and the percentages of IFN-γ- and IL-17-producing cells were measured by intracellular cytokine staining using flow cytometry. Data are representative of four independent experiments with similar results.

(FIGS. 5A-5C) Human CD4+ CD45RO+ CCR6+ TH17 cells were stimulated with plate-bound anti-CD3 and anti-CD28 antibodies with the addition of the indicated cytokines. Supernatants were analyzed for (FIG. 5A) IL-17, (FIG. 5B) IFNγ, and (FIG. 5C) IL-22 after 72 h by ELISA. Data represent the mean of duplicates ±SD. One representative experiment out of three experiments with similar results is shown.

(FIGS. 6A-6B) Human CD4+ CD45RO+ CCR6+ TH17 cells were stimulated with plate-bound anti-CD3 and anti-CD28 antibodies with the addition of TK1A. (FIG. 6A) Fold increase of IL-9 mRNA was measured by real-time PCR. (FIG. 6B) Supernatants were analyzed for IL-9 after 72 h by ELISA. (FIG. 6C) Human CD4+CD45RO+CCR6+TH17 cells were stimulated with place bound anti-CD3 and anti-CD28 antibodies in the presence of the indicated cytokines for 24, 48, or 72 h. Supernatants were analyzed for IL-9. Data represent the mean of duplicates ±SD. One representative experiment out of three experiments with similar results is shown.

FIGS. 25A-25B depict, in accordance with embodiments herein, sequences for probes and primers for the respective genetic loci. FIG. 25A depicts, in accordance with embodiments herein, sequences for probes and primers for the respective genetic loci. FIG. 25B depict, in accordance with embodiments herein, sequences for probes and primers for the respective genetic loci.

FIGS. 26A-26F depict, expression analysis by the inventors of TL1A-induced signaling pathways (including 76 genes up-regulated by TL1A and 90 genes down-regulated by TL1A, comprising the a signature of the TL1A signaling pathway. Together, the upregulation and downregulation patterns are part of an overall TL1A signaling profile. (FIG. 26A) depicts genes down regulated in response to TL1A. (FIG. 26B) depicts genes down regulated in response to TL1A. (FIG. 26C) depicts genes down regulated in response to TL1A. (FIG. 26D) depicts genes up regulated in response to TL1A. (FIG. 26E) depicts genes up regulated in response to TL1A. (FIG. 26F) depicts genes up regulated in response to TL1A.

DESCRIPTION OF THE INVENTION

Figure 1A:
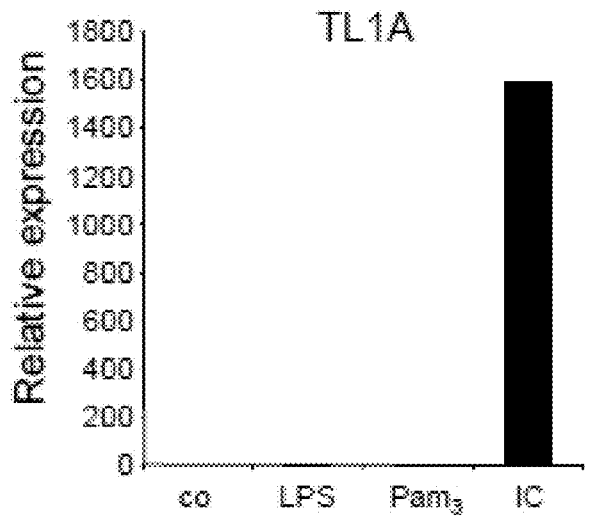
FIGS. 1A-1G depict, in accordance with embodiments herein, FcγR stimulation in monocytes induces concomitant expression of TL1A and TGF-β1. CD14+ monocytes were stimulated with Immune Complexes (IC), LPS, Pam3, IFN-γ, Flagellin, or anti-CD40 Ab for the indicated time points. Expression of various cytokines was analyzed by real-time PCR and normalized to β-Actin expression levels.

All references cited herein are incorporated by reference in their entirety as though fully set forth. Unless defined otherwise, technical and scientific terms used herein have the same meaning as commonly understood by one of ordinary skill in the art to which this invention belongs. Hornyak, et al., Introduction to Nanoscience and Nanotechnology, CRC Press (2008); Singleton et al., Dictionary of Microbiology and Molecular Biology 3rd ed., J. Wiley & Sons (New York, N.Y. 2001); March, Advanced Organic Chemistry Reactions, Mechanisms and Structure 7th ed., J. Wiley & Sons (New York, N.Y. 2013); and Sambrook and Russel, Molecular Cloning: A Laboratory Manual 4th ed., Cold Spring Harbor Laboratory Press (Cold Spring Harbor, N.Y. 2012), provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As disclosed herein, the inventors determined if TL1A enhances the differentiation and/or activation of TH17 cells in humans. TL1A is induced in Antigen-presenting cells in response to enteric bacteria and Fe gamma receptor signaling. Variation in TNFSF15, the TL1A gene, may contribute to Crohn's Disease and ulcerative colitis. Haplotypes composed of 5 TNFSF15 SNPs were observed to confer significant Crohn's Disease risk (haplotype A) and protection (haplotype B), using both case/control and family-based study designs. As further described herein, the inventors found that TL1A induces IL-22 and IL-17 from peripheral blood TH17 cells. Additionally, the inventors identified TL1A-induced IL-9 as a cytokine that induces IL-22 secretion from TH17 cells. Furthermore, the inventors demonstrate that blockage of IL-9 using neutralizing antibodies prevents TL1A-induced IL-22 secretion in TH17, suggesting a pathway for therapeutic intervention.

In one embodiment, the present invention provides a method of diagnosing a disease in a subject by obtaining a sample from the subject, subjecting the sample to an assay adapted to determine the presence or absence of TL1A expression and/or TL1A risk haplotype, and diagnosing the disease based on the presence of elevated TL1A expression and/or TL1A risk haplotype in the subject. In another embodiment, the subject is human. In another embodiment, the subject is Asian. In another embodiment, the subject has elevated Th17 signature cytokines. In another embodiment, the sample is taken from the peripheral blood and/or intestinal biopsy of the subject. In another embodiment, the subject is treated by administration of inhibitor of TL1A and/or administration of inhibitor of one or more Th17 signature cytokines. In another embodiment, the Th17 signature cytokines include IL-17, IL-22 and/or IL-9. In another embodiment, the disease is an inflammatory disease. In another embodiment, the disease is inflammatory bowel disease (IBD). In another embodiment, the disease is rheumatoid arthritis.

In one embodiment, the present invention provides a method of treating an inflammatory condition in a subject, comprising determining the presence of elevated TL1A expression, Th17 signature cytokines, and/or one or more TL1A genetic risk variants, and treating the inflammatory condition in the subject. In another embodiment, the subject is human. In another embodiment, the subject is Asian. In one embodiment, the inflammatory condition is inflammatory bowel disease. In another embodiment, the inflammatory condition is treated by administering a therapeutically effective dosage of inhibitor of TL1A and/or inhibitor of one or more Th17 signature cytokines. In another embodiment, the one or more Th17 signature cytokines include IL-17, IL-22 and/or IL-9. In another embodiment, the treatment is administered in conjunction with an anti-inflammatory therapeutic. In another embodiment, the treatment is administered by direct injection to the subject.

In one embodiment, the present invention provides a composition comprising a therapeutically effective dosage of inhibitor of TL1A and/or inhibitor of Th17 signature cytokines, and an acceptable carrier. In another embodiment, the inhibitor of TL1A is a TL1A antibody.

In one embodiment, the present invention provides a method of treating a disease in a subject by providing a composition comprising a therapeutically effective dosage of inhibitor of TL1A and/or inhibitor of Th17 signature cytokines, and administering the composition to the subject. In another embodiment, the disease is Inflammatory Bowel Disease (IBD). In another embodiment, the disease is arthritis.

As readily apparent to one of skill in the art, a variety of methods can be used to determine the presence or absence of a risk variant allele or haplotype, such as a TL1A (TNFSF15) genetic risk variant, and/or TL1A (TNFSF15) genetic risk haplotype. As an example, enzymatic amplification of nucleic acid from an individual may be used to obtain nucleic acid for subsequent analysis. The presence or absence of a variant allele or haplotype may also be determined directly from the individual's nucleic acid without enzymatic amplification.

As further disclosed herein, the inventors demonstrate that FcγR signaling leads to concomitant induction of TL1A, IL-6, TGF-β, and IL-23, a cytokine milieu that fosters the development of TH17 cells. TL1A, in combination with TGF-β and IL-6, promoted differentiation of human TH17 cells from naive CD4+ T cells. Additionally, TL1A in combination with TGF-β and IL-6 enhanced IL-17 production from CD4+ CD45RO+ memory T cells and induced IL-17/IFN-γ producing TH17 cells. In contrast, TL1A alone induced high levels of IL-22 in naïve and memory CD4+ T cells. TL1A also enhanced IL-17 and IL-22 production by committed CD45RO+CCR6+ TH17 cells suggesting that TL1A is able to induce TH17 differentiation and enhances IL-17 secretion from committed TH17 cells. Thus, in one embodiment, TL1A provides a target for therapeutic intervention in chronic inflammatory diseases.

In one embodiment, the present invention provides a method of treating a disease, comprising obtaining a sample from a subject, assaying the sample to diagnose a disease based on the presence of TH17 cell differentiation, treating the subject by administering a therapeutically effective dosage of a composition comprising one or more inhibitors of TL1A. In another embodiment, the TH17 cell differentiation is from human naïve CD4+ T cells. The disease may also be in inflammatory related disease. In another embodiment, the disease is psoriasis, arthritis, experimental autoimmune encephalomyelitis, or colitis. In another embodiment, diagnosing the disease comprises determining the presence of a TL1A signaling profile. In another embodiment, the TL1A signaling profile comprises the presence of a downregulation of one or more genes listed in FIGS. 26A-26C herein. In another embodiment, the the TL1A signaling profile comprises the presence of an upregulation of one or more genes listed in FIGS. 26D-26F herein. In another embodiment, the one or more inhibitors of TL1A is an inhibitor of the DR3 receptor. In another embodiment, the disease is intestinal inflammation. In another embodiment, the present invention provides a method of treating an inflammatory disease in a subject, comprising determining the presence of a TL1A signaling profile in a subject, and treating the inflammatory disease by inhibiting TH17 differentiation from CD4+ T cells. In another embodiment, the TL1A signaling profile comprises the presence of a downregulation of one or more genes listed in FIGS. 26A-26C herein. In another embodiment, the TL1A signaling profile comprises the presence of an upregulation of one or more genes listed in FIGS. 26D-26F herein. In another embodiment, inhibiting TH17 differentiation comprises administering one or more inhibitors of TL1A. In another embodiment, inhibiting TH17 differentiation further comprises inhibiting IL17 secretion from TH17 cells.

Analysis of the nucleic acid from an individual, whether amplified or not, may be performed using any of various techniques. Useful techniques include, without limitation, polymerase chain reaction based analysis, sequence analysis and electrophoretic analysis. As used herein, the term "nucleic acid" means a polynucleotide such as a single or double-stranded DNA or RNA molecule including, for example, genomic DNA, cDNA and mRNA. The term nucleic acid encompasses nucleic acid molecules of both natural and synthetic origin as well as molecules of linear, circular or branched configuration representing either the sense or antisense strand, or both, of a native nucleic acid molecule.

The presence or absence of a variant allele or haplotype may involve amplification of an individual's nucleic acid by the polymerase chain reaction. Use of the polymerase chain reaction for the amplification of nucleic acids is well known in the art (see, for example, Mullis et al. (Eds.), The Polymerase Chain Reaction, Birkhauser, Boston, (1994)).

A TaqmanB allelic discrimination assay available from Applied Biosystems may be useful for determining the presence or absence of a variant allele. In a TaqmanB allelic discrimination assay, a specific, fluorescent, dye-labeled probe for each allele is constructed. The probes contain different fluorescent reporter dyes such as FAM and VICTM to differentiate the amplification of each allele. In addition, each probe has a quencher dye at one end which quenches fluorescence by fluorescence resonant energy transfer (FRET). During PCR, each probe anneals specifically to complementary sequences in the nucleic acid from the individual. The 5' nuclease activity of Taq polymerase is used to cleave only probe that hybridize to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Improved specificity in allelic discrimination assays can be achieved by conjugating a DNA minor grove binder (MGB) group to a DNA probe as described, for example, in Kutyavin et al., "3'-minor groove binder-DNA probes increase sequence specificity at PCR extension temperature," Nucleic Acids Research 28:655-661 (2000)). Minor grove binders include, but are not limited to, compounds such as dihydrocyclopyrroloindole tripeptide (DPI,). Sequence analysis also may also be useful for determining the presence or absence of a variant allele or haplotype.

Restriction fragment length polymorphism (RFLP) analysis may also be useful for determining the presence or absence of a particular allele (Jarcho et al. in Dracopoli et al., Current Protocols in Human Genetics pages 2.7.1-2.7.5, John Wiley & Sons, New York; Innis et al., (Ed.), PCR Protocols, San Diego: Academic Press, Inc. (1990)). As used herein, restriction fragment length polymorphism analysis is any method for distinguishing genetic polymorphisms using a restriction enzyme, which is an endonuclease that catalyzes the degradation of nucleic acid and recognizes a specific base sequence, generally a palindrome or inverted repeat. One skilled in the art understands that the use of RFLP analysis depends upon an enzyme that can differentiate two alleles at a polymorphic site.

Allele-specific oligonucleotide hybridization may also be used to detect a disease-predisposing allele. Allele-specific oligonucleotide hybridization is based on the use of a labeled oligonucleotide probe having a sequence perfectly complementary, for example, to the sequence encompassing a disease-predisposing allele. Under appropriate conditions, the allele-specific probe hybridizes to a nucleic acid containing the disease-predisposing allele but does not hybridize to the one or more other alleles, which have one or more nucleotide mismatches as compared to the probe. If desired, a second allele-specific oligonucleotide probe that matches an alternate allele also can be used. Similarly, the technique of allele-specific oligonucleotide amplification can be used to selectively amplify, for example, a disease-predisposing allele by using an allele-specific oligonucleotide primer that is perfectly complementary to the nucleotide sequence of the disease-predisposing allele but which has one or more mismatches as compared to other alleles (Mullis et al., supra, (1994)). One skilled in the art understands that the one or more nucleotide mismatches that distinguish between the disease-predisposing allele and one or more other alleles are preferably located in the center of an allele-specific oligonucleotide primer to be used in allele-specific oligonucleotide hybridization. In contrast, an allele-specific oligonucleotide primer to be used in PCR amplification preferably contains the one or more nucleotide mismatches that distinguish between the disease-associated and other alleles at the 3' end of the primer.

A heteroduplex mobility assay (HMA) is another well known assay that may be used to detect a SNP or a haplotype. HMA is useful for detecting the presence of a polymorphic sequence since a DNA duplex carrying a mismatch has reduced mobility in a polyacrylamide gel compared to the mobility of a perfectly base-paired duplex (Delwart et al., Science 262:1257-1261 (1993); White et al., Genomics 12:301-306 (1992)).

The technique of single strand conformational, polymorphism (SSCP) also may be used to detect the presence or absence of a SNP and/or a haplotype (see Hayashi, K., Methods Applic. 1:34-38 (1991)). This technique can be used to detect mutations based on differences in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) also may be used to detect a SNP and/or a haplotype. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990). Other molecular methods useful for determining the presence or absence of a SNP and/or a haplotype are known in the art and useful in the methods of the invention. Other well-known approaches for determining the presence or absence of a SNP and/or a haplotype include automated sequencing and RNAase mismatch techniques (Winter et al., Proc. Natl. Acad. Sci. 82:7575-7579 (1985)). Furthermore, one skilled in the art understands that, where the presence or absence of multiple alleles or haplotype(s) is to be determined, individual alleles can be detected by any combination of molecular methods. See, in general, Birren et al. (Eds.) Genome Analysis: A Laboratory Manual Volume 1 (Analyzing DNA) New York, Cold Spring Harbor Laboratory Press (1997). In addition, one skilled in the art understands that multiple alleles can be detected in individual reactions or in a single reaction (a "multiplex" assay).

There are also many techniques readily available in the field for detecting the presence or absence of polypeptides or other biomarkers, such as determining the presence or absence of TL1A and/or one or more Th17 signature cytokines. For example, some of the detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Similarly, there are any number of techniques that may be employed to isolate and/or fractionate biomarkers. For example, a biomarker may be captured using biospecific capture reagents, such as antibodies, aptamers or antibodies that recognize the biomarker and modified forms of it. This method could also result in the capture of protein interactors that are bound to the proteins or that are otherwise recognized by antibodies and that, themselves, can be biomarkers. The biospecific capture reagents may also be bound to a solid phase. Then, the captured proteins can be detected by SELDI mass spectrometry or by eluting the proteins from the capture reagent and detecting the eluted proteins by traditional MALDI or by SELDI. One example of SELDI is called "affinity capture mass spectrometry," or "Surface-Enhanced Affinity Capture" or "SEAC," which involves the use of probes that have a material on the probe surface that captures analytes through a non-covalent affinity interaction (adsorption) between the material and the analyte. Some examples of mass spectrometers are time-of-flight, magnetic sector, quadrupole filter, ion trap, ion cyclotron resonance, electrostatic sector analyzer and hybrids of these.

Alternatively, for example, the presence of biomarkers such as polypeptides maybe detected using traditional immunoassay techniques. Immunoassay requires biospecific capture reagents, such as antibodies, to capture the analytes. The assay may also be designed to specifically distinguish protein and modified forms of protein, which can be done by employing a sandwich assay in which one antibody captures more than one form and second, distinctly labeled antibodies, specifically bind, and provide distinct detection of, the various forms. Antibodies can be produced by immunizing animals with the biomolecules. Traditional immunoassays may also include sandwich immunoassays including ELISA or fluorescence-based immunoassays, as well as other enzyme immunoassays.

Prior to detection, biomarkers may also be fractionated to isolate them from other components in a solution or of blood that may interfere with detection. Fractionation may include platelet isolation from other blood components, sub-cellular fractionation of platelet components and/or fractionation of the desired biomarkers from other biomolecules found in platelets using techniques such as chromatography, affinity purification, 1D and 2D mapping, and other methodologies for purification known to those of skill in the art. In one embodiment, a sample is analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there.

"Anti-TL1A therapy", as used herein refers to therapeutic agents and methods that suppress TL1A gene expression, DR3 gene expression, or block the signaling of TL1A and DR3 (the receptor for TL1A) proteins. As used herein, the term "TL1A signaling inhibitor" (also interchangeably called as TL1A blocker or inhibitor, anti-TL1A reagent, agent, drug or therapeutic,) refers to any reagent that suppress responses to TL1A and/or inhibits the TL1A signaling, including inhibition of any molecular signaling step from the TL1A ligand through its receptor to various downstream target molecules. A TL1A signaling inhibitor can be a small molecule; a nucleic acid such as siRNA, shRNA, and miRNA; a nucleic acid analogue such as PNA, pc-PNA, and LNA; an aptamer; a ribosome; a peptide; a protein; an avimer; an antibody, or variants and fragments thereof. Examples of the TL1A signaling inhibitor include but are not limited to an anti-TL1A antibody blocking TL1A-DR3 signaling, an anti-DR3 antibody blocking TL1A-DR3 signaling, a soluble decoy DR3 polypeptide (e. g., a soluble DR3-Fc fusion protein), or a nucleic acid antagonist of TL1A or DR3, such as an aptamer or antisense molecule targeting TL1A or DR3, or a combination thereof. In certain embodiments, the TL1A signaling inhibitor comprises an anti-TL1A antibody or a fragment thereof, an anti-DR3 antibody or a fragment thereof, a soluble decoy DR3 polypeptide, a nucleic acid antagonist of TL1A, or a nucleic acid antagonist of DR3, or a combination thereof.

Typical dosages of an effective amount of treatment or therapy can be in the ranges recommended by the manufacturer where known therapeutic molecules or compounds are used, and also as indicated to the skilled artisan by the in vitro responses in cells or in vivo responses in animal models. Such dosages typically can be reduced by up to about an order of magnitude in concentration or amount without losing relevant biological activity. The actual dosage can depend upon the judgment of the physician, the condition of the patient, and the effectiveness of the therapeutic method based, for example, on the in vitro responsiveness of relevant cultured cells or histocultured tissue sample, or the responses observed in the appropriate animal models. In various embodiments, the therapy may be administered once a day (SID/QD), twice a day (BID), three times a day (TID), four times a day (QID), or more, so as to administer an effective amount of the therapy to the individual, where the effective amount is any one or more of the doses described herein.

In various embodiments, composition for treatment is administered at about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg, or a combination thereof. In various embodiments, the treatment or therapy is administered once, twice, three or more times. In some embodiments, the therapy is administered about 1-3 times per day, 1-7 times per week, or 1-9 times per month. Still in some embodiments, the treatment, or therapy is administered for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. Here, "mg/kg" refers to mg per kg body weight of the individual. In certain embodiments, the therapy is administered to a human.

In accordance with the invention, the therapy may be administered using the appropriate modes of administration, for instance, the modes of administration recommended by the manufacturer. In accordance with the invention, various routes may be utilized to administer the IBD therapy of the claimed methods, including but not limited to aerosol, nasal, oral, transmucosal, transdermal, parenteral, enteral, topical, local, implantable pump, continuous infusion, capsules and/or injections. In various embodiments, the IBD therapy is administered topically, intravascularly, intravenously, intraarterially, intramuscularly, subcutaneously, intraperitoneally, intranasally, or orally.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Conclusions

TL1A enhances differentiation of Th17 cells from naïve CD4+ T cells.
TL1A increases % of IL-17 and IL-17/IFNg double positive CD45RO+ T cells.
TL1A induces the expression of RORA and T-bet but has no effect on the expression of RORC.
TL1A induces IL-22 secretion in Th17 cells (CD45RO+ CCR6+ T cells).
TL1A induces IL-9 secretion in Th17 cells.

Example 2

Diagnostics and Treatments

The inventors found that TL1A plays an important role in the induction of Th17 signature cytokines including IL-17, IL-22, and IL-9. Patients carrying a risk haplotype for the TL1A gene have elevated expression of TL1A. In one embodiment, the present invention provides a diagnostic where these patients will also have elevated TL1A-induced TH17 signature cytokines that could be measured as a diagnostic test. That diagnostic test would help to identify specific patient population that would benefit the most from inhibition of either TL1A or the TH17 signature cytokines. In another embodiment, the present invention provides a companion diagnostic test for patients with IBD or rheumatoid arthritis with ongoing inflammation to determine the degree of inflammation and/or identify potential treatment options. In another embodiment, patients with risk polymorphisms for TL1A would be identified as a subgroup that would benefit from treatment. Further, TL1A single nucleotide polymorphisms may be strongly associated with the development and severity of IBD particularly in the Asian population.

Example 3

Overall

TL1A, a member of the TNF superfamily, mediates a strong co-stimulation of TH1 cells by enhancing IFN-γ production by peripheral CD4+ and mucosal CCR9+ T cells. TL1A plays an important role in the development of chronic colitis, experimental autoimmune encephalomyelitis, and allergic lung inflammation by modulating TH1, TH17, and TH2 responses suggesting an important role in chronic inflammatory processes. We have shown that TL1A is induced in antigen-presenting cells in response to FcγR signaling. Here, we demonstrate that FcγR signaling leads to concomitant induction of TL1A, IL-6, TGF-β, and IL-23, a cytokine milieu that fosters the development of TH17 cells. TL1A, in combination with TGF-β and IL-6, promoted differentiation of human TH17 cells from naive CD4+ T cells. Additionally, TL1A in combination with TGF-β and IL-6 enhanced IL-17 production from CD4+ CD45RO+ memory T cells and induced IL-17/IFN-γ producing TH17 cells. In contrast, TL1A alone induced high levels of IL-22 in naïve and memory CD4+ T cells. TL1A also enhanced IL-17 and IL-22 production by committed CD45RO+ CCR6+ TH17 cells suggesting that TL1A is able to induce TH17 differentiation and enhances IL-17 secretion from committed TH17 cells. Thus, in one embodiment, TL1A provides a target for therapeutic intervention in chronic inflammatory diseases.

Example 4

Methods and Materials

Isolation of CD14+ Monocytes from Blood:

Blood was obtained from healthy volunteers after informed consent in accordance with procedures established by the Cedars-Sinai Institutional Review Board. Plate-bound, cross-linked human IgG (IC) was prepared. Monocytes were incubated with IC for the indicated time-points.

Isolation of CD4+ T Cells from PBMC and Cell Sorting:

CD4+ T cells were isolated from PBMC by negative selection using the human T lymphocyte Enrichment Set (BD Bioscience). CD4+ T cells were stained with PE-conjugated anti-CD45RO Ab and FITC-conjugated anti-CD45RA Ab (Caltag Laboratories). CD45RA+ or CD45RO+ cells were collected using the MoFlo™ High Performance Cell Sorter (Dako Cytomation). In some experiments the CD4+ T cells were stained for CD45RO (FITC-conjugated) and CCR6 (PE-conjugated) and CD45RO+/CCR6+ cells were collected.

T Cell Stimulation:

T cells were stimulated with immobilized anti-CD3 (5 ug/ml, BD Bioscience) and anti-CD28 (2 ug/ml, Bristol-Myers Squibb) in the presence of TGF-β1 (3 ng/ml, Pepro-Tech), IL-6 (50 ng/ml PeproTech), IL-23 (20 ng/ml, R & D Systems), TL1A (100 ng/ml, Fitzgerald Industries International, Acton, MA), and neutralizing antibodies to IL-4 (2 ug/ml) and IFN-γ (3 ug/ml, Biolegend) for three days or as indicated. In selected experiments neutralizing antibodies to IL-9, IL-9 receptor (BioLegend), or isotype controls were added at the time of stimulation.

Real-Time PCR Analyses

TL1A, TGFβ, IL-10, IL-6, IL-23p19, IL-12p40, RORA, IL-17A (all Integrated DNA Technologies), and RORC (Applied Biosystems) transcripts were amplified by quantitative real-time RT-PCR. Primer/probe sequences described in FIG. 25A-25B herein and as SEQ. ID NOS: 1-30.

ELISA: TL1A was quantified by ELISA. Human IL-17A, IFN-γ, TGF-β, IL-6, IL-1β, IL-9 (all eBioscience), IL-22 (R&D Systems) were quantified using ELISA kits.

Flow Cytometry:

Cultured cells were stimulated with 50 nM of phorbol-12,13-dibutyrate and 1 ug/ml ionomycin for 2 h followed by Brefeldin A (Sigma-Aldrich, 10 ng/ml) stimulation for 4 h at 37 degrees C. Cells were harvested and stained for intracellular IL-17 (Alexa Fluor 647-IL-17), IFN-γ (PE-Cy 7-IFN-γ), IL-22 (PE-IL-22), IL-9 (eFluor 660-IL-9) or isotype controls utilizing the Fixation and Permeabilization kit (eBioscience). Cells were acquired on a CyAn™ ADP flow cytometer (Dako) and analyzed using FlowJo software (TreeStar Inc., Ashland, Oreg.).

Gene Expression Analysis:

RNA was isolated from stimulated T cells at the indicated time-points. cRNA amplification and biotin labeling were performed with 500 ng total RNA using Illumina TotalPrep RNA Amplification Kit (Ambion). cRNA yield was determined using a NanoDrop spectrophotometer (NanoDrop Technologies, Wilmington, Del.), and 1.5 mg biotin-labeled cRNA was hybridized to HumanWG-6 v3 Expression Bead-chips (Illumina). Data visualization and quality control were carried out with the Gene Expression module of GenomeStudio software (Illumina). Data were transformed by a variance stabilizing method and normalized by quantile normalization (implemented in the lumi package of R v2.11.1). Data were carried forward into analysis if the detection signal for all samples within at least one of the four groups (control-AA, CD-AA, control-GG, CD-GG) was positive (p value for detection<0.01). Thus 14 541 probes remained for analysis. The association of RNA expression was analyzed using a two-way analysis of variance (ANOVA) for this two-by-two factorial design across the four groups, as implemented in MultiExperiment Viewer (TM4 microarray software suite).

Statistics:

Statistical significance was determined by Student's t test. A value of p<0.05 was considered to be statistically significant.

Example 5

Results

Figure 1B:
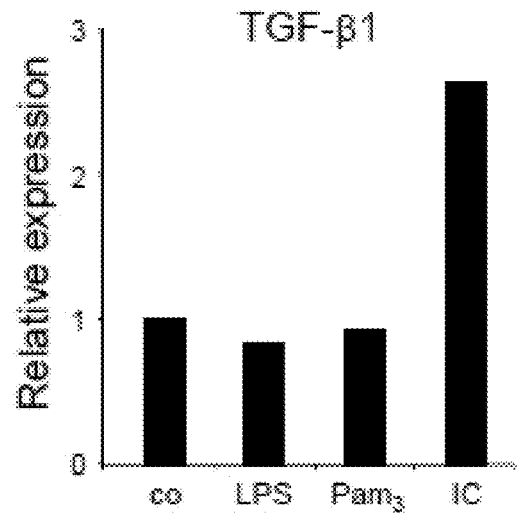
Figure 1C:
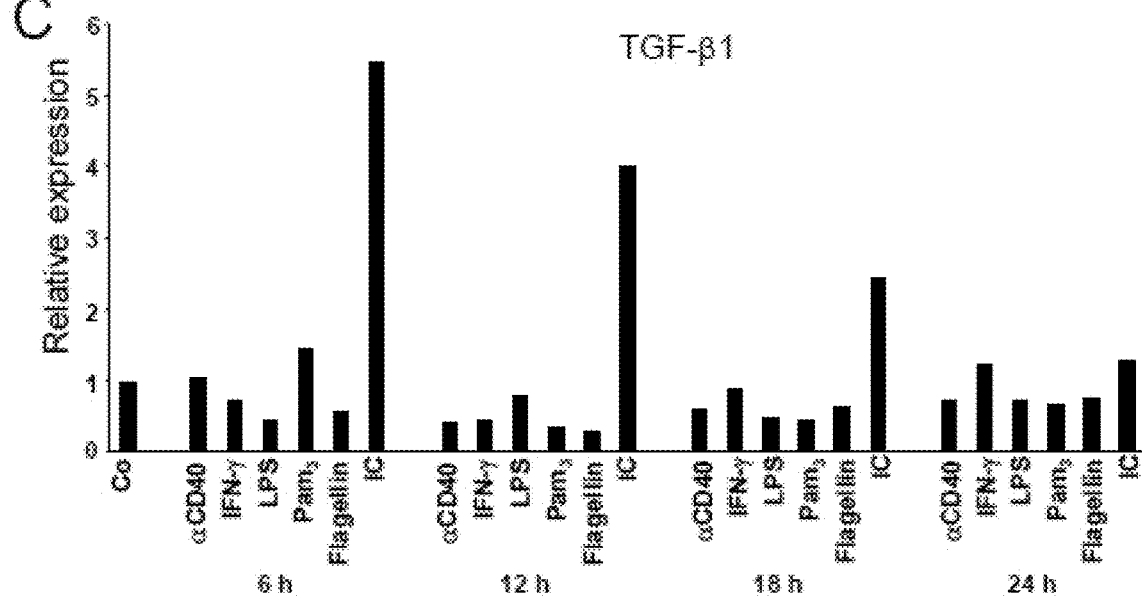
Figure 1D:
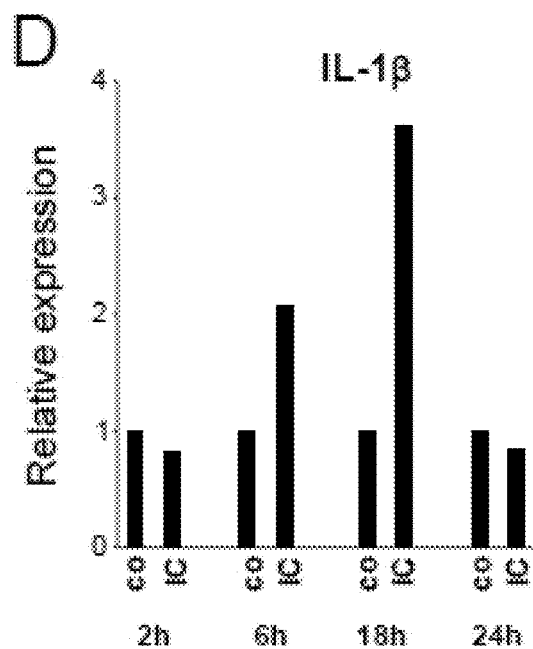
Figure 1E:
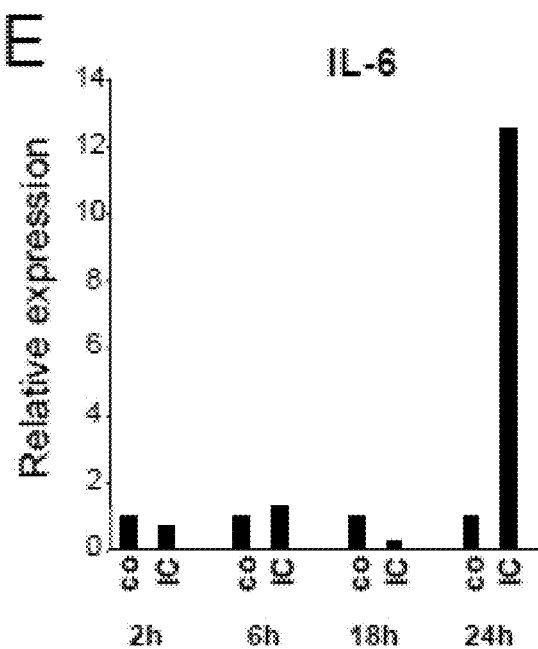
Figure 1F:
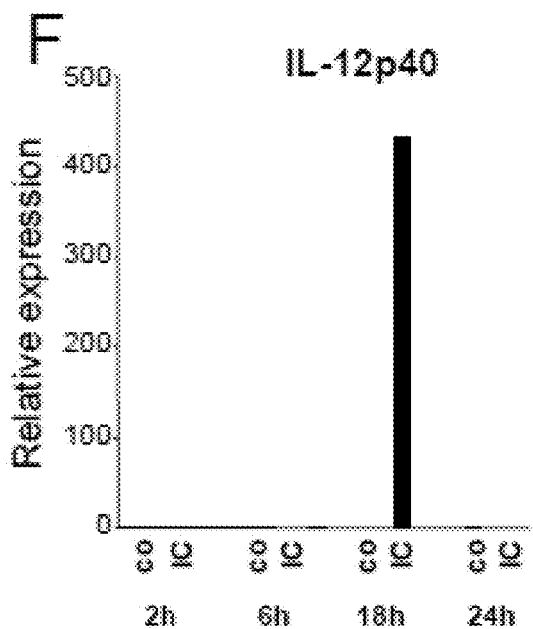
Figure 1G:
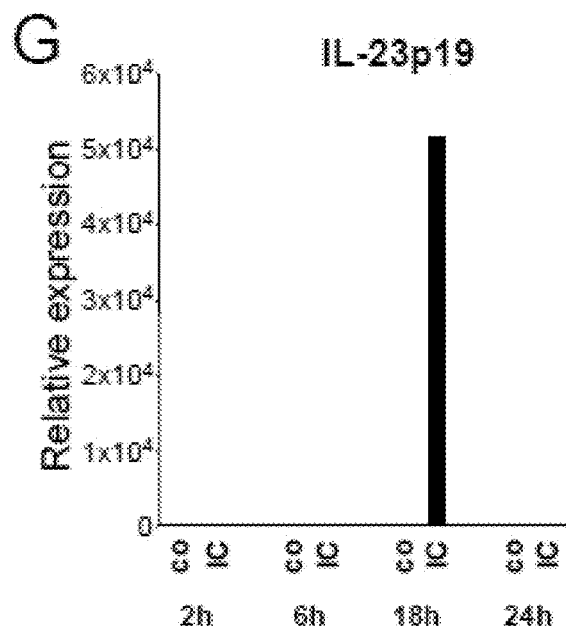
Figures 2A, 2B:
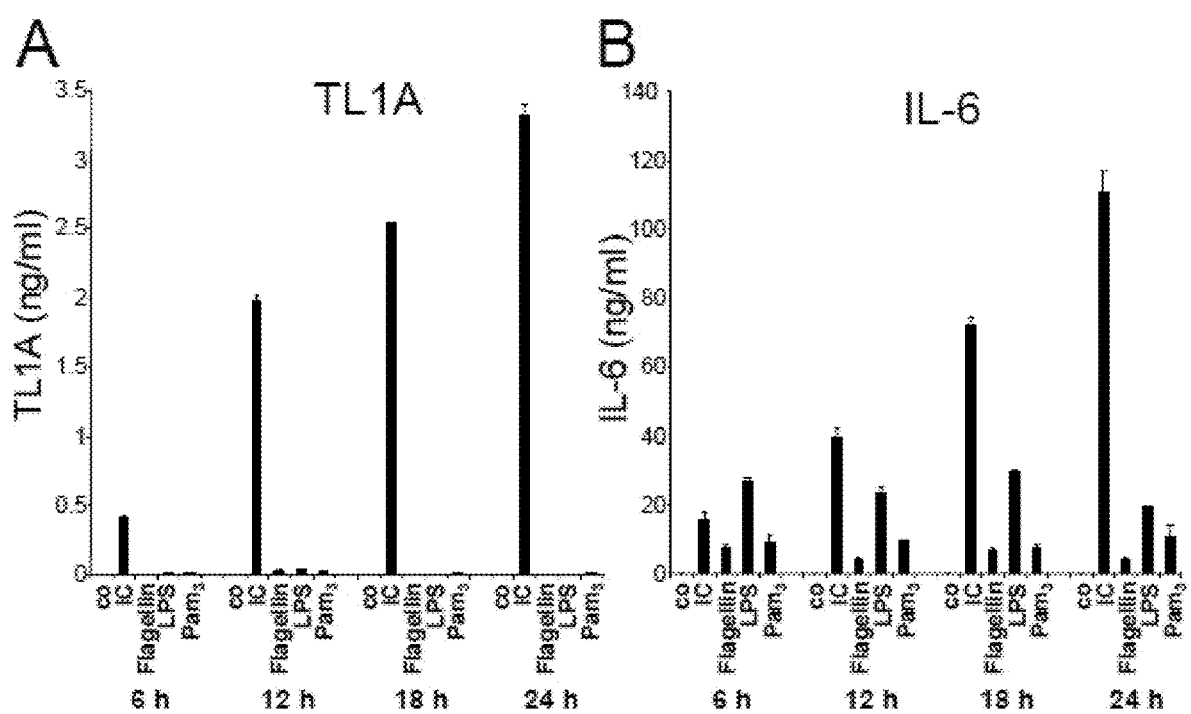

Cytokine Expression Profile of Fcγ R Stimulated Human Monocytes:

The inventors demonstrated that TL1A is a strong costimulator of TH1 responses. Furthermore, Fcγ Receptor signaling induces the expression of TL1A mRNA and subsequent secretion of TL1A protein in monocytes and dendritic cells (DC). However, to address whether TL1A also has an effect on the differentiation of the pro-inflammatory TH17 subset, the inventors first evaluated the expression pattern of cytokines that have been implicated in the differentiation of human TH17 cells in monocytes stimulated with immune complexes (IC), a strong inducer of TL1A in these cells. IC is a strong inducer of TL1A mRNA while TLR ligands (LPS as TLR4 ligand, Pam3 as TLR2 ligand) do not induce TL1A (FIG. 1A). Interestingly, only IC induced significant increases in TGF-β1 mRNA in monocytes while TLR ligands did not induce TGF-β1 (FIG. 1B). To evaluate if the lack of TGF-β1 induction by ligands other than IC is related to different kinetics in the induction of TGF-β1 the inventors performed extensive time-course experiments in monocytes using the TLR ligands LPS, Pam3, Flagellin, as well as IFN-γ, and anti-CD40 (FIG. 1C). TGF-β1 mRNA was only induced in IC stimulated monocytes while TLR ligands, IFN-γ, or anti-CD40 failed to induce TGF-β1 mRNA (FIG. 1C). Similar results were obtained from human monocyte-derived DC. The inventors evaluated the expression of cytokines that have been linked with the differentiation of human TH17 cells. IC induced IL-1β, IL-6, IL-12p40, and IL-23p19 mRNA (FIGS. 1D-G). These real-time PCR data were confirmed by ELISAs. IC stimulation of monocytes resulted in significant secretion of IL-6, IL-1β, and TGF-β (FIGS. 2B-2D). Interestingly, IC was the strongest inducer of IL-6 and IL-1β compared to several TLR ligands. Taken together, IC stimulation results in the concomitant secretion of TL1A and cytokines that have been implicated in the differentiation of TH17 cells (IL-6, IL-1β, IL-23, TGF-β).

Figure 3A:
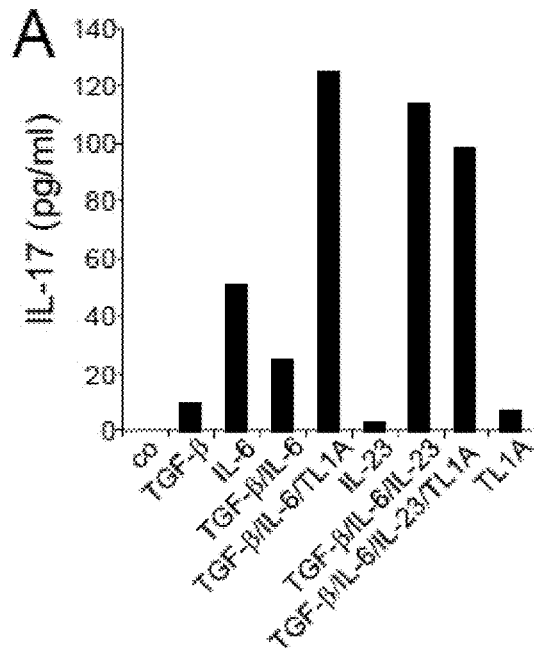
FIGS. 3A-3G depict, in accordance with embodiments herein, TL1A enhances TH17 differentiation of naive CD4+ T cells.
Figure 3B:
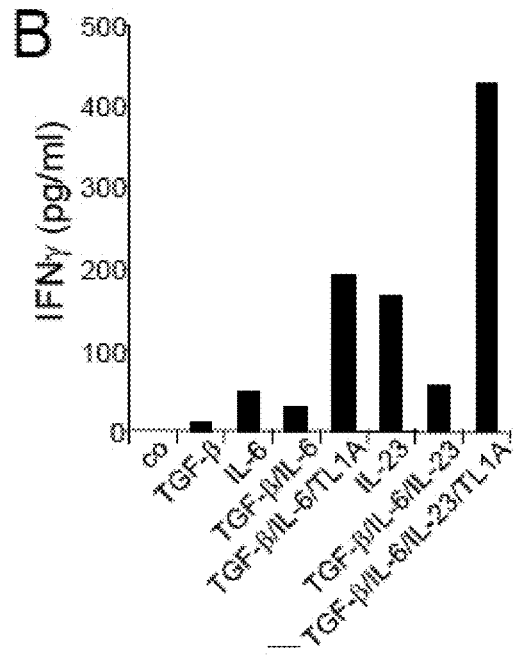
Figure 3C:
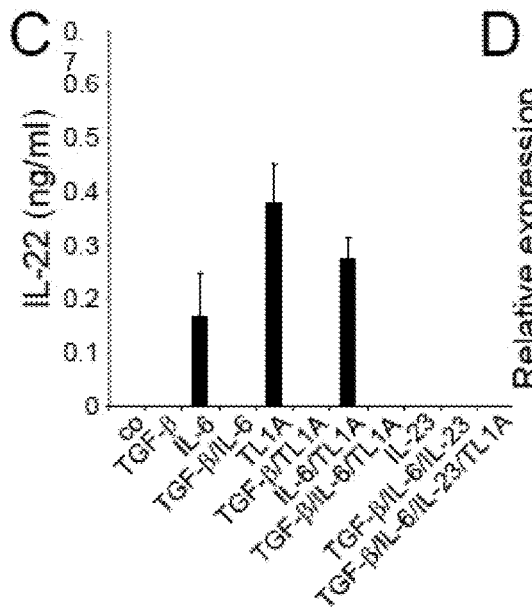

TL1A Enhances TH17 Differentiation of CD45RA+ Naive T Cells:

To establish a role of TL1A in the differentiation of human TH17 cells from naive CD45RA+ T cells, the inventors used high-speed flow cytometry for sorting CD45RA+ naive T cells from enriched CD4+ T cells isolated from PBMCs from healthy volunteers. The highly enriched naive CD4+ CD45RA+ T cells were first differentiated with anti-CD3/CD28 in the presence of TGF-β+IL-6 in the presence or absence of TL1A. In comparison to cells treated with TGF-□+IL-6, cells treated with TGF-β+IL-6+TL1A secreted significantly more IL-17 (FIG. 3A). Interestingly, addition of IL-23 does not further enhance the secretion of IL-17. TL1A has been shown to strongly enhance IFN-γ production of CD4+ T cells (4). Next, the inventors analyzed the IFN-γ production of naive CD45RA+ T cells that have been stimulated under TH17 polarizing conditions. TL1A enhances the production of IFN-γ from cells stimulated with TGF-β+IL-6 (FIG. 3B). In contrast to the IL-17 secretion, TL1A and IL-23 have additive effects on the IFN-γ secretion when added to TGF-β+IL-6 (FIG. 3B). Interestingly, TL1A stimulation alone leads to the induction of IL-22 in naive CD45RA+ T cells (FIG. 3C).

Figure 3D:
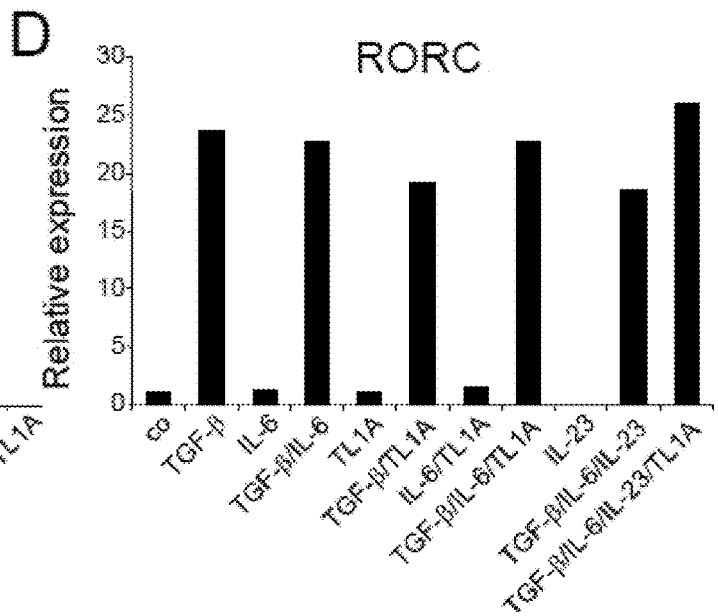
Figure 3E:
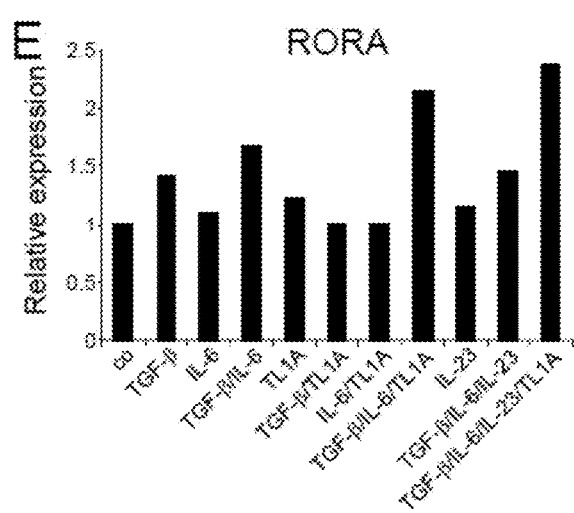
Figure 3F:
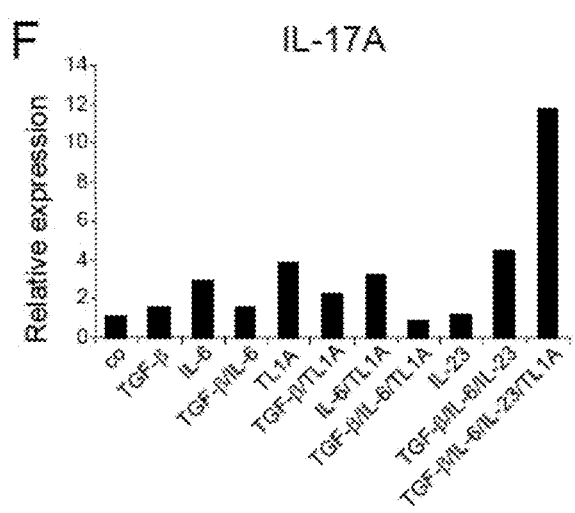
Figure 3G:
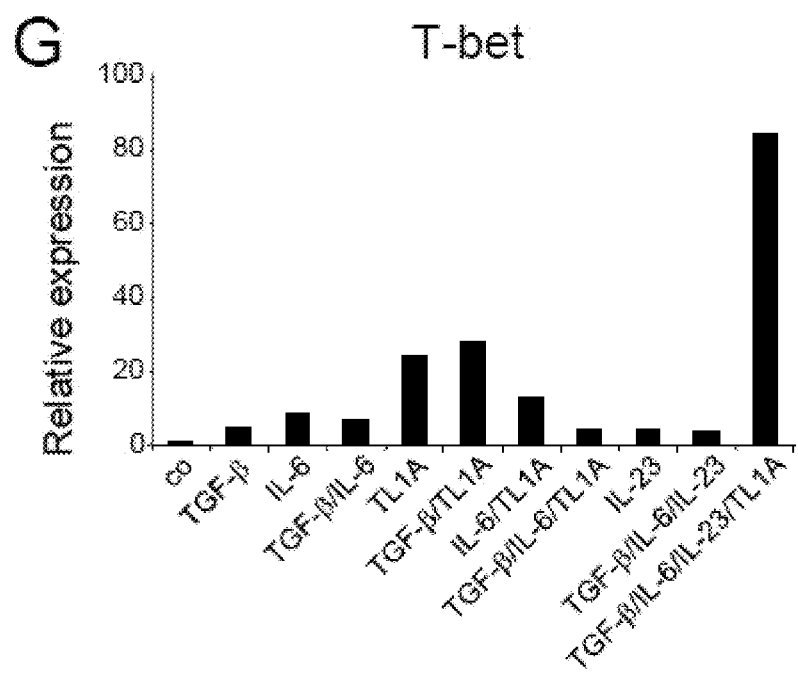

TL1A Enhances RORA and T-bet Expression During Early TH17 Polarization:

To understand the molecular mechanisms by which TL1A enhances TH17 polarization, the inventors stimulated naive human CD4+ CD45RA+ T cells under TH17 polarizing conditions in the absence or presence of TL1A and analyzed the expression of RORA and RORC mRNA (FIGS. 3D, E). Consistent with previous findings TGF-β alone is sufficient to induce RORC mRNA and neither the addition of IL-6 nor TL1A enhances RORC expression (FIG. 3D). In contrast, TL1A enhances the expression of the transcription factor RORA in combination with TGF-β+IL-6+IL-23 (FIG. 3E). It has been previously reported that TH17 differentiation is regulated by both transcription factors, RORA and RORC to achieve maximal expression/differentiation of IL-17/TH17 cells. Enhancement of RORA expression was sufficient to lead to enhanced IL-17A mRNA expression by TL1A (FIG. 3F). Interestingly, stimulation with TL1A in combination with TGF-β+IL-6+IL-23 also led to a maximal induction of T-bet mRNA (FIG. 3G) confirming data of maximal induction of IFN-γ in TH17 cells polarized in the presence of TL1A.

Figure 4A:
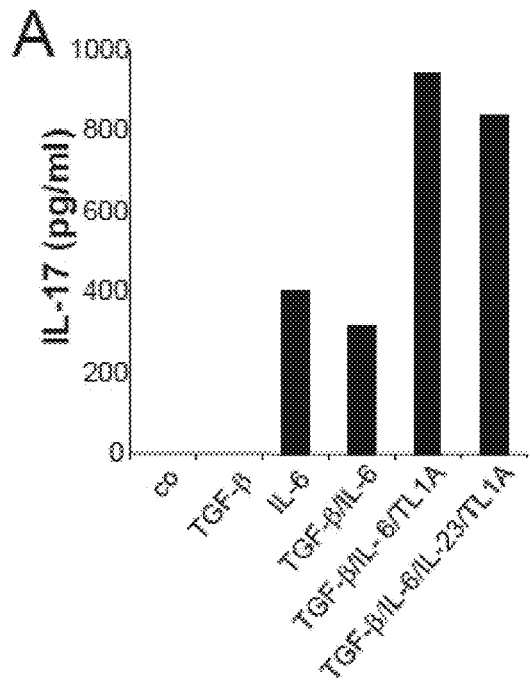
FIGS. 4A-4D depict, in accordance with embodiments herein, TL1A enhances IL-17, IFNγ, and IL-22 secretion from memory CD4+ CD45RO+ T cells, and increases the number of IFN-γ- and IL-17-producing cells.
Figure 4B:
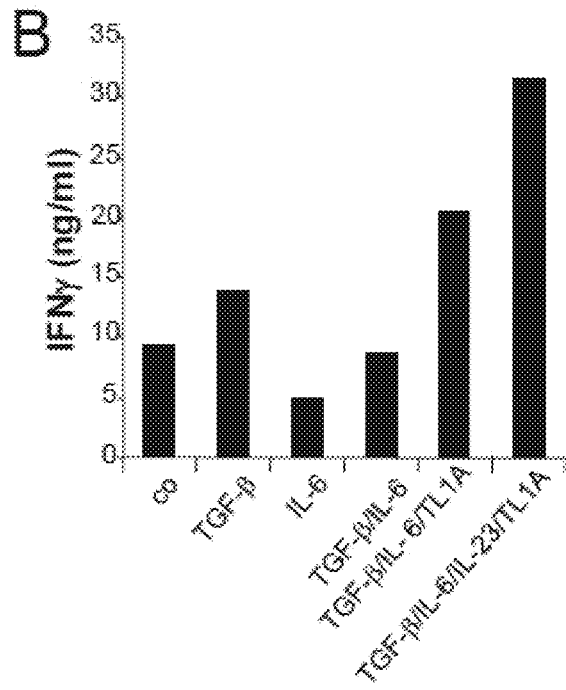
Figure 4C:
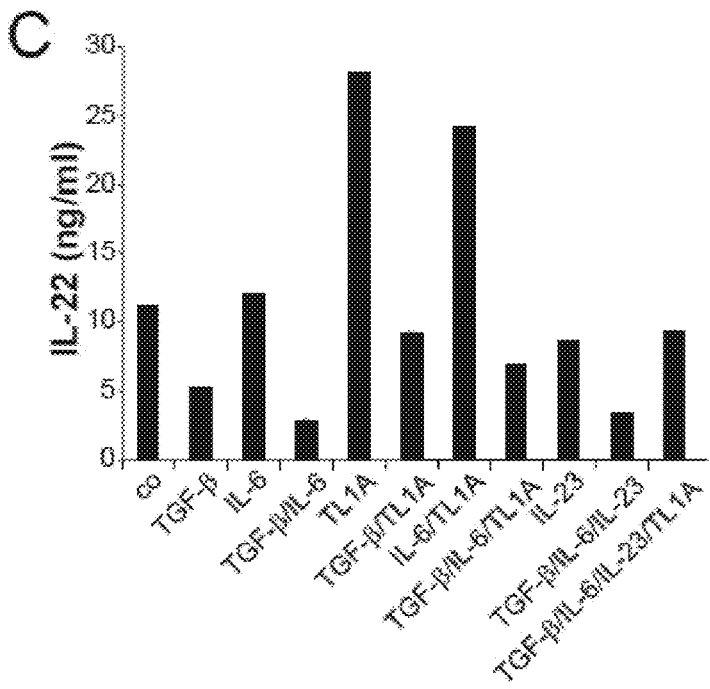
Figure 4D:
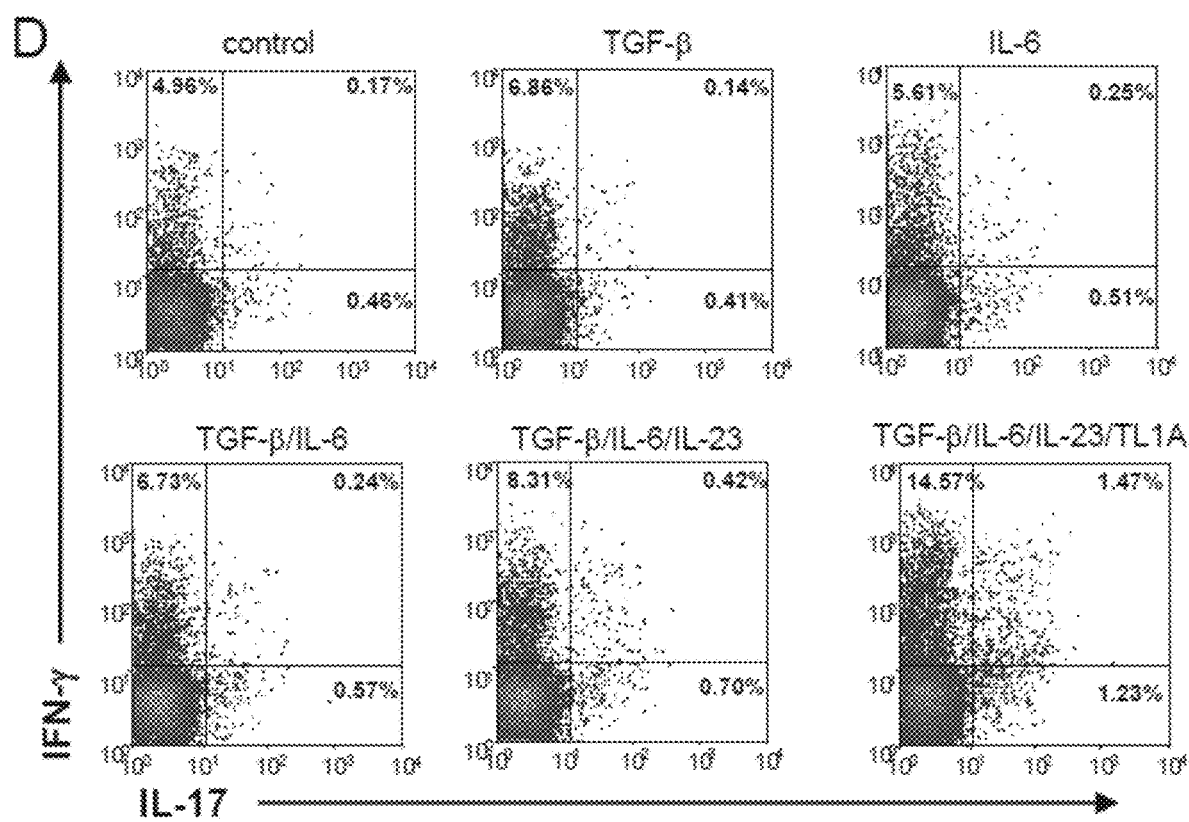

TL1A Enhances IL-17 Production by CD45RO+ Memory T Cells:

To further delineate the role of TL1A on TH17 development, the inventors analyzed if TL1A also has an effect on the IL-17 production by CD4+ CD45RO+ memory T cells. Interestingly, similar to findings in naive T cells TL1A enhances the production of IL-17 in combination with TGF-β+IL-6 (FIG. 4A). Interestingly, addition of IL-23 does not further enhance the secretion of IL-17 from CD4+ CD45RO+ memory T cells. In contrast, IL-23 and TL1A have additive effects on the IFN-γ secretion when added to TGF-β+ IL-6 (FIG. 4B). When analyzed the secretion of IL-22, it was observed that TL1A alone leads to maximal secretion of IL-22 in CD4+ CD45RO+ memory T cells (FIG. 4C). In contrast, TGF-β inhibits IL-22 secretion by TH17 cells and TL1A was not able to overcome the suppression by TGF-β. Furthermore, intracellular cytokine staining showed that TL1A in combination with TGF-β+ IL-6+IL-23 enhances the percentage of IL-17+ cells (FIG. 4D). TL1A also enhances the IFN-γ+ cell population and induces a cell population of IL-17/IFN-γ double positive cells (FIG. 4D). These data confirm data demonstrating concomitant secretion of IL-17 and IFN-γ under TH17 polarizing conditions and simultaneous induction of RORA and t-bet by TL1A.

Figure 5A:
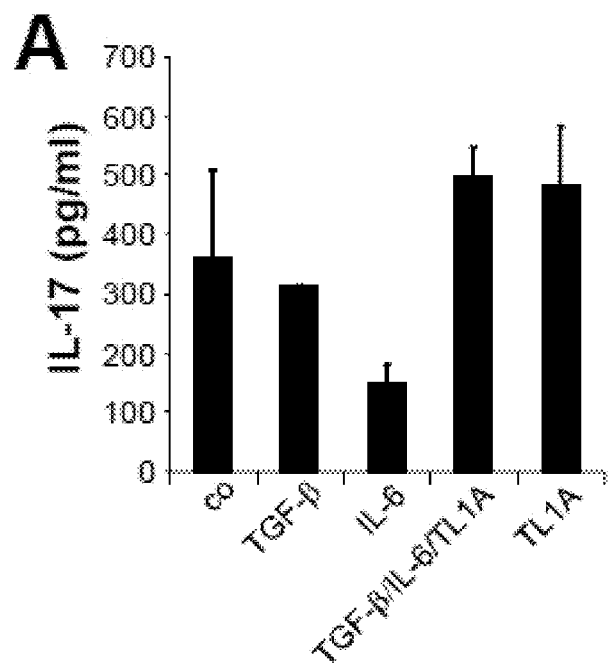
FIGS. 5A-5C depict, in accordance with embodiments herein, TL1A enhances IL-17, IFNγ, and IL-22 secretion from committed CD4+ CD45RO+ CCR6+ TH17 cells.
Figure 5B:
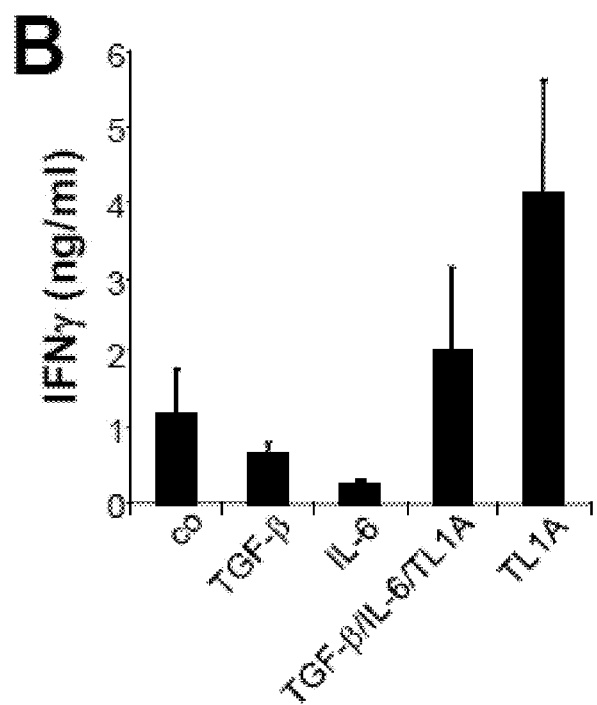
Figure 5C:
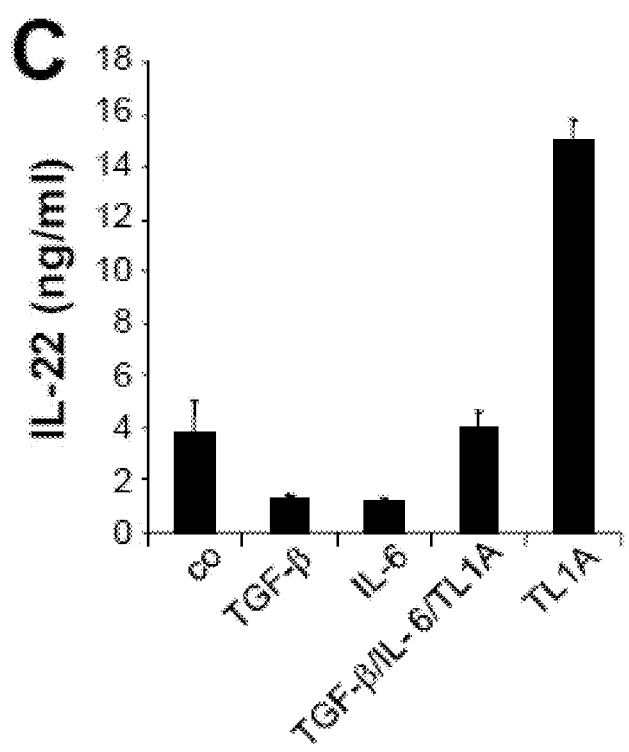

TL1A Increases IL-17 and IL-22 Production in Committed TH17 Cells:

To determine if TL1A could enhance the production of IL-17 from committed TH17 cells, the inventors isolated human CD45RO+CCR6+ cells from peripheral blood and stimulated these cells with TL1A for three days. Stimulation of TH17 cells with TL1A enhances the secretion of IL-17 compared to unstimulated cells by approximately 30% (FIG. 5A). In contrast, treatment with TGF-β or IL-6 decreases the production of IL-17 in committed TH17 cells (FIG. 5A). The inventors also observed an enhancement of IFN-γ and IL-22 production by TL1A alone in committed TH17 cells (FIG. 5B, C).

Figure 6A:
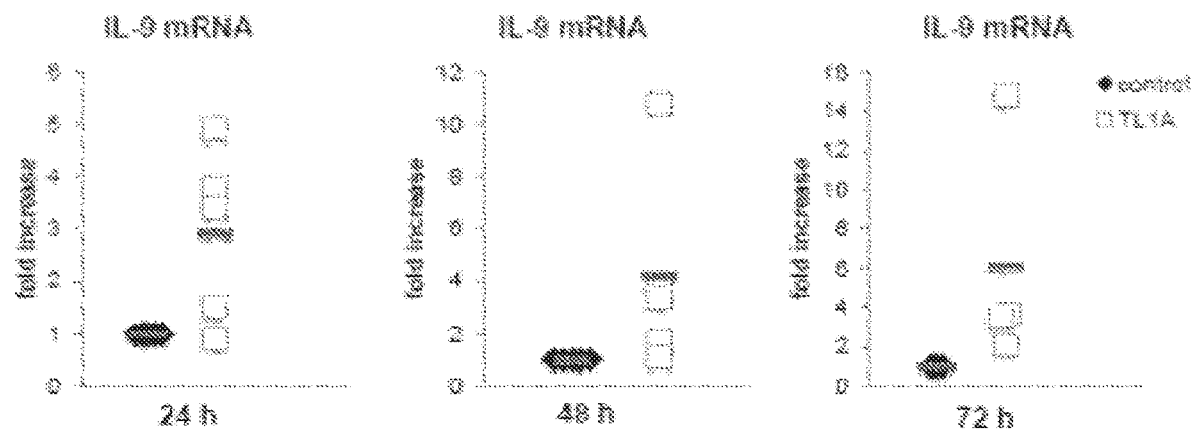
FIGS. 6A-6C depict, in accordance with embodiments herein, TL1A enhances IL-9 mRNA expression and secretion from committed CD4+ CD45RO+ CCR6+TH17 cells.
Figure 6B:
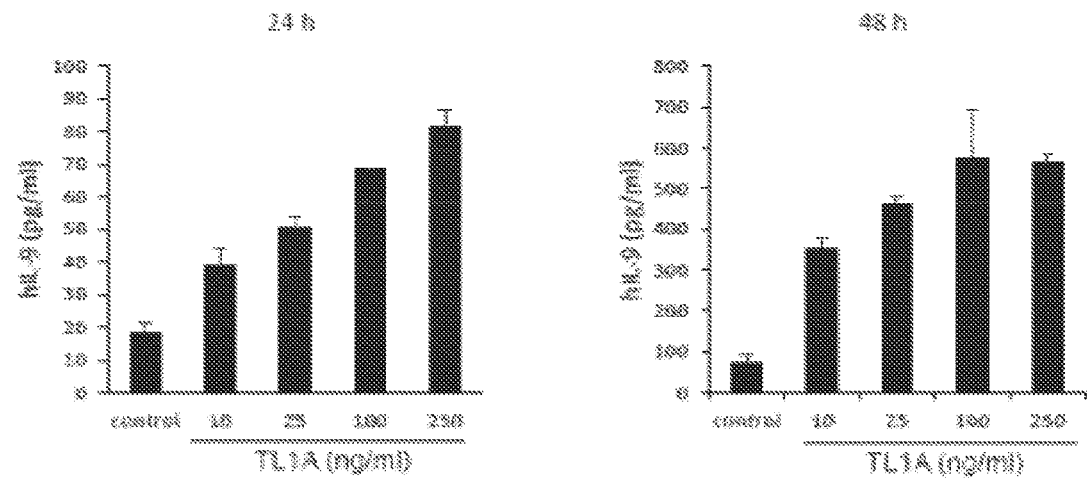
Figure 6C:
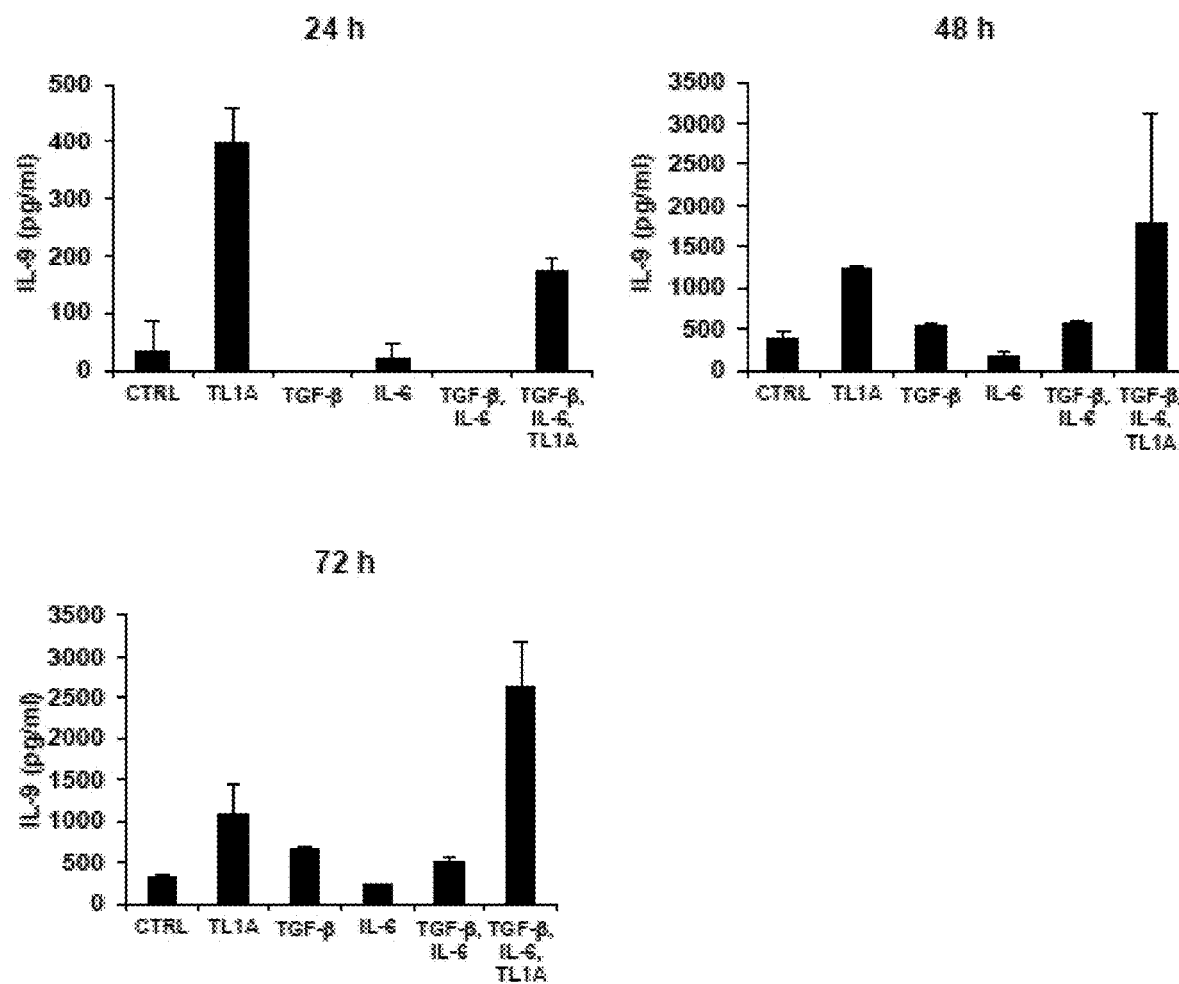
Figure 7:
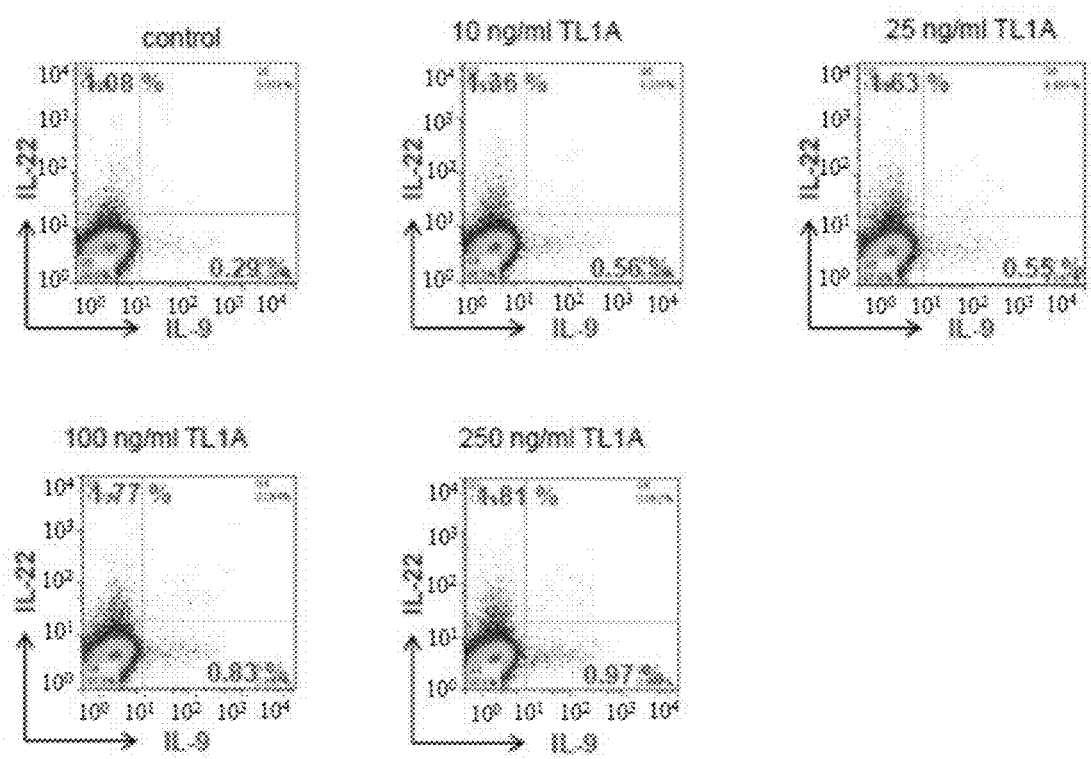
FIG. 7 depicts, in accordance with embodiments herein, TL1A enhances production of IL-9 and IL-22 producing cells. Human CD4+ CD45RO+ T cells were stimulated with TL1A in the indicated concentrations. After 72 h incubation cells were restimulated with PMA/Ionomycin for 5 h and the percentages of IL-22 and IL-9 producing cells were measured by intracellular cytokine staining using flow cytometry. One representative experiment out of three experiments with similar results is shown.
Figure 8:
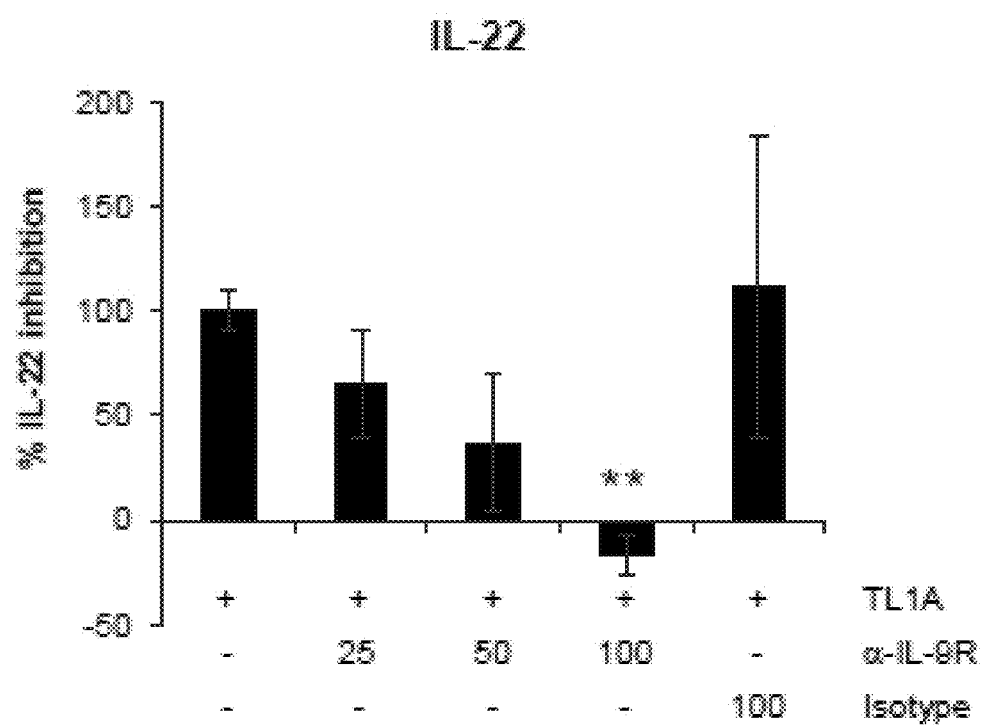
FIG. 8 depicts, in accordance with embodiments herein, IL-9 receptor neutralizing antibodies inhibit TL1A-induced IL-22 secretion from committed CD4+ CD45RO+ CCR6+ TH17 cells. Human CD4+ CD45RO+ CCR6+ TH17 cells were stimulated with anti-CD3, anti-CD28, and TL1A in the presence of neutralizing IL-9 receptor antibodies or isotype controls for 2 days. Supernatants were analyzed for IL-22 by ELISA. Data represent the mean of duplicates ±SD. One representative experiment out of three experiments with similar results is shown. , $p<0.01$
Figure 9:
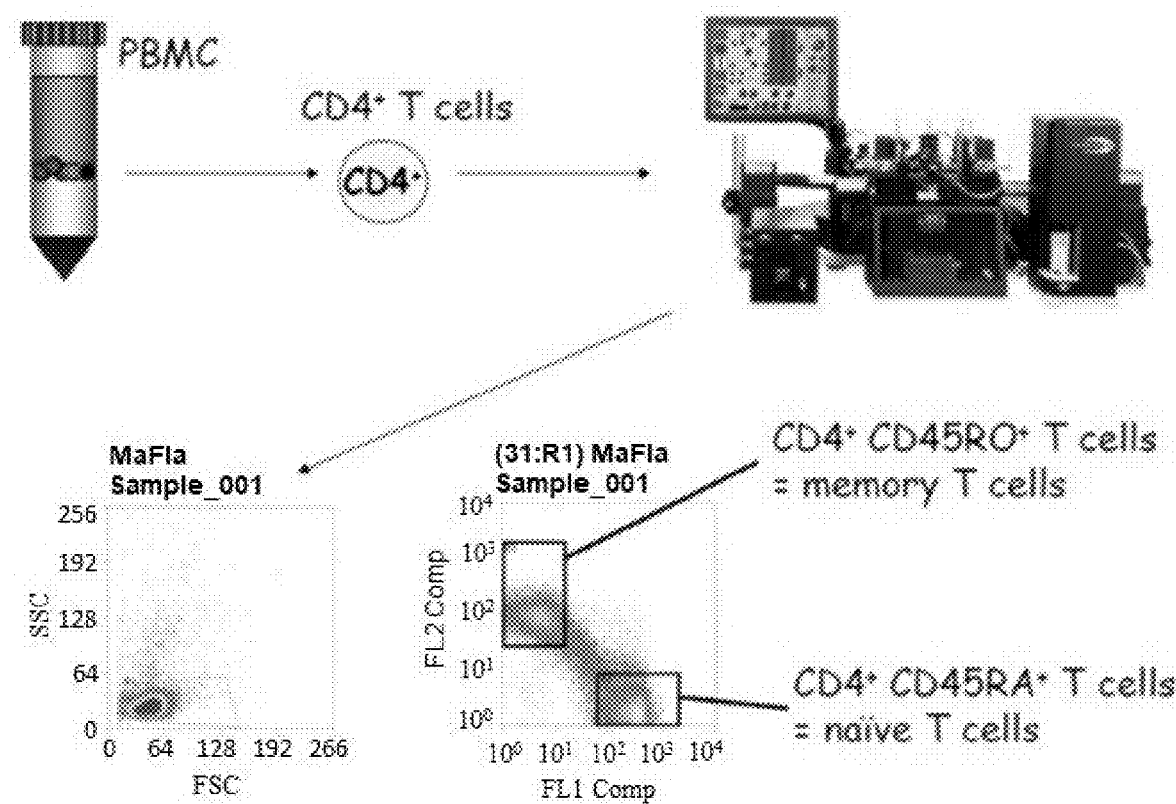
FIG. 9** depicts, in accordance with embodiments herein, methods used by the inventors to determine if TL1A enhances the differentiation and/or activation of Th17 cells in humans.
Figure 10:
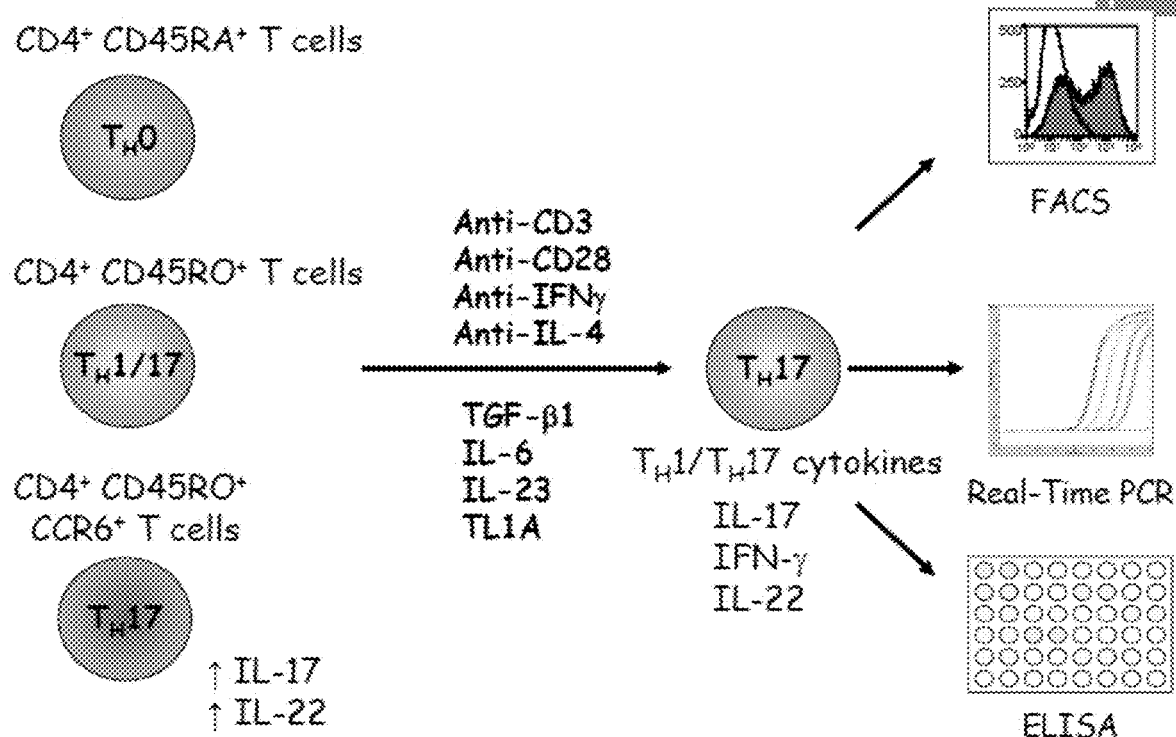
FIG. 10 depicts, in accordance with embodiments herein, methods used by the inventors to determine if TL1A enhances the differentiation and/or activation of Th17 cells in humans.
Figure 11:
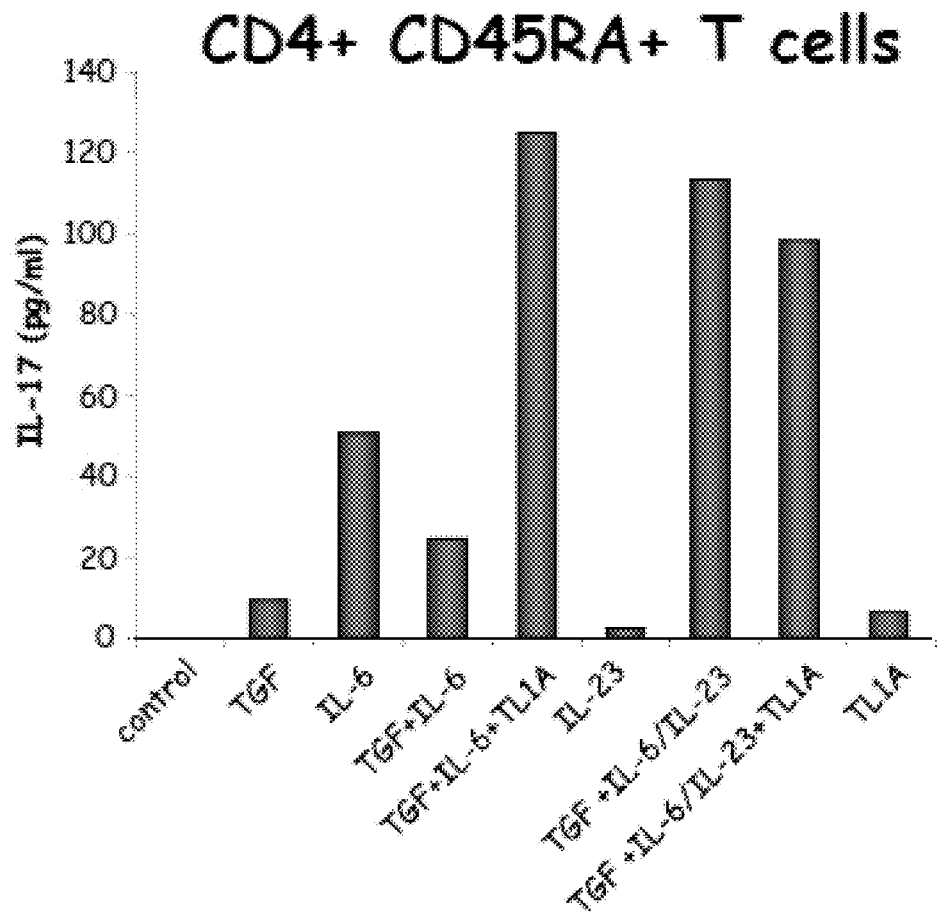
FIG. 11 depicts, in accordance with embodiments herein, TL1A enhances the differentiation of Th17 cells from naïve CD45RA+ T cells. TL1A is able to substitute for IL-23 to achieve maximal induction of IL-17 production from naiive CD4+ T cells.
Figure 12A:
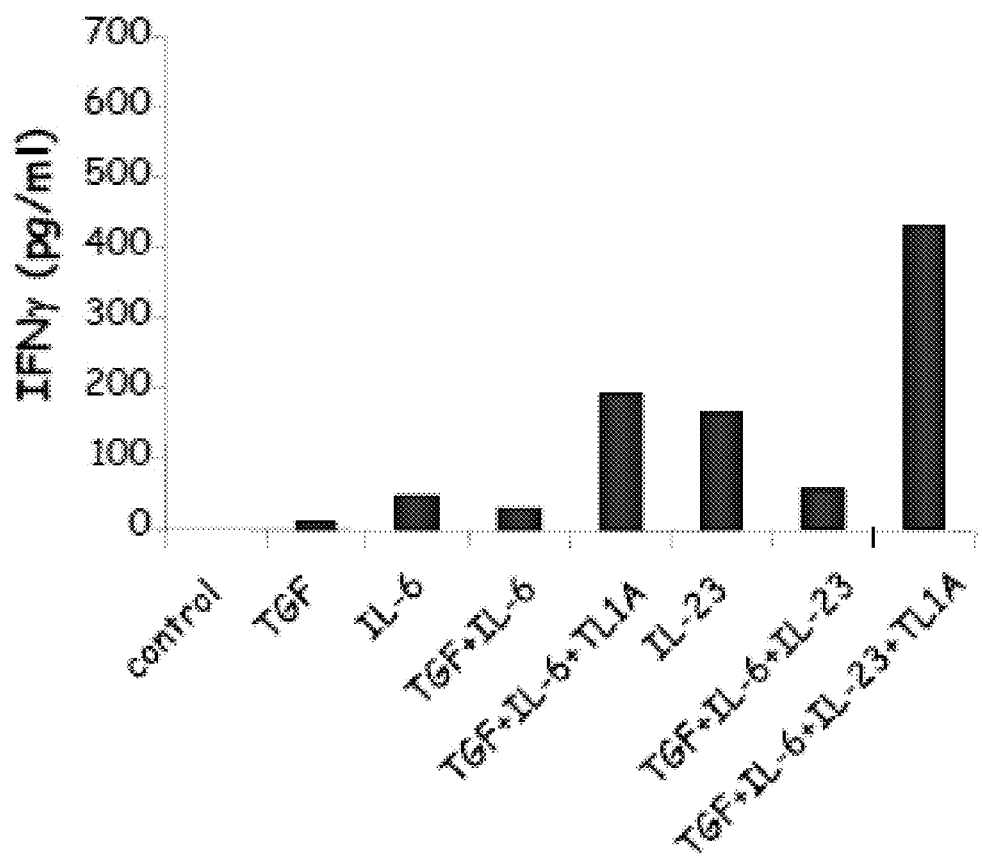
FIGS. 12A-12B depict, in accordance with embodiments herein, TL1A enhances the IFNgamma (FIG. 12A) and induces the IL-22 (FIG. 12B) production of Th17 cells.
Figure 12B:
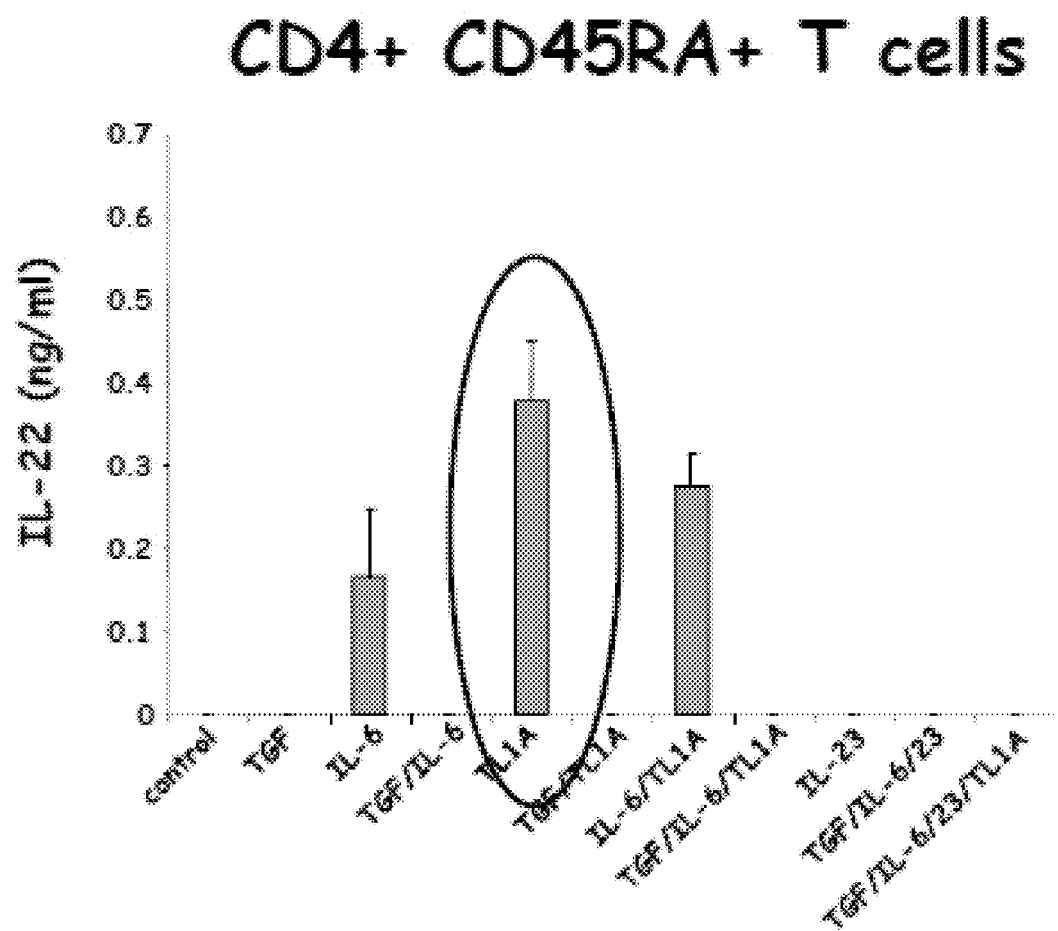
Figure 13A:
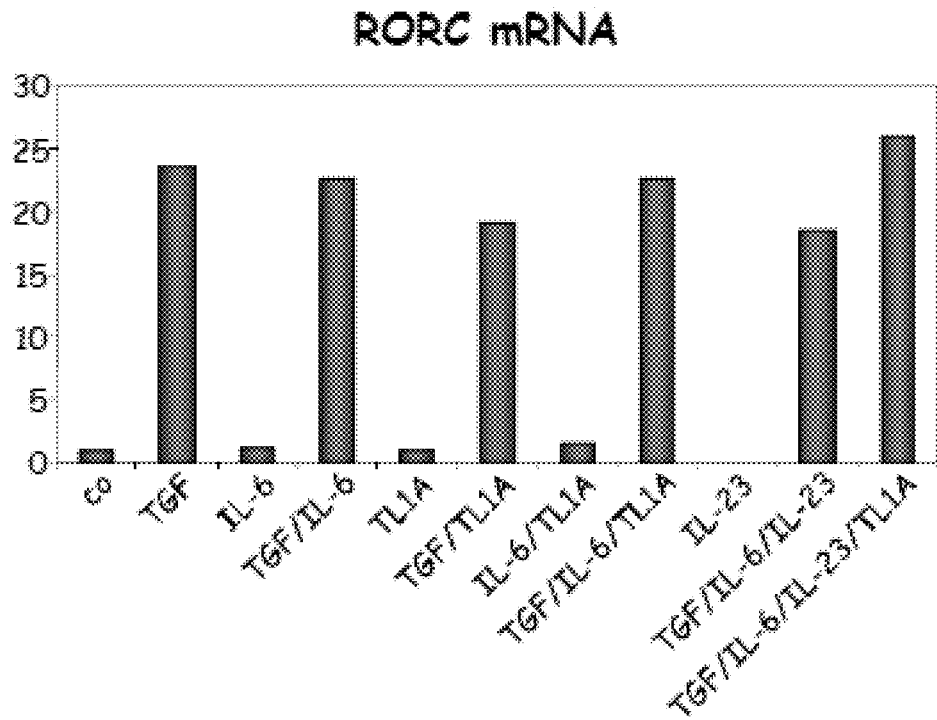
FIGS. 13A-13C depict, in accordance with embodiments herein, TL1A enhances induction of RORA (FIG. 13B) and T-bet mRNA (FIG. 13C) from CD45RA+ T cells, but not expression of RORC (FIG. 13A).
Figure 13B:
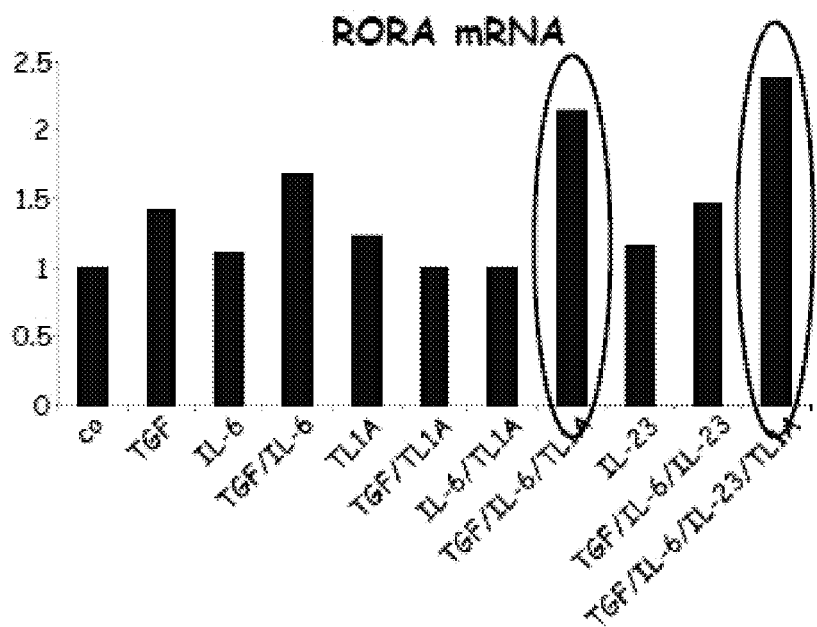
Figure 13C:
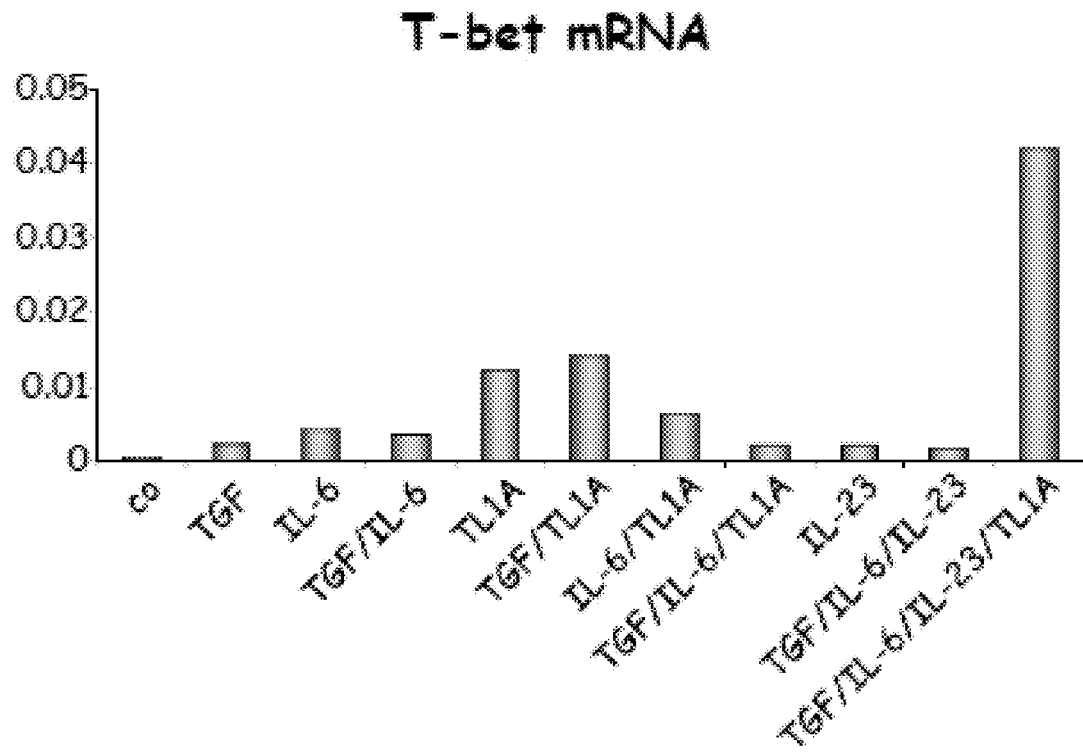
Figure 14A:
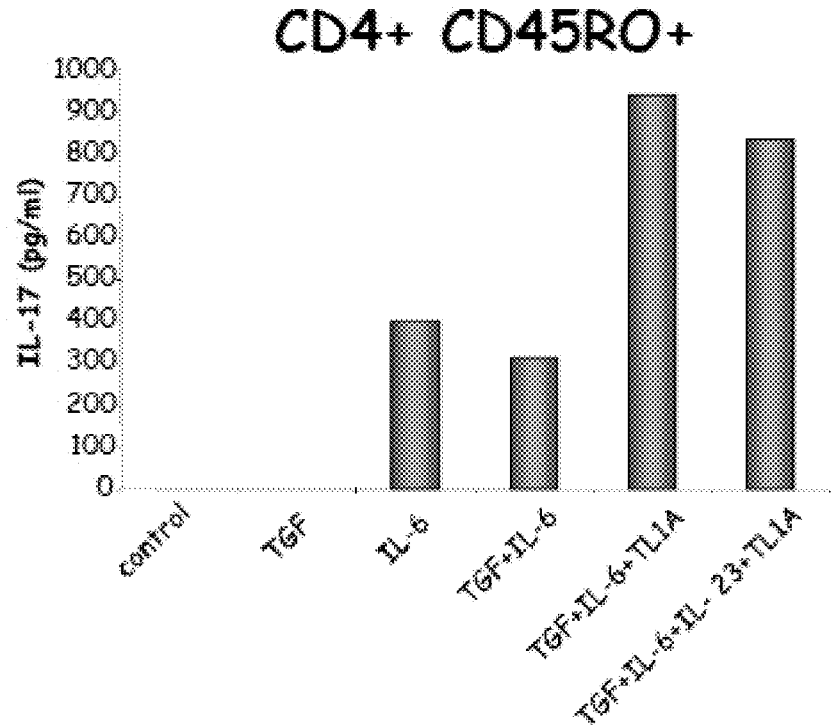
FIGS. 14A-B depict, in accordance with embodiments herein, TL1A enhances the production of IL-17 (FIG. 14A) and IFNgamma (FIG. 14B) from memory CD45RO+ T cells.
Figure 14B:
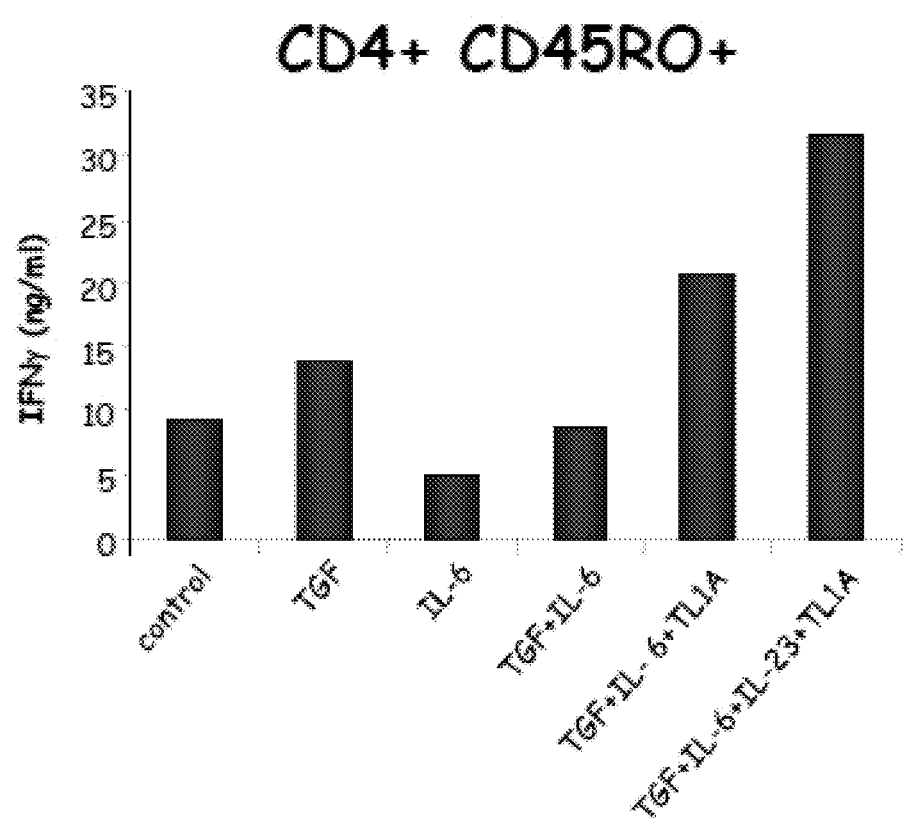
Figure 15:
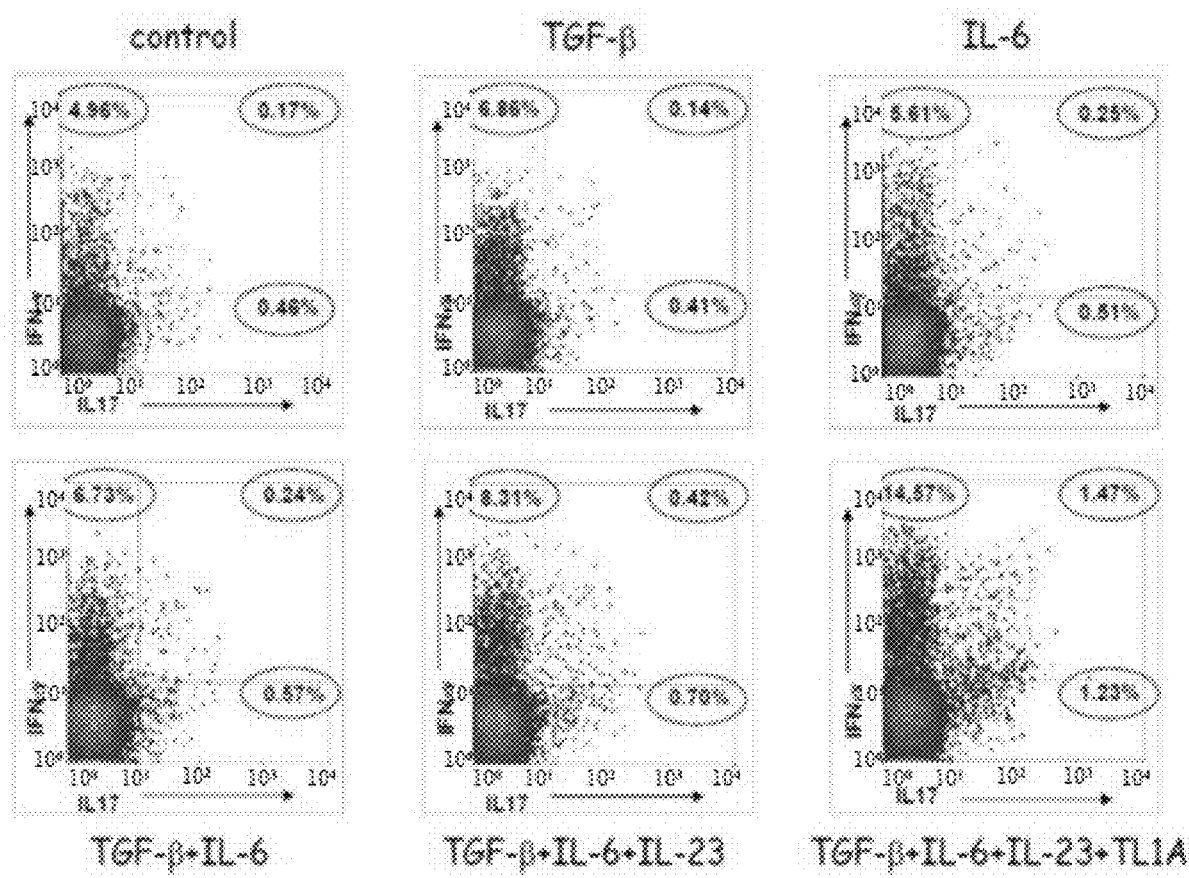
FIG. 15 depicts, in accordance with embodiments herein, TL1A enhances the production of IL-17 from CD45RO+ T cells.
Figure 16:
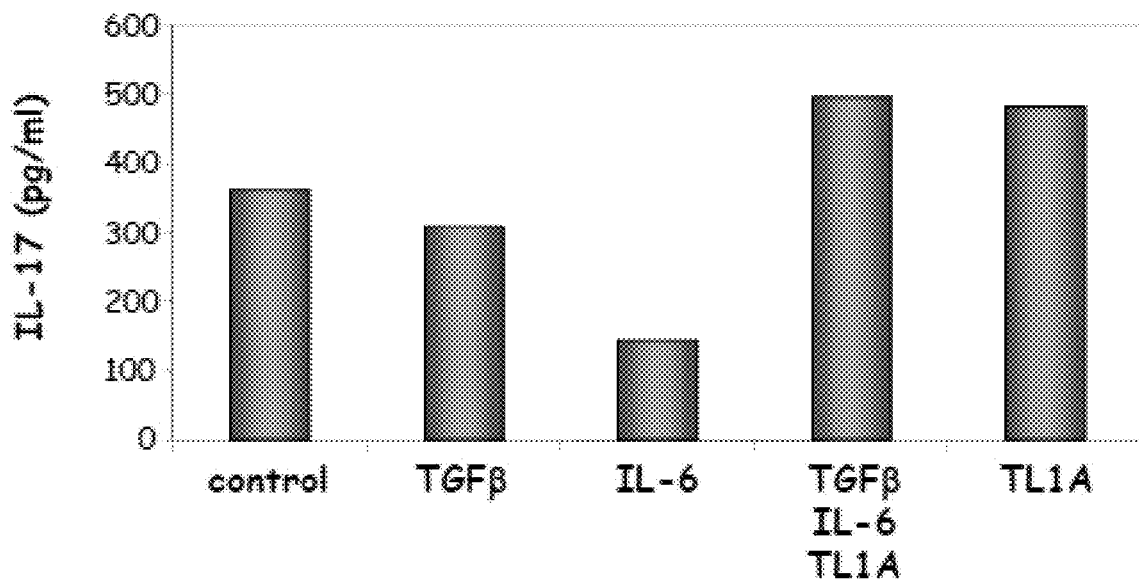
FIG. 16 depicts, in accordance with embodiments herein, TL1A minimally enhances IL-17 production by CD45RO+ CCR6+ Th17 cells. The data is consistent with the finding that TL1A has maximally enhancing effect under suboptimal stimulating conditions.
Figure 17:
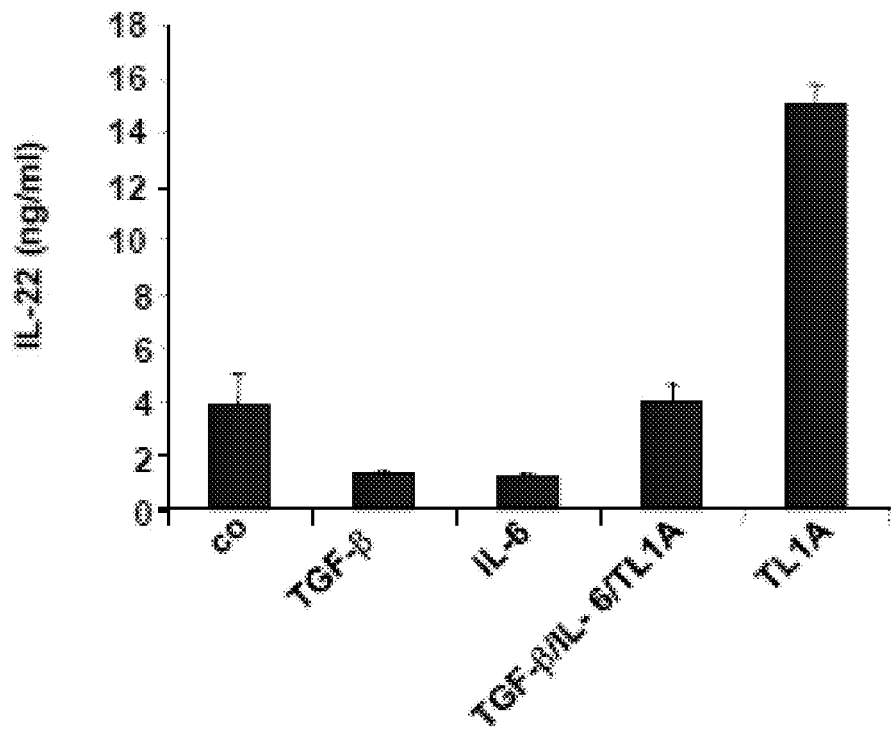
FIG. 17 depicts, in accordance with embodiments herein, TL1A greatly enhances IL-22 production by CD45RO+ CCR6 Th17 cells. The inventors analyzed the expression of IL-22 in TH17 cells after stimulation with TL1A. TL1A alone greatly enhances the production of IL-22 in TH17 cells.
Figure 18:
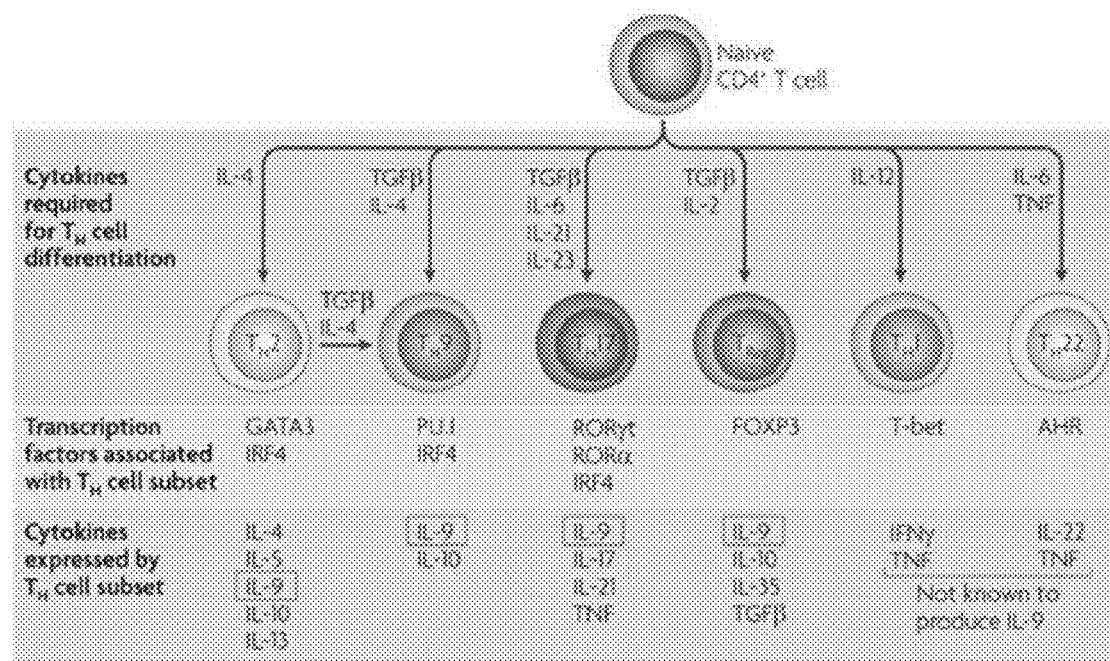
FIG. 18 depicts, in accordance with embodiments herein, a diagram noting that IL-9/Th9 is produced by several T cell subsets including Th17 cells.
Figure 19:
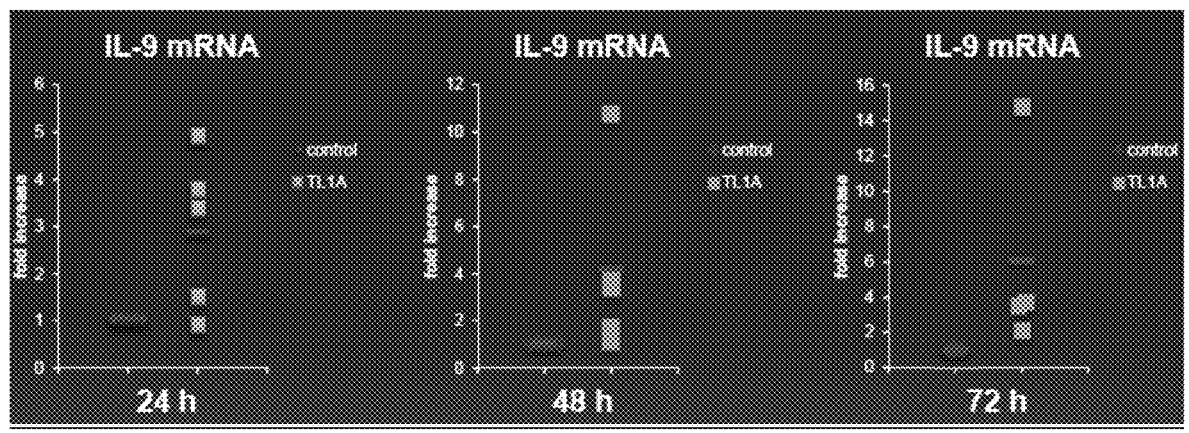
FIG. 19 depicts, in accordance with embodiments herein, TL1A induces IL-9 mRNA.
Figure 20:
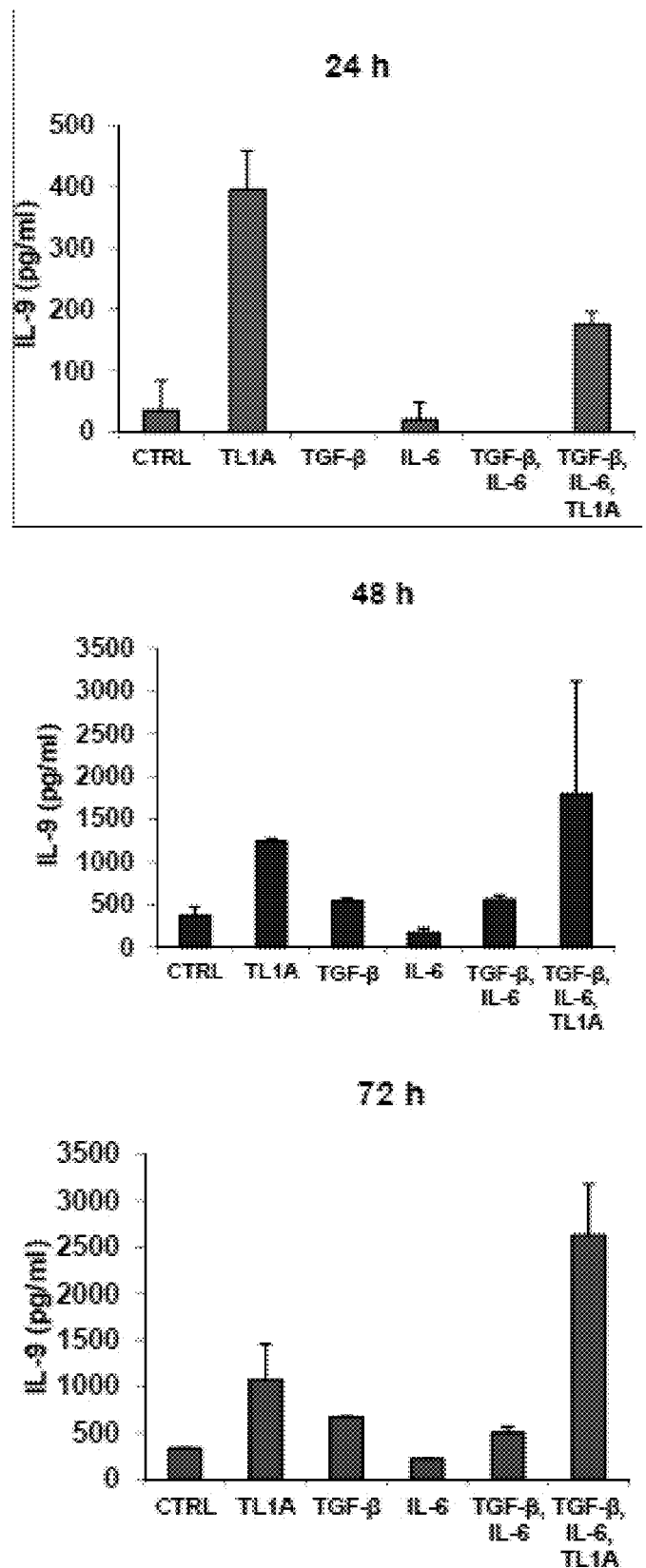
FIG. 20 depicts, in accordance with embodiments herein, TL1A induces early IL-9 secretion in Th17 cells. First, the inventors measured IL-9 secretion upon stimulation with TL1A at different time-point. TL1A induces IL-9 secretion in TH17 cells early on (24 h), 11-fold increase over control cells. At later time-points (72 h) TGF-beta, IL-6, and TL1A have a synergistic effect on the secretion of IL-9, most likely through an indirect mechanism (up-regulation of IL-6/TGF-b receptor by TGF-b or IL-6 or TL1A). TL1A may induce early expression of IL-9 that in turn induces IL-22 expression.
Figure 21:
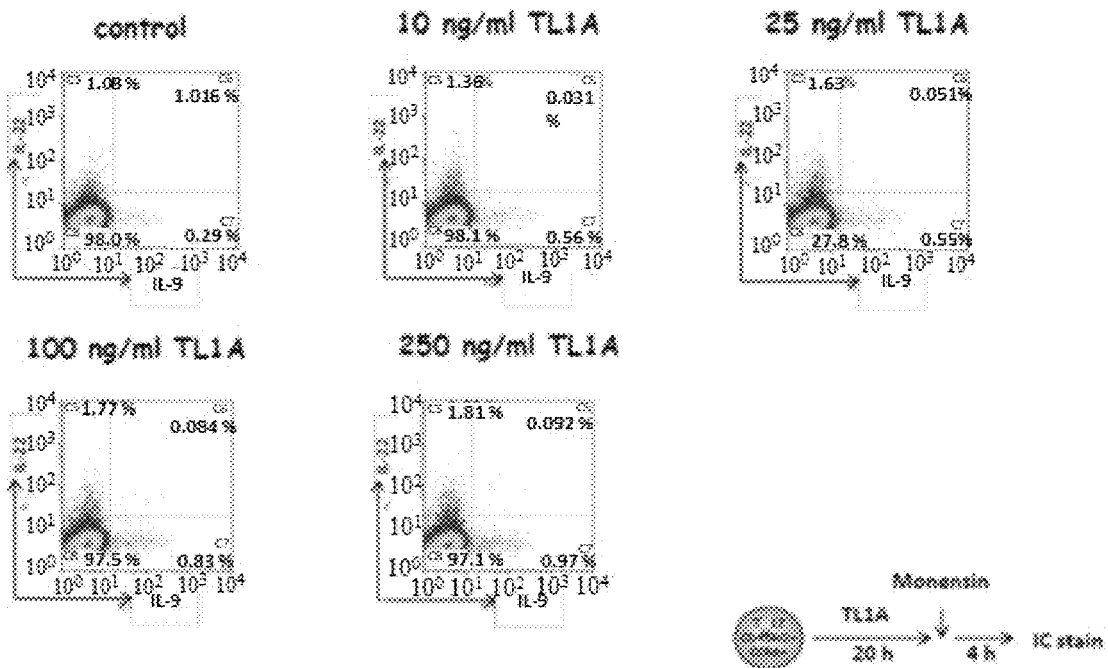
FIG. 21 depicts, in accordance with embodiments herein, TL1A induces IL-9 production in a dose-dependent manner in Th17 cells. TL1A induces IL-9 in committed CD4+ CD45RO+ CCR6+ TH17 cells. Human CD4+ CD45RO+ CCR6+TH17 cells were stimulated for 24 h with plate-bound anti-CD3 and anti-CD28 antibodies with the addition of TL1A at the indicated concentrations. Monensin was added for the last 4 h of stimulation and cells were stained for intracellular IL-9 and IL-22. Data are representative of 3 different experiments.
Figure 22:
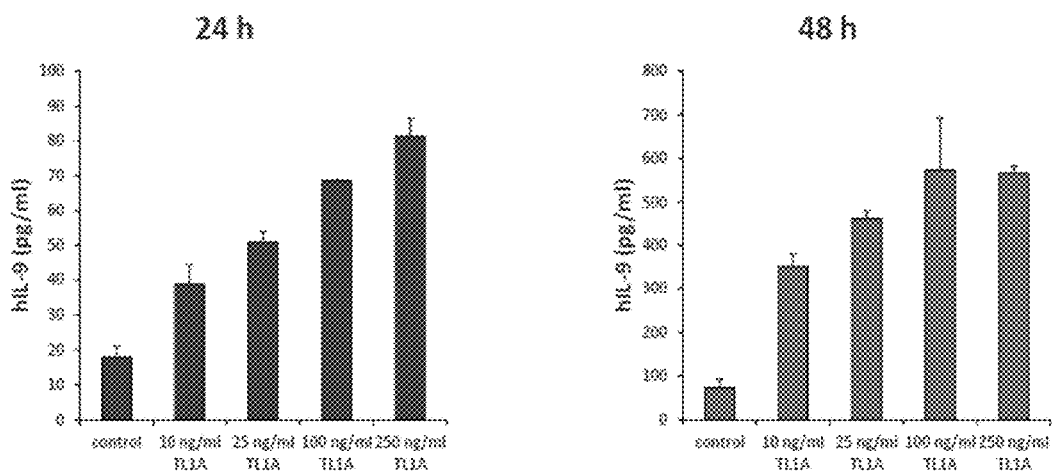
FIG. 22 depicts, in accordance with embodiments herein, TL1A induces IL-9 secretion in Th17 cells in a dose-dependent manner. In parallel, the inventors measured IL-9 in the supernatants of stimulated cells. The inventors observed a dose-dependent increase of IL-9 secretion after stimulation with increasing doses of TL1A at 24 and 48 h.
Figure 23:
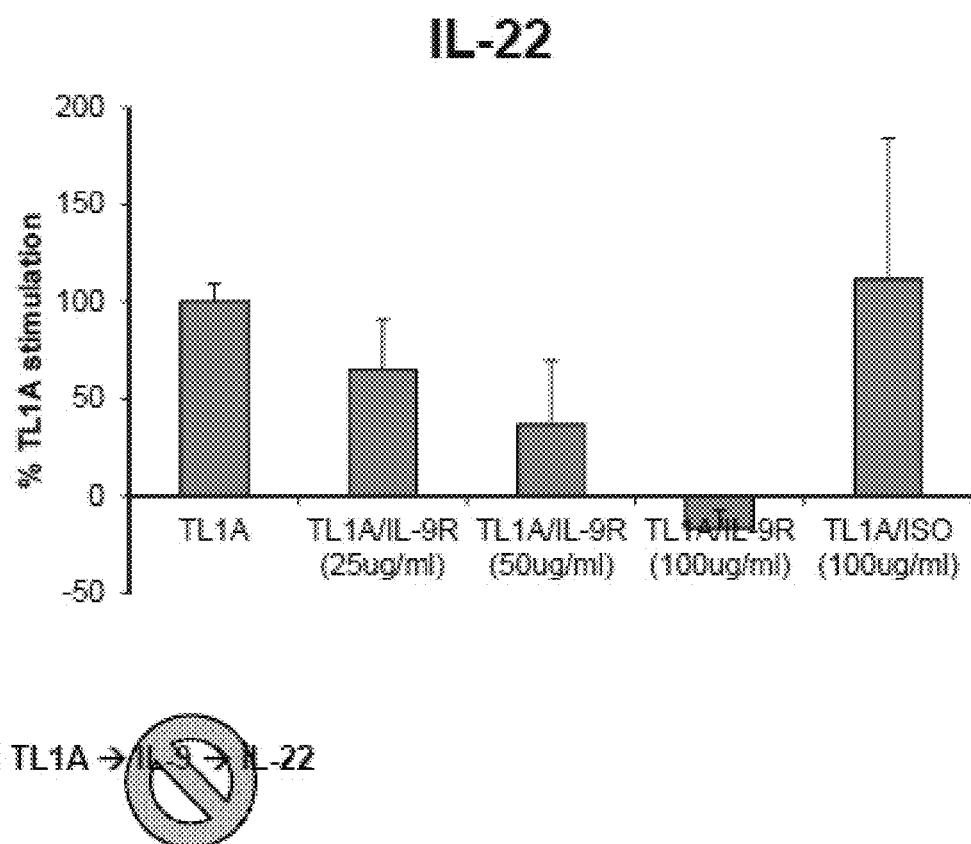
FIG. 23 depicts, in accordance with embodiments herein, IL-9R neutralizing Ab blocks TL1A-induced IL-22 secretion. The inventors used neutralizing anti-IL9 receptor antibodies to block the TL1A-induced induction of IL-22. Neutralizing anti-IL9R Ab blocks IL-22 in a dose-dependent manner. A dosage of 100 ug/ml results in a reduction of IL-22 secretion back to control levels. Left panel: secretion of IL-22 in response to TL1A-absolute values. Right panel: % of inhibition of TL1A-induced IL-22. 24 h time-point.
Figure 24:
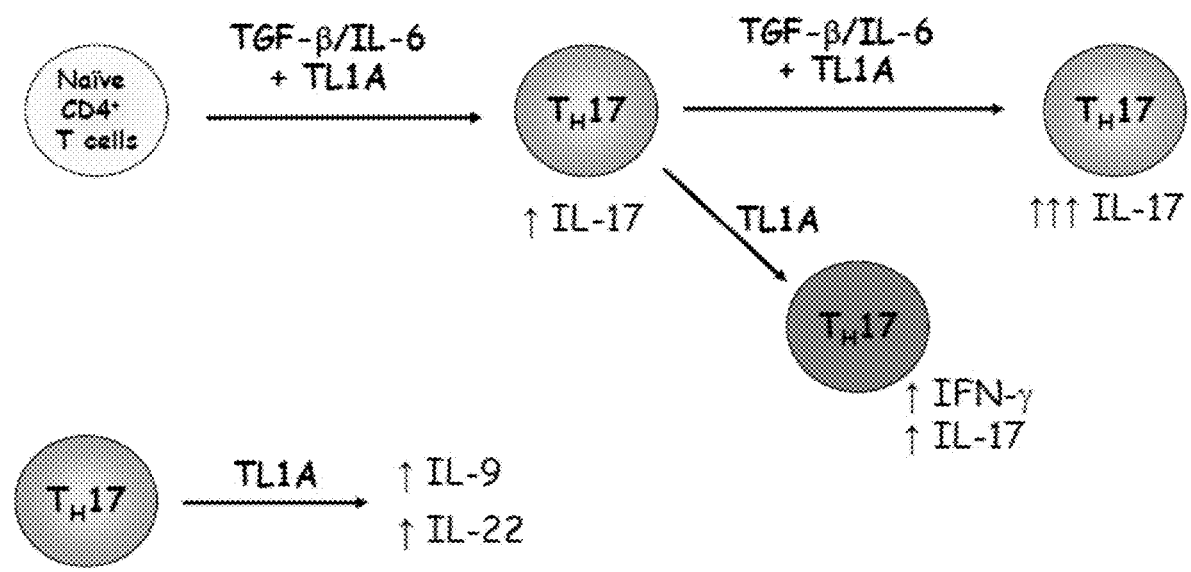
FIG. 24 depicts, in accordance with embodiments herein, a diagram of overall results.

Increased IL-22 Production in Committed TH17 Cells by TL1A Stimulation is Driven by IL-9 secretion:

In order to determine the mechanism of TL1A-induced IL-22 production in TH17 cells the inventors performed global gene expression analysis of TL1A-stimulated TH17 cells (FIG. 6A). Stimulation of TH17 cells with TL1A resulted in the up-regulation of 76 genes by at least 2-fold and the down-regulation of 90 genes by at least 2-fold. The inventors observed that the expression of the cytokine IL-9 was up-regulated by TL1A stimulation. Since IL-9 has been described to be an inducer of IL-22 the inventors believed that the induction of IL-9 by TL1A could lead to the up-regulation of IL-22. First, they confirmed gene array data by quantitative real-time PCR. IL-9 mRNA expression was induced early on in TL1A-stimulated TH17 cells and remained up-regulated for up to 72 h (FIG. 6B). Next, confirmed TL1A induced IL-9 secretion in TH17 cells. They observed a dose-dependent increase of IL-9 secretion after stimulation with TL1A at 24 and 48 h (FIG. 6C). Concomitant with a dose-dependent increase of IL-9 by TL1A stimulation they also observed an increase in IL-22+ and IL-9+IL-22+ cells as detected by intracellular cytokine staining (FIG. 7). To prove the hypothesis that the TL1A-induced secretion of IL-22 is dependent on IL-9 they utilized anti-IL-9R neutralizing antibodies. According to the hypothesis they observed a dose-dependent inhibition of TL1A-induced IL-22 (FIG. 8). They observed similar results with neutralizing anti-IL-9 antibodies. These data demonstrate that TL1A induces IL-22 in TH17 cells via the early induction of IL-9.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s). The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

What is claimed is:

1. A method of monitoring an effectiveness of an anti-TL1A therapy to reduce expression of TL1A in a subject, the method comprising:
   a) measuring in a sample obtained from a subject with an inflammatory bowel disease or allergic lung inflammation a level of expression of interleukin-9 (IL-9);
   b) detecting an elevated level of expression of IL-9 in the sample as compared to a level of expression of IL-9 in an individual who does not have the inflammatory bowel disease or allergic lung inflammation;
   c) administering to the subject an anti-TL1A antibody;
   d) determining a presence of a downregulation of IL-9; and
   e) determining that the administration of the anti-TL1A antibody is effective to reduce an elevated level of TL1A in the subject.

2. The method of claim 1, wherein the elevated level of expression of IL-9 is at least a 10-fold increase over the level of expression of IL-9 in an individual who does not have the inflammatory bowel disease or allergic lung inflammation.

3. The method of claim 1, wherein an elevated level of expression of TL1A is detected in the sample obtained from the subject.

4. The method of claim 1, further comprising detecting an elevated level of interleukin-22 (IL-22) in the sample obtained from the subject.

5. The method of claim 1, wherein IL-9 is IL-9 ribonucleic acid (RNA).

6. A method of treating an inflammatory bowel disease or allergic lung inflammation in a subject with an anti-TL1A-antibody, the method comprising:
   a) administering to the subject a dosage of the anti-TL1A antibody;
   b) determining whether the dosage of the anti-TL1A antibody is therapeutically effective to treat the inflammatory bowel disease or allergic lung inflammation in the subject by determining a presence of a downregulation of interleukin-9 (IL-9); and
   c) continue administering the anti-TL1A antibody to the subject administering, to the subject, a second dosage of the TL1A antibody.

7. The method of claim 6, wherein determining whether the dosage of an anti-TL1A antibody is therapeutically effective to treat the inflammatory bowel disease or allergic lung inflammation in the subject further comprises determining a presence of a downregulation of interleukin-22 (IL-22).

8. The method of claim 6, wherein the downregulation is determined in blood and/or an intestinal tissue biopsy from the subject.

9. The method of claim 6, wherein IL-9 is IL-9 ribonucleic acid (RNA).

10. The method of claim 6, wherein the inflammatory bowel disease is Crohn's disease.

\* \* \* \* \*

SEQUENCE LISTING

```
<160> NUMBER OF SEQ ID NOS: 30

<210> SEQ ID NO 1
<211> LENGTH: 24
<212> TYPE: DNA
<213> ORGANISM: Artificial Sequence
<220> FEATURE:
<223> OTHER INFORMATION: primer

<400> SEQUENCE: 1
ccacttccag ccgaggtcct tgcg                                           24

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gctccacgga gaagaactgc                                                20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gttggcatgg tagcccttgg                                                20
```

```
<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
ctgctgttgc tgctgccctg gaca                                          24

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gctggggagc agagctgtaa                                               20

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
cttctgtgaa agctgctggc a                                             21

<210> SEQ ID NO 7
<211> LENGTH: 24
<212> TYPE: DNA
<213> ORGANISM: Artificial Sequence
<220> FEATURE:
<223> OTHER INFORMATION: primer

<400> SEQUENCE: 7
accacaagca tgagccacca cgcc                                          24

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
agcctgggaa acataacaag acc                                           23

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
tcctgcctca tcctcctgaa c                                             21

<210> SEQ ID NO 10
<211> LENGTH: 24
<212> TYPE: DNA
<213> ORGANISM: Artificial Sequence
<220> FEATURE:
<223> OTHER INFORMATION: primer
```

<400> SEQUENCE: 10
ctgctcctgg tgttgcctgc tgcc                                              24

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
cttcggtcca gttgccttct c                                                 21

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
aagaggtgag tggctgtctg t                                                 21

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
acaccaatgc ccaactgcct gcct                                              24

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
tatagcctgg actttcctgt tgtc                                              24

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
gctgactgtc ctggctgatg                                                   20

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
acctgcttgt cagccagctc cgg                                               23

<210> SEQ ID NO 17

```
<211> LENGTH: 21
<212> TYPE: DNA
<213> ORGANISM: Artificial Sequence
<220> FEATURE:
<223> OTHER INFORMATION: primer

<400> SEQUENCE: 17
cttccttgca ggactcacca c                                              21

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18
gctgatgtga aggtgcaaac tc                                             22

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
cggctacagc ttcaccacca cggc                                           24

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
gactacctca tgaagatcct cacc                                           24

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
tctccttaat gtcacgcacg att                                            23

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
tctcagggtc ctcattgcgg ctgc                                           24

<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23
```
aacttgcctc tcttcatgta ttcc　　　　　　　　　　　　　　　24

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
actttgcctc ccagatcaca g　　　　　　　　　　　　　　　21

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
ttgatgggaa gtatgccagc　　　　　　　　　　　　　　　20

<210> SEQ ID NO 26
<211> LENGTH: 29
<212> TYPE: DNA
<213> ORGANISM: Artificial Sequence
<220> FEATURE:
<223> OTHER INFORMATION: primer

<400> SEQUENCE: 26
cggtgccttt gactctcaga acaacaccg　　　　　　　　　　　29

<210> SEQ ID NO 27
<211> LENGTH: 24
<212> TYPE: DNA
<213> ORGANISM: Artificial Sequence
<220> FEATURE:
<223> OTHER INFORMATION: primer

<400> SEQUENCE: 27
tctttccaaa ttcaaacaca aagc　　　　　　　　　　　　　24

<210> SEQ ID NO 28
<211> LENGTH: 24
<212> TYPE: DNA
<213> ORGANISM: Artificial Sequence
<220> FEATURE:
<223> OTHER INFORMATION: primer

<400> SEQUENCE: 28
tccgccgtcc ctgcttggtg atga　　　　　　　　　　　　　24

<210> SEQ ID NO 29
<211> LENGTH: 24
<212> TYPE: DNA
<213> ORGANISM: Artificial Sequence
<220> FEATURE:
<223> OTHER INFORMATION: primer

<400> SEQUENCE: 29
ccaagtttaa tcagcaccag acag　　　　　　　　　　　　　24

<210> SEQ ID NO 30
<211> LENGTH: 23
<212> TYPE: DNA

```
<213> ORGANISM: Artificial Sequence
<220> FEATURE:
<223> OTHER INFORMATION: primer

<400> SEQUENCE: 30
gccacagtaa atgacaggaa tgg                                              23
```